United States Patent [19]

Matsuo et al.

[11] Patent Number: 5,296,495
[45] Date of Patent: Mar. 22, 1994

[54] THIAZOLYLBENZOFURAN DERIVATIVES AND PHARMACEUTICAL COMPOSITION COMPRISING THE SAME

[75] Inventors: Masaaki Matsuo, Toyonaka; Kazuo Okumura, Osaka; Shinji Shigenaga, Kobe; Hiroshi Matsuda, Osaka, all of Japan

[73] Assignee: Fujisawa Pharmaceutical Co., Ltd., Osaka, Japan

[21] Appl. No.: 929,751

[22] Filed: Aug. 12, 1992

[30] Foreign Application Priority Data

Aug. 16, 1991 [GB] United Kingdom ............. 9117733.7
Jan. 17, 1992 [GB] United Kingdom ............. 9201057.8

[51] Int. Cl.$^5$ .................. A61K 31/425; C07D 417/04; C07D 417/14
[52] U.S. Cl. ..................... 514/365; 514/215; 514/337; 514/338; 514/367; 540/578; 546/269; 546/270; 546/274; 548/159; 548/201; 548/203; 548/204; 548/205
[58] Field of Search ............... 548/203, 205, 159, 201, 548/204; 514/365, 215, 337, 338, 367; 540/578; 546/269, 270, 274

[56] References Cited

U.S. PATENT DOCUMENTS

| | | | |
|---|---|---|---|
| 4,742,057 | 5/1988 | Ueda et al. | 514/235.2 |
| 4,902,700 | 2/1990 | Hayasi et al. | 514/365 |
| 4,908,357 | 3/1990 | Lutomski et al. | 514/92 |
| 5,001,140 | 3/1991 | Field et al. | 514/365 |
| 5,032,588 | 7/1991 | Brooks et al. | 514/224.8 |

FOREIGN PATENT DOCUMENTS

| | | | |
|---|---|---|---|
| 0432740 | 6/1991 | European Pat. Off. | 548/203 |
| WO90/06920 | 6/1990 | PCT Int'l Appl. | |

OTHER PUBLICATIONS

Chemical Abstracts, vol. 60, p. 10839, 10839f, E. D. Sych et al., "Thiazolecyanines. XI. Synthesis of Thiazolocyanines from Heterocyclic-Substituted Thiazoles", (1959).
Chemical Abstracts, vol. 70, p. 280, 11630b, G. Kempter et al., "Heterocycles from 2-Bromoacetyl Heterocycles", (1969).
Chemical Abstracts, vol. 90, p. 603, 90:152062t, G. Sarodnick et al., "Heterocyclic Substituted Thiazoles as Thiabendazole Analogs", 1979.
J. Heterocycl. Chem., vol. 16, pp. 97-103, Jan. 1977, G. Vernin et al., "Homolytic Aromatic Substitution of Heterocyclic Compounds. Part XIII. Arylation and Heteroarylation of Coumarin and Benzo[b]furan Using Triazenes as the Source of Radicals. An Experimental and Theoretical Study (1)".
J. Med. Chem., vol. 33, pp. 1186-1194, 1990, R. D. Youssefyeh et al., "Development of a Novel Series of (2-Quinolinylmethoxy)phenyl-containing Compounds as High-Affinity Leukotriene Receptor Antagonists. 1. Initial Structure-Activity Relationships".

Primary Examiner—Mary C. Lee
Assistant Examiner—Jacqueline Haley
Attorney, Agent, or Firm—Oblon, Spivak, McClelland, Maier & Neustadt

[57] ABSTRACT

Compounds of the formula:

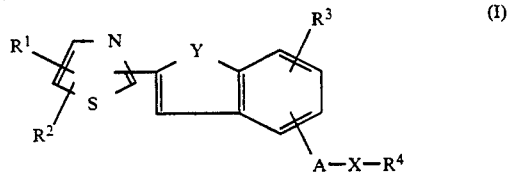

wherein $R^1$, $R^2$, $R^3$, $R^4$, A, X and Y are as defined and pharmaceutically acceptable salts thereof; which have activities as leukotriene and Slow Reacting Substance of Anaphalaxis (SRS-a) antagonists or inhibitors, to processes for preparation thereof, to a pharmaceutical composition comprising the same, and to methods of using the same therapeutically in the prevention and/or treatment of allergy or inflamation in human beings or animals.

8 Claims, No Drawings

THIAZOLYLBENZOFURAN DERIVATIVES AND PHARMACEUTICAL COMPOSITION COMPRISING THE SAME

This invention relates to new thiazolylbenzofuran derivatives and pharmaceutically acceptable salts thereof.

More particularly, it relates to new thiazolylbenzofuran derivatives and pharmaceutically acceptable salts thereof which have activities as leukotriene and Slow Reacting Substance of Anaphylaxis (hereinafter, SRS-A) antagonists or inhibitors, to processes for preparation thereof, to a pharmaceutical composition comprising the same, and to methods of using the same therapeutically in the prevention and/or treatment of allergy or inflammation in human beings or animals, and more particularly to methods for prevention and/or treatment of asthma, psoriasis, hepatitis, bronchitis, gastritis, esophagitis, pancreatitis, arthritis, nephritis, inflammatory bowel disease, shock [e.g., septic shock, anaphylactic shock, etc.], arteriosclerosis, myocardial infarction, cerebral vasospasm, rhinitis, conjunctivitis, eczema, ischemic cerebral disease, chronic obstructive lung disease, cerebral edema, adult respiratory distress syndrome, neonatal pulmonary hypertension, Chrohn's diseases, dermatitis, rheumatism, gastric ulcer, peptic ulcer, gout and the like.

One object of this invention is to provide new and useful thiazolylbenzofuran derivatives and pharmaceutically acceptable salts thereof which possess activities as leukotriene and SRS-A antagonists or inhibitors.

Another object of this invention is to provide processes for the preparation of said derivatives and salts thereof.

A further object of this invention is to provide a pharmaceutical composition comprising, as an active ingredient, said thiazolylbenzofuran derivatives and pharmaceutically acceptable salt thereof.

Still further object of this invention is to provide a therapeutical method for the prevention and/or treatment of allergy or inflammation, and more particularly of asthma, psoriasis, hepatitis, bronchitis, gastritis, esophagitis, pancreatitis, arthritis, nephritis, inflammatory bowel disease, shock [e.g. septic shock, anaphylactic shock, etc.], arteriosclerosis, myocardial infarction, cerebral vasospasm, rhinitis, conjunctivitis, eczema, ishemic cerebral disease, chronic obstructive lung disease, cerebral edema, adult respiratory distress syndrome, neonatal pulmonary hypertension, Chrohn's disease, dermatitis, rheumatism, gastric ulcer, peptic ulcer, gout and the like, using said thiazolylbenzofuran derivatives and pharmaceutically acceptable salts thereof.

Some thiazolylbenzofuran derivatives have known as described, for example, in J. Heterocycl. Chem., 16, 97(1979) and Chemical Abstract, 70, 11630b and 90, 152062t.

The object thiazolylbenzofuran derivatives of this invention are new and can be represented by the following general formula (I):

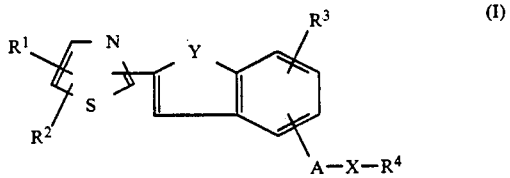

wherein
$R^1$ is lower alkyl optionally substituted with halogen, lower alkylamino or lower alkyl(acyl)amino; cyclo(lower)alkyl; tricycloalkyl; aryl optionally substituted with lower alkoxy; or a heterocyclic group;
$R^2$ is hydrogen or halogen, or
$R^1$ and $R^2$ are taken together with the adjacent atoms to form cycloalken ring or an N-containing heterocyclic group optionally substituted with acyl,
$R^3$ is hydrogen, halogen, hydroxy, lower alkyl or lower alkoxy,
$R^4$ is hydrogen; acyl; cyano; aryl optionally substituted with hydroxy(lower)alkyl, halo(lower)alkyl, cyano(lower)alkyl, heterocyclic(lower)alkyl or acyl; or lower alkyl which may be substituted with substituent(s) selected from the group consisting of halogen, cyano, hydroxy, lower alkylsulfonyloxy, arylsulfonyloxy, acyl, acyl(lower)alkylthio and aryl optionally substituted with halo(lower)alkyl, cyano(lower)alkyl, heterocyclic(lower)alkyl, cyano, acyl, acyl(lower)alkyl, a heterocyclic group or [lower alkylsulfinyl)(lower alkylthio)lower alkenyl];
A is lower alkylene, lower alkenylene or a single bond,
X is a single bond, O or S, and
Y is O or S,
provided that A is lower alkylene or lower alkenylene, or
X is O or S when $R^1$ is lower alkyl or aryl and $R^2$ is hydorgen,
and pharmaceutically acceptable salts thereof.

The object compound (I) or its salt can be prepared by processes as illustrated in the following reaction schemes.

Process 1

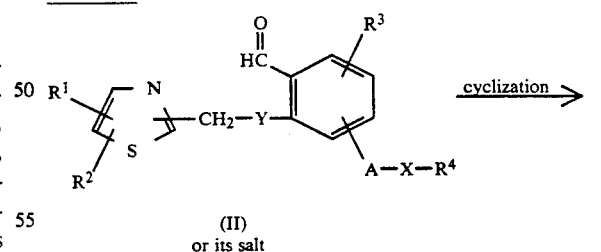

(II)
or its salt

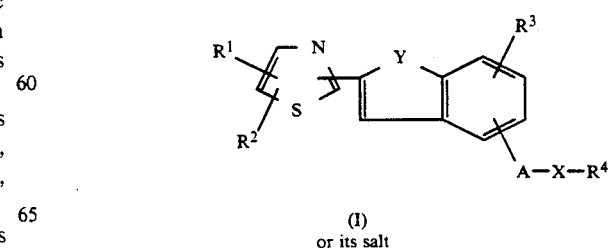

(I)
or its salt

Process 2

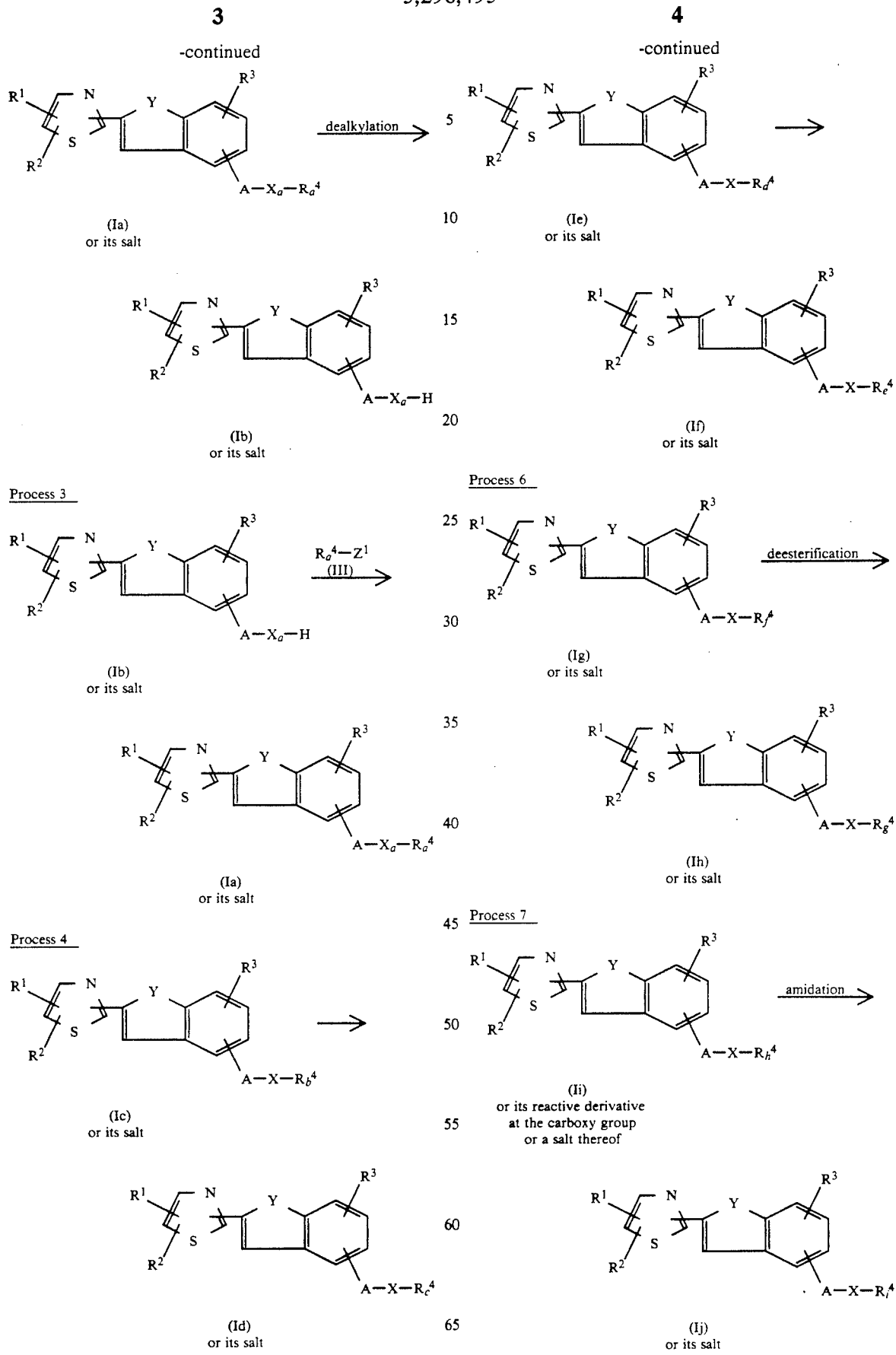

-continued
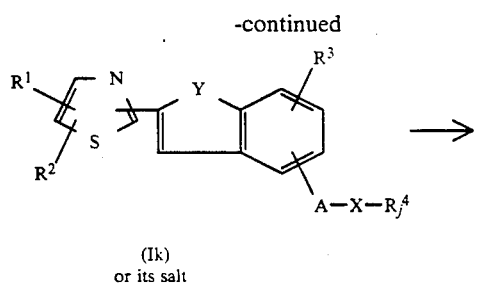
(Ik) or its salt
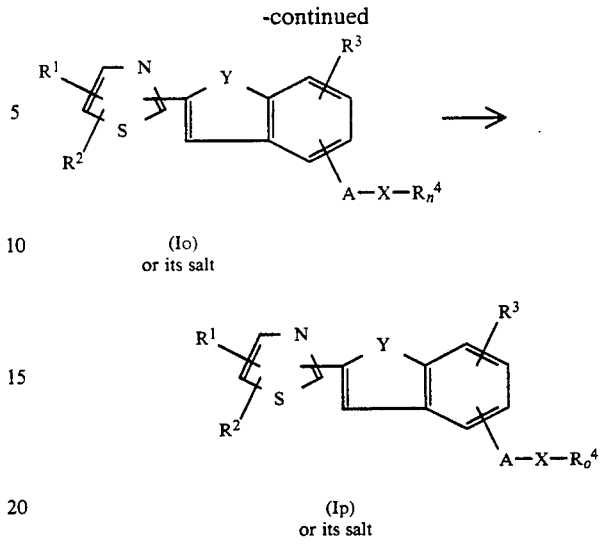
(Io) or its salt
(Il) or its salt
(Ip) or its salt
Process 9
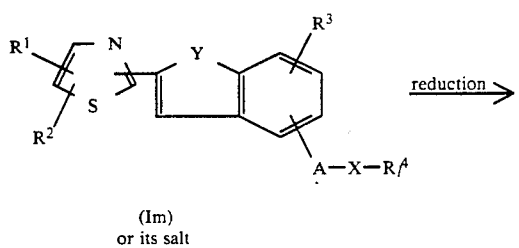
(Im) or its salt
Process 12
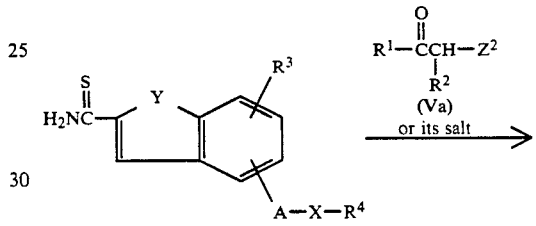
(IV) or its salt
(In) or its salt
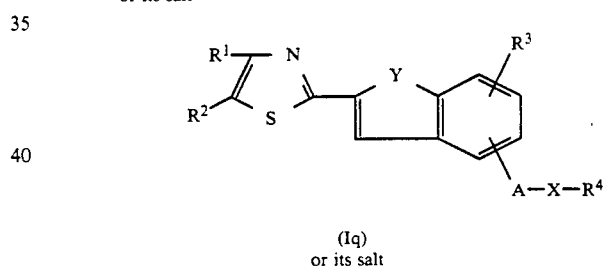
(Iq) or its salt
Process 10
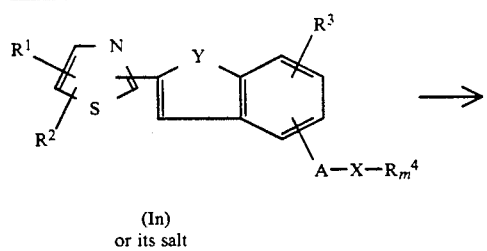
(In) or its salt
Process 13
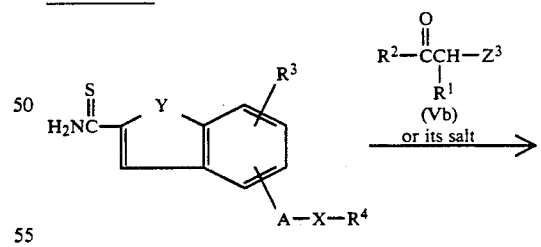
(IV) or its salt
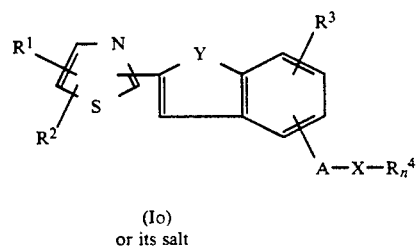
(Io) or its salt
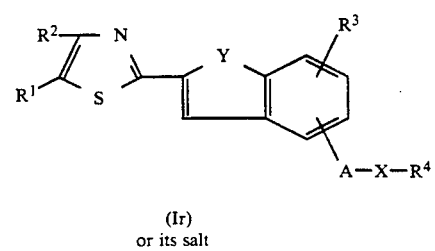
(Ir) or its salt
Process 11

-continued
Process 14
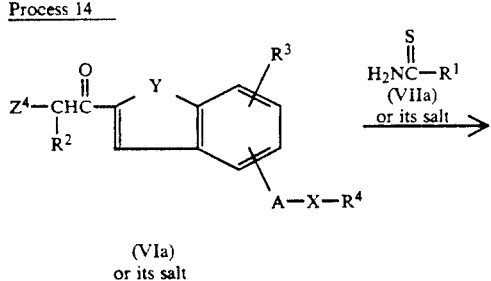
(VIa) or its salt
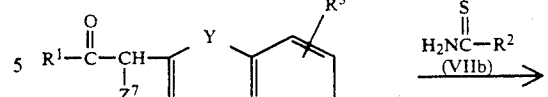
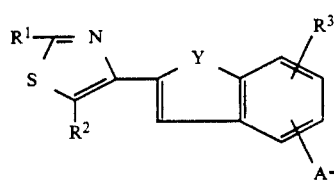
(Is) or its salt
Process 15
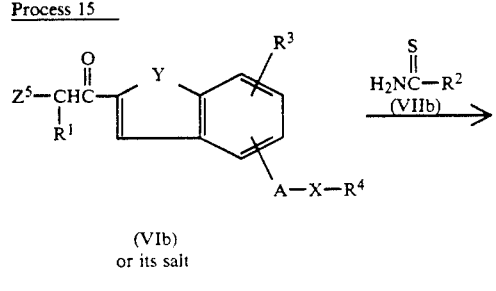
(VIb) or its salt
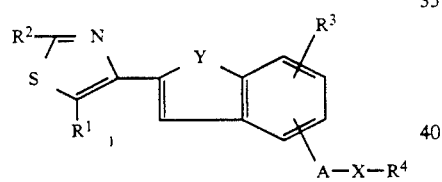
(It) or its salt
Process 16
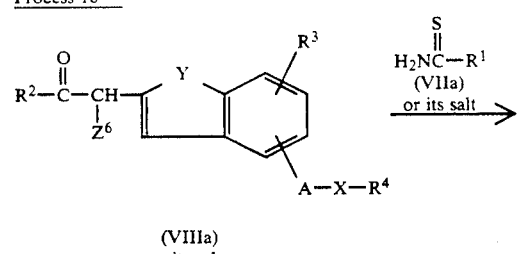
(VIIIa) or its salt
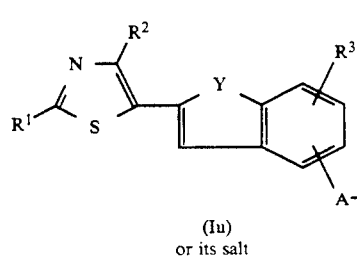
(Iu) or its salt
Process 17
-continued
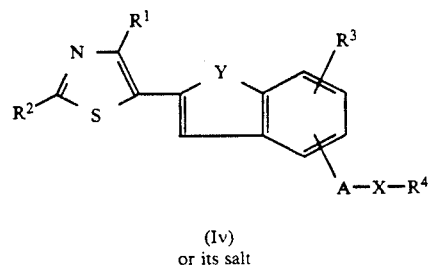
(VIIIb) or its salt
(Iv) or its salt
Process 18
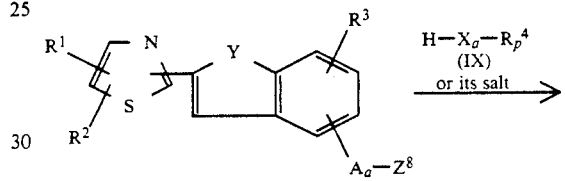
(Iw) or its salt
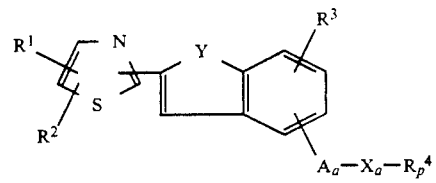
(Ix) or its salt
Process 19
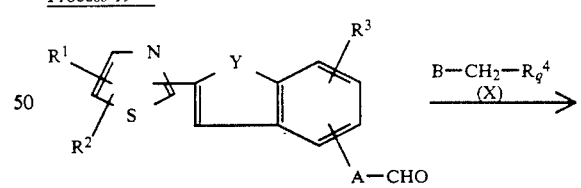
(Iy) or its salt
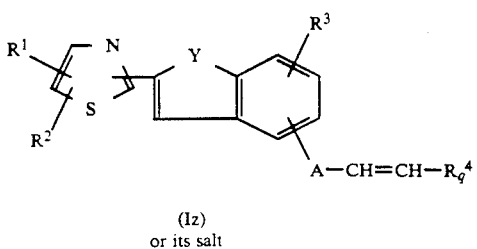
(Iz) or its salt
Process 20

-continued
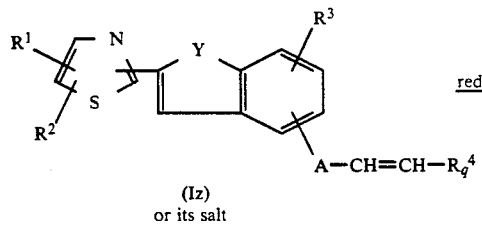
(Iz)
or its salt
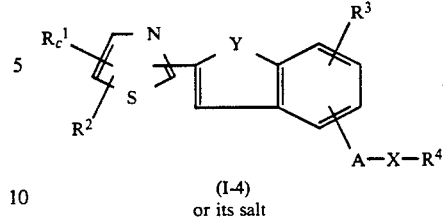
(I-4)
or its salt
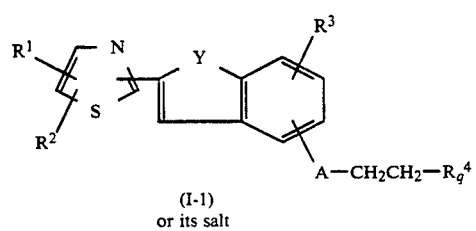
(I-1)
or its salt
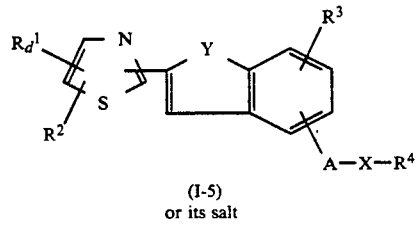
(I-5)
or its salt
Process 21
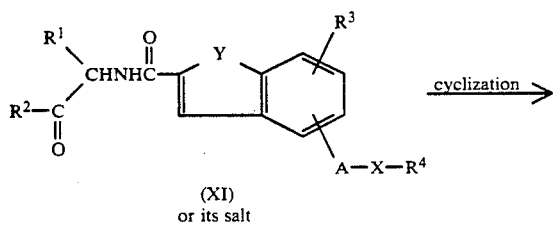
(XI)
or its salt
Process 24
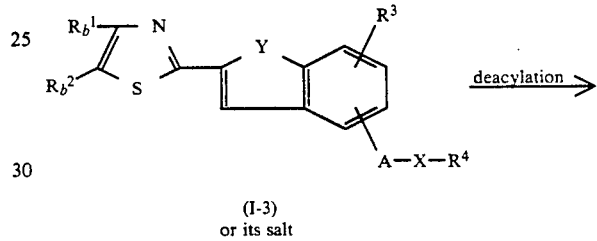
(I-3)
or its salt
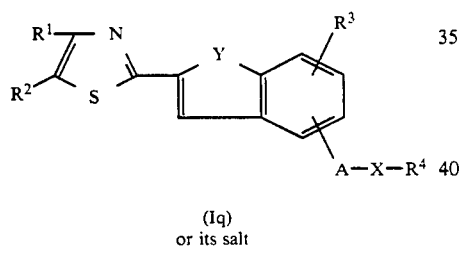
(Iq)
or its salt
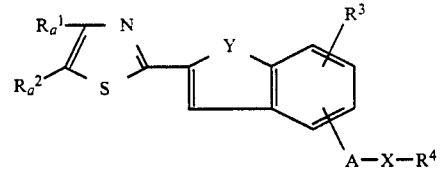
(I-2)
or its salt
Process 22
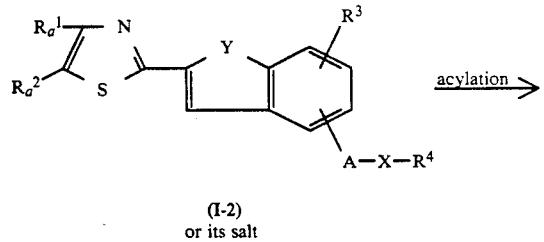
(I-2)
or its salt
Process 25
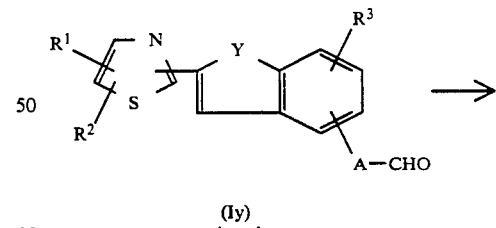
(Iy)
or its salt
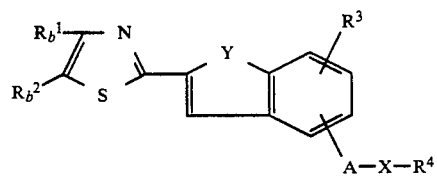
(I-3)
or its salt
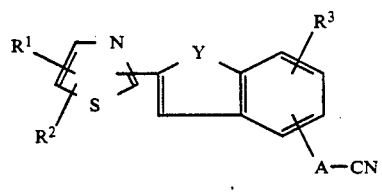
(I-6)
or its salt
Process 23
Process 26

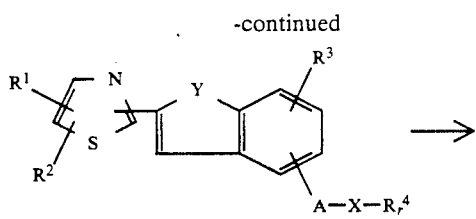

(I-7)
or its salt

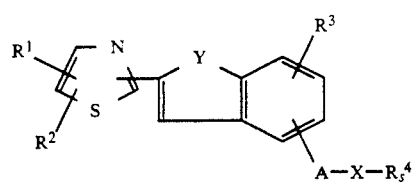

(I-8)
or its salt

Process 27

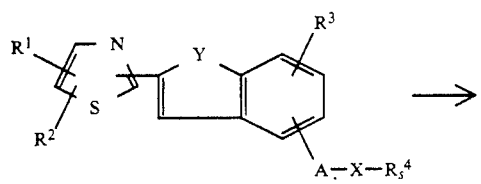

(I-8)
or its salt

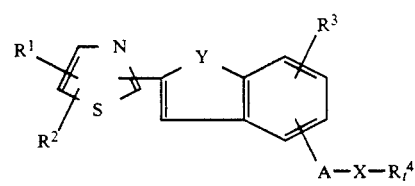

(I-9)
or its salt

Process 28

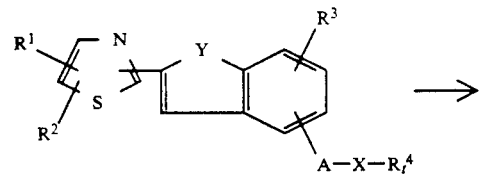

(I-9)
or its salt

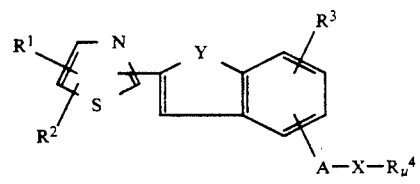

(I-10)
or its salt

Process 29

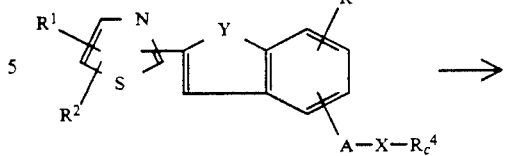

(Id)
or its salt

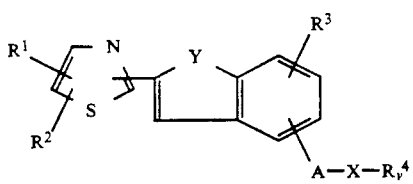

(I-11)
or its salt

Process 30

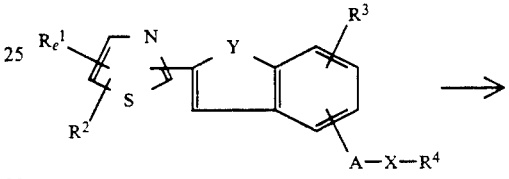

(I-12)
or its salt

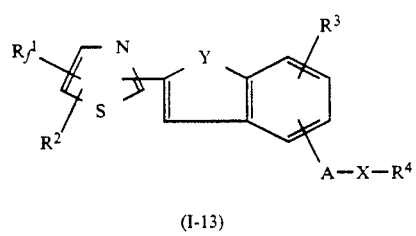

(I-13)
or its salt wherein
$R^1$, $R^2$, $R^3$, $R^4$, A, X and Y are each as defined above,
$R_a^4$ is lower alkyl which may be substituted with substituent(s) selected from the group consisting of halogen, hydroxy, lower alkylsulfonyloxy, arylsulfonyloxy, acyl, acyl(lower)alkylthio and aryl optionally substituted with halo(lower)alkyl, cyano(lower)alkyl, heterocyclic(lower)alkyl, cyano, acyl, acyl(lower)alkyl, a heterocyclic group or (lower alkylsulfinyl)(lower alkylthio)lower alkenyl,
$X_a$ is O or S,
$Z^1$ is acid residue,
$R_b^4$ is aryl substituted with halo(lower)alkyl, or lower alkyl substituted with halogen or aryl which is substituted with halogen or halo(lower)alkyl,
$R_c^4$ is aryl substituted with cyano(lower)alkyl, or lower alkyl substituted with cyano or aryl which is substituted with cyano or cyano(lower)alkyl,
$R_d^4$ is aryl substituted with cyano(lower)alkyl, or lower alkyl substituted with aryl which is substituted with cyano or cyano(lower)alkyl,
$R_e^4$ aryl substituted with tetrazolyl(lower)alkyl, or lower alkyl substituted with aryl which is substituted with tetrazolyl or tetrazolyl(lower)alkyl, $R_f^4$ is lower alkyl substituted with esterified carboxy, esterified carboxy(lower)alkylthio and lower alkylcarbamoyl(lower)alkylthio, esterified carboxy(lower)alkylthio or aryl which is substituted with esterified carboxy or esterified carboxy(lower)alkyl, $R_g^4$ is lower alkyl substituted with carboxy, carboxy(lower)alkylthio and lower alkylcarbamoyl(lower)alkylthio, carboxy(lower)alkylthio or aryl which is substituted with carboxy or carboxy(lower)alkyl, $R_h^4$ is lower alkyl substituted with carboxy or aryl which is substituted with carboxy or carboxy(lower)alkyl, $R_i^4$ is lower alkyl substituted with carbamoyl which may be substituted with lower alkyl, arylsulfonyl or a heterocyclic group or aryl substituted with carbamoyl or carbamoyl(lower)alkyl, each carbamoyl of which may be substituted with lower alkyl, arylsulfonyl or a heterocyclic group, $R_j^4$ is formyl or lower alkyl substituted with formyl, $R_k^4$ is lower alkyl substituted with bis-acyl(lower)alkylthio, $R_l^4$ is lower alkanoyl; lower alkyl substituted with carboxy, esterified carboxy or lower alkanoyl; or aryl substituted with carboxy, esterified carboxy or lower alkanoyl;

$R_m^4$ is lower alkyl substituted with hydroxy, or aryl substituted with hydroxy(lower)alkyl, $R_n^4$ is lower alkyl substituted with halogen, lower alkylsulfonyloxy or arylsulfonyloxy, or aryl substituted with halo(lower)alkyl, $R_o^4$ is lower alkyl substituted with esterified carboxy, or aryl substituted with esterified carboxy(lower)alkyl, $Z^2$ is acid residue, $Z^3$ is acid residue, $Z^4$ is acid residue, $Z^5$ is acid residue, $Z^6$ is acid residue, $Z^7$ is acid residue, $R_p^4$ is aryl optionally substituted with acyl, $A_a$ is lower alkylene, $Z^8$ is acid residue, $R_q^4$ is aryl optionally substituted with esterified carboxy, B is carboxy, esterified carboxy, di-esterified phosphono or substituted phosphonium salt, $R_a^1$ and $R_a^2$ are taken together with adjacent atoms to form an N-containing heterocyclic group, $R_b^1$ and $R_b^2$ are taken together with adjacent atoms to form an N-containing heterocyclic group, N-atom of which is substituted with acyl, $R_c^1$ is lower alkyl substituted with mono(lower alkyl)amino, $R_d^1$ is lower alkyl substituted with lower alkyl(acyl)amino, $R_r^4$ is aryl substituted with halomethyl, $R_s^4$ is aryl substituted with formyl, $R_t^4$ is aryl substituted with 2-(lower alkylsulfinyl)-2-(lower alkylthio)ethenyl, $R_u^4$ is aryl substituted with carboxymethyl, $R_v^4$ is aryl substituted with carboxy(lower)alkyl, or lower alkyl substituted with carboxy or aryl which is substituted with carboxy or carboxy(lower)alkyl, $R_e^1$ is lower alkyl substituted with halogen, and $R_f^1$ is lower alkyl substituted with lower alkylamino.

In the above and subsequent description of the present specification, suitable examples of the various definitions to be included within the scope of the invention are explained in detail in the following.

The term "lower" is intended to mean a group having 1 to 6 carbon atom(s), unless otherwise provided.

Suitable "lower alkyl" and lower alkyl moiety in the terms "acyl(lower)alkylthio", "halo(lower)alkyl", "cyano(lower)alkyl", "heterocyclic(lower)alkyl", "tetrazolyl(lower)alkyl", "esterified carboxy(lower)alkylthio", "lower alkylcarbamoyl(lower)alkylthio", "carboxy(lower)alkylthio", "bis-acyl(lower)alkylthio", "lower alkylamino", "lower alkyl(acyl)amino", "hydroxy(lower)alkyl", "acyl(lower)alkyl", "lower alkylsulfinyl", "lower alkylthio" and "lower alkylsulfonyloxy" may be straight or branched one such as methyl, ethyl, propyl, isopropyl, butyl, isobutyl, tert-butyl, pentyl, hexyl or the like, in which preferable one is $C_1$–$C_4$ lower alkyl such as methyl, ethyl, propyl, isobutyl or tert-butyl.

Suitable "aryl" and aryl moiety in the terms "arylsulfonyl" and "arylsulfonyloxy" may be phenyl, naphthyl, phenyl substituted with lower alkyl [e.g. tolyl, xylyl, mesityl, cumenyl, di(tert-butyl)phenyl, etc.] and the like, in which preferable one is phenyl or tolyl.

Suitable "halogen" may be fluorine, chlorine, bromine and iodine, in which preferable one is fluorine, chlorine or bromine.

Suitable "lower alkoxy" may be methoxy, ethoxy, propoxy, isopropoxy, butoxy and the like, in which preferable one is methoxy.

Suitable "lower alkylamino" may be mono or di(lower alkyl)amino such as methylamino, ethylamino, propylamino, isopropylamino, butylamino, tert-butylamino, isobutylamino, pentylamino, hexylamino, dimethylamino, diethylamino, dipropylamino, dibutylamino, diisopropylamino, dipentylamino, dihexylamino, N-methylethylamino or the like, in which preferable one is tert-butylamino.

Suitable lower alkylamino moiety in the term "lower alkyl(acyl)amino" may be one mentioned-above as mono(lower alkyl)amino.

Suitable "cyclo(lower)alkyl" may be cyclopropyl, cyclobutyl, cyclopentyl and cyclohexyl, in which preferable one is cyclopropyl or cyclobutyl.

Suitable "tricycloalkyl" may be ($C_7$–$C_{12}$)tricycloalkyl, in which preferable one is adamantly.

Suitable lower alkenyl moiety in the term "(lower alkylsulfinyl)(lower alkylthio)lower alkenyl" may be a straight or branched one such as ethenyl, propenyl, pentenyl, isopropenyl, butenyl, hexenyl or the like, in which preferable one is ethenyl.

Suitable "lower alkylene" may be a straight or branched one such as methylene, ethylene, trimethylene, propylene, tetramethylene, pentamethylene, hexamethylene, ethylethylene or the like.

Suitable "lower alkenylene" may be a straight or branched one such as vinylene, propenylene, pentenylene, butenylene or the like.

Suitable "cycloalken ring" which $R^1$ and $R^2$ are taken together with the adjacent atoms to form, may be cyclopenten, cyclohexen, cyclohepten and the like, in which preferable one is cyclohexen.

Suitable "an N-containing heterocyclic group", which $R^1$ and $R^2$ are taken together with the adjacent atoms to form, may be pyrrole, pyrrolidine, azepine, dihydroazepine, tetrahydroazepine and the like, in which preferable one is tetrahydroazepine.

Preferred "lower alkyl substituted with halogen" for $R^1$ may be chloromethyl or trifluoromethyl.

Suitable "acid residue" may be halogen [e.g. fluoro, chloro, bromo, iodo], arenesulfonyloxy [e.g. benzenesulfonyloxy, tosyloxy, etc.], alkanesulfonyloxy [e.g. mesyloxy, ethanesulfonyloxy, etc.], and the like, in which preferable one is halogen.

Suitable "heterocyclic group" and heterocyclic moiety in the term "heterocyclic(lower)alkyl" may be one containing at least one hetero atom selected from nitrogen, sulfur and oxygen atom, and may include saturated or unsaturated, monocyclic or polycyclic heterocyclic group, and preferable heterocyclic group may be N-containing heterocyclic group such as unsaturated 3 to 6 membered heteromonocyclic group containing 1 to 4 nitrogen atoms, for example, pyrrolyl, pyrrolinyl, imidazolyl, pyrazolyl, pyridyl, pyrimidinyl, pyrazinyl, pyridazinyl, triazolyl [e.g. 4H-1,2,4-triazolyl, 1H-1,2,3-triazolyl, 2H-1,2,3-triazolyl, etc.], tetrazolyl [e.g. 1H-tetrazolyl, 2H-tetrazolyl, etc.], etc.;

saturated 3 to 6-membered heteromonocyclic group containing 1 to 4 nitrogen atoms [e.g. pyrrolidinyl, imidazolidinyl, piperidino, piperazinyl, etc.];

unsaturated condensed heterocyclic group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl [e.g. tetrazolo[1,5-b]pyridazinyl, etc.], etc.;

unsaturated 3 to 6-membered heteromonocyclic group containing an oxygen atom, for example, pyranyl, furyl, etc.;

unsaturated, 3 to 6-membered heteromonocyclic group containing 1 to 2 sulfur atoms, for example, thienyl, etc.;

unsaturated 3 to 6-membered heteromonocyclic group containing 1 to 2 oxygen atoms and 1 to 3 nitrogen atoms, for example, oxazolyl, isoxazolyl, oxadiazolyl [e.g. 1,2,4-oxadiazolyl, 1,3,4-oxadiazolyl, 1,2,5-oxadiazolyl, etc.], etc.;

saturated 3 to 6-membered heteromonocyclic group containing 1 to 2 oxygen atoms and 1 to 3 nitrogen atoms [e.g. morpholinyl, etc.];

unsaturated condensed heterocyclic group containing 1 to 2 oxygen atoms and 1 to 3 nitrogen atoms [e.g. benzoxazolyl, benzoxadiazolyl, etc.];

unsaturated 3 to 6-membered heteromonocyclic group containing 1 to 2 sulfur atoms and 1 to 3 nitrogen atoms, for example, thiazolyl, thiadiazolyl [e.g., 1,2,4-thiadiazolyl, 1,3,4-thiadiazolyl, 1,2,5-thiadiazolyl, etc.], etc.;

saturated 3 to 6-membered heteromonocyclic group containing 1 to 2 sulfur atoms and 1 to 3 nitrogen atoms [e.g., thiazolidinyl, etc.];

unsaturated condensed heterocyclic group containing 1 to 2 sulfur atoms and 1 to 3 nitrogen atoms [e.g., benzothiazolyl, benzothiadiazolyl, etc.] and the like.

Preferable one in said heterocyclic group is tetrazolyl, pyridyl or thienyl.

Suitable "acyl" and acyl moiety in the terms "lower alkyl(acyl)amino", "acyl(lower)alkyl" and "acyl(lower)alkylthio" may be carboxy; esterified carboxy; carbamoyl optionally substituted with lower alkyl, arylsulfonyl, lower alkylsulfonyl or a heterocyclic group; lower alkanoyl; aroyl; a heterocycliccarbonyl and the like.

The esterified carboxy may be substituted or unsubstituted lower alkoxycarbonyl [e.g. methoxycarbonyl, ethoxycarbonyl, propoxycarbonyl, butoxycarbonyl, hexyloxycarbonyl, 2-iodoethoxycarbonyl, 2,2,2-trichloroethoxycarbonyl, etc.], substituted or unsubstituted aryloxycarbonyl [e.g. phenoxycarbonyl, 4-nitrophenoxycarbonyl, 2-naphthyloxycarbonyl, etc.], substituted or unsubstituted ar(lower)alkoxycarbonyl [e.g. benzyloxycarbonyl, phenethyloxycarbonyl, benzhydryloxycarbonyl, 4-nitrobenzyloxycarbonyl, etc.] and the like, in which preferable one is unsubstituted lower alkoxycarbonyl.

The carbamoyl substituted with lower alkyl may be methylcarbamoyl, ethylcarbamoyl, propylcarbamoyl, dimethylcarbamoyl, diethylcarbamoyl, N-methyl-N-ethylcarbamoyl and the like, in which preferable one is dimethylcarbamoyl.

The carbamoyl substituted with arylsulfonyl may be phenylsulfonylcarbamoyl, tolylsulfonylcarbamoyl and the like.

The carbamoyl substituted with lower alkylsulfonyl may be methylsulfonylcarbamoyl, ethylsulfonylcarbamoyl and the like.

The carbamoyl substituted with a heterocyclic group may be one substituted with a heterocyclic group as mentioned above, in which preferable one is tetrazolylcarbamoyl.

The lower alkanoyl may be substituted or unsubstituted one such as formyl, acetyl, propionyl, butyryl, isobutyryl, valeryl, isovaleryl, pivaloyl, hexanoyl, trifluoroacetyl or the like, in which preferable one is formyl.

The aroyl may be benzoyl, naphthoyl, toluoyl, di(-tert-butyl)benzoyl and the like.

The heterocyclic moiety in the term "a heterocycliccarbonyl" may be one mentioned above as a heterocyclic group.

The substituent(s) on lower alkyl for $R^4$ may be plural and in such case the substituents may be the same or different.

The acyl(lower)alkylthio moiety in the term "lower alkyl substituted with bis-acyl(lower)alkylthio" for $R_k^4$ may be the same or different one.

Preferred compound (I) is one which has lower alkyl or aryl (more preferably phenyl) for $R^1$, hydrogen for $R^2$, hydrogen, halogen, hydroxy, lower alkyl or lower alkoxy for $R^3$, hydrogen; acyl; or lower alkyl which may be substituted with substituent(s) selected from the group consisting of halogen, hydroxy, lower alkylsulfonyloxy, arylsulfonyloxy, acyl, acyl(lower)alkylthio and aryl (more preferably phenyl) optionally substituted with halo(lower)alkyl, cyano(lower)alkyl, heterocyclic (more preferably tetrazolyl)(lower)alkyl, cyano, acyl or a heterocyclic group (more preferably tetrazolyl) for $R^4$, a single bond for A, a single bond or O for X and O for Y; or lower alkyl or aryl (more preferably phenyl) for $R^1$, hydrogen for $R^2$, hydrogen, halogen, hydroxy, lower alkyl or lower alkoxy for $R^3$, lower alkyl substituted with aryl (more preferably phenyl) which is substituted with acyl(lower)alkyl for $R^4$, a single bond for A, a single bond or O for X and O for Y.

More preferable compound (I) is one which has lower alkyl for $R^1$, hydrogen for $R^2$, hydrogen for $R^3$, lower alkyl substituted with aryl(more preferably phenyl) which is substituted with tetrazolyl(lower)alkyl, acyl(lower)alkyl or tetrazolyl for $R^4$, a single bond for A, O for X and O for Y.

Suitable pharmaceutically acceptable salts of the object compound (I) are conventional non-toxic salts and include an acid addition salt such as an inorganic acid addition salt [e.g. hydrochloride, hydrobromide, sulfate, phosphate, etc.], an organic acid addition salt [e.g. formate, acetate, trifluoroacetate, maleate, tartrate, methanesulfonate, benzenesulfonate, toluenesulfonate, etc.], a metal salt such as an alkali metal salt [e.g. sodium salt, potassium salt, etc.] and an alkaline earth metal salt [e.g. calcium salt, magnesium salt, etc.] and the like.

The processes for preparing the object compound (I) are explained in detail in the following.

Process 1

The object compound (I) or its salt can be prepared by subjecting a compound (II) or its salt to cyclization reaction.

Suitable salt of the compound (II) may be the same as those exemplified for the compound (I).

This reaction is preferably carried out in the presence of a dehydrating agent [e.g. acetic anhydride, etc.] or a base such as alkali metal [e.g. lithium, sodium, potassium, etc.], alkaline earth metal [e.g. calcium, magnesium, etc.], alkali metal hydride [e.g. sodium hydride, etc.], alkaline earth metal hydride [e.g. calcium hydride, etc.], alkali metal alkoxide [e.g. sodium methoxide, sodium ethoxide, potassium tert-butoxide, etc.], alkaline earth metal alkoxide [e.g. magnesium methoxide, magnesium ethoxide, etc.], trialkylamine [e.g. trimethylamine, triethylamine, etc.], picoline, 1,5-diazabicyclo[4.3.0]non-5-ene, 1,4-diazabicyclo[2.2.2]octane, 1,8-diazabicyclo[5.4.0]undec-7-ene, or the like.

The reaction is usually carried out in a conventional solvent such as dioxane, tetrahydrofuran, pyridine, aromatic hydrocarbon [e.g. benzene, toluene, xylene, etc.] or any other organic solvent which does not adversely influence the reaction.

The reaction temperature is not critical, and the reaction is usually carried out under cooling to hating.

Process 2

The object compound (Ib) or its salt can be prepared by subjecting a compound (Ia) or its salt to dealkylation reaction.

Suitable salts of the compounds (Ia) and (Ib) may be the same as those exemplified for the compound (I).

The reaction is carried out in accordance with a conventional method such as hydrolysis, reduction or the like.

The hydrolysis is preferably carried out in the presence of an acid including Lewis acid [e.g. hydrochloric acid, hydrobromic acid, hydroiodic acid, boron tribromide, boron trichloride, etc.] or tri(lower alkyl)silyliodide [e.g. trimethylsilyliodide, etc.].

The reaction is usually carried out in a solvent such as water, acetic acid, methylene chloride, tetrahydrofuran, a mixture thereof or any solvent which does not adversely influence the reaction.

The reaction temperature is not critical and the reaction is usually carried out under cooling to heating.

The reduction can be applied preferably for elimination of methyl substituted with substituted- or unsubstituted-aryl.

This reduction method is usually carried out in a catalyst.

Suitable catalysts to be used in catalytic reduction are conventional ones such as platinum catalyst [e.g. platinum plate, spongy platinum, platinum black, colloidal platinum, platinum oxide, platinum wire, etc.], palladium catalyst [e.g. spongy palladium, palladium black, palladium oxide, palladium on carbon, colloidal palladium, palladium on barium sulfate, palladium on barium carbonate, etc.], nickel catalyst [e.g. reduced nickel, nickel oxide, Raney nickel, etc.], cobalt catalyst [e.g. reduced cobalt, Raney cobalt, etc.], iron catalyst [e.g. reduced iron, Raney iron, etc.], copper catalyst [e.g. reduced copper, Raney copper, Ullman copper, etc.] or the like.

The reaction is usually carried out in a conventional solvent such as water, an alcohol [e.g. methanol, ethanol, propanol, etc.], N,N-dimethylformamide, diethyl ether, dioxane, tetrahydrofuran or any other organic solvent which does not adversely influence the reaction.

The reaction temperature of this reduction is not critical and the reaction is usually carried out under cooling to warming.

Process 3

The object compound (Ia) or its salt can be prepared by reacting a compound (Ib) or its salt with a compound (III).

When the compound (III) having halogen for $Z^1$ is used in this reaction, the reaction is preferably carried out in the presence of a base such as alkali metal [e.g. lithium, sodium, potassium, etc.], the hydroxide or carbonate or bicarbonate thereof [e.g. sodium hydroxide, potassium carbonate, potassium bicarbonate, etc.], alkaline earth metal [e.g. calcium, magnesium, etc.], alkali metal hydride [e.g. sodium hydride, etc.], alkaline earth metal hydride [e.g. calcium hydride, etc.], alkali metal alkoxide [e.g. sodium methoxide, sodium ethoxide, potassium tert-butoxide, etc.], alkaline earth metal alkoxide [e.g. magnesium methoxide, magnesium ethoxide, etc.] or the like, or alkali metal iodide [e.g. sodium iodide, potassium iodide, etc.] and said base.

This reaction is usually carried out in a conventional solvent such as tetrahydrofuran, dioxane, N,N-dimethylformamide, acetone, a mixture thereof, or any other solvent which does not adversely influence the reaction. Additionally, in case that the compound (III) is in liquid, it can also be used as a solvent.

The reaction temperature is not critical, and the reaction is usually carried out under cooling to heating.

Process 4

The object compound (Id) or its salt can be prepared by reacting a compound (Ic) or its salt with a cyanide compound.

Suitable salts of the compounds (Ic) and (Id) may be the same as those exemplified for the compound (I).

Suitable cyanide compound may be a metallic cyanide such as alkali metal cyanide [e.g. sodium cyanide, potassium cyanide, etc.], cuprous cyanide or the like.

This reaction is preferably carried out in the presence of alkali metal iodide [e.g. sodium iodide, potassium iodide, etc.], phase transfer catalyst [e.g. Adogen 464 [Trademark: Aldrich), etc.], and the like.

The reaction is usually carried out in a conventional solvent such as water, an alcohol [e.g. methanol, ethanol, etc.], pyridine, quinoline, N,N-dimethylformamide, a mixture thereof or any other solvent which does not adversely influence the reaction.

The reaction temperature is not critical, and the reaction is usually carried out under warming to heating.

Process 5

The object compound (If) or its salt can be prepared by reacting a compound (Ie) or its salt with an azide compound.

Suitable salts of the compounds (Ie) and (If) may be the same as those exemplified for the compound (I).

Suitable azide compound may be alkali metal azide [e.g. sodium azide, potassium azide, etc.], alkaline earth metal azide [e.g. calcium azide, etc.], aluminum azide, hydrogen azide and the like.

The reaction is preferably carried out in the presence of ammonium halide [e.g. ammonium chloride, ammonium bromide, etc.], lower alkylammonium halide [e.g. trimethylammonium chloride, triethylammonium chloride, etc.] and the like.

The reaction is usually carried out in a conventional solvent such as tetrahydrofuran, dioxane, N,N-dimethylformamide or any other organic solvent which does not adversely influence the reaction.

The reaction temperature is not critical, and the reaction can be carried out under warming to heating.

Process 6

The object compound (Ih) or its salt can be prepared by subjecting a compound (Ig) or its salt to deesterification reaction.

Suitable salts of the compounds (Ig) and (Ih) may be the same as those exemplified for the compound (I).

The reaction is carried out in accordance with a conventional method such as hydrolysis, reduction or the like.

The hydrolysis is preferably carried out in the presence of a base or an acid including Lewis acid. Suitable base may include an inorganic base and an organic base such as an alkali metal [e.g. lithium, sodium, potassium, etc.], an alkaline earth metal [e.g. magnesium, calcium, etc.], the hydroxide or carbonate or bicarbonate thereof, trialkylamine [e.g. trimethylamine, triethylamine, etc.], picoline, 1,5-diazabicyclo[4.3.0]-non-5-ene, 1,4-diazabicyclo[2.2.2]octane, 1,8-diazabicyclo[5.4.0]undec-7-ene, or the like. Suitable acid may include an organic acid [e.g. formic acid, acetic acid, propionic acid, trichloroacetic acid, trifluoroacetic acid, etc.], an inorganic acid [e.g. hydrochloric acid, hydrobromic acid, hydroiodic acid, sulfuric acid, etc.] and Lewis acid [e.g. boron tribromide, etc.].

The reaction is usually carried out in a solvent such as water, an alcohol [e.g. methanol, ethanol, etc.], xylene, diethylene glycol monomethyl ether, methylene chloride, tetrahydrofuran, a mixture thereof or any other solvent which does not adversely influence the reaction. A liquid base or acid can be also used as the solvent. The reaction temperature is not critical and the reaction is usually carried out under cooling to warming.

In this reaction, in case that the compound (Ig) having lower alkyl substituted with two esterified carboxy or aryl substituted with di(esterified carboxy)(lower)alkyl for $R_g^4$ is used as a starting compound, the compound (Ih) having lower alkyl substituted with one carboxy or aryl substituted with mono(carboxy)(lower)alkyl for $R_g^4$ may be obtained according to reaction conditions. This case is included within the scope of the present reaction.

The reduction can be applied preferably for elimination of the ester moiety such as 4-nitrobenzyl, 2-iodoethyl, 2,2,2-trichloroethyl, or the like. The reduction method applicable for the elimination reaction may include chemical reduction and catalytic reduction.

Suitable reducing agents to be used in chemical reduction are a combination of metal [e.g. tin, zinc, iron, etc.] or metallic compound [e.g. chromium chloride, chromium acetate, etc.] and an organic or inorganic acid [e.g. formic acid, acetic acid, propionic acid, trifluoroacetic acid, p-toluenesulfonic acid, hydrochloric acid, hydrobromic acid, etc.].

Suitable catalysts to be used in catalytic reduction are conventional ones such as platinum catalyst [e.g. platinum plate, spongy platinum, platinum black, colloidal platinum, platinum oxide, platinum wire, etc.], palladium catalyst [e.g. spongy palladium, palladium black, palladium oxide, palladium on carbon, colloidal palladium, palladium on barium sulfate, palladium on barium carbonate, etc.], nickel catalyst [e.g. reduced nickel, nickel oxide, Raney nickel, etc.], cobalt catalyst [e.g. reduced cobalt, Raney cobalt, etc.], iron catalyst [e.g. reduced iron, Raney iron, etc.], copper catalyst [e.g. reduced copper, Raney copper, Ullman copper, etc.] or the like.

The reduction is usually carried out in a conventional solvent which does not adversely influence the reaction such as water, an alcohol [e.g. methanol, ethanol, propanol, etc.], N,N-dimethylformamide, or a mixture thereof. Additionally, in case that the above-mentioned acids to be used in chemical reduction are in liquid, they can also be used as a solvent. Further, a suitable solvent to be used in catalytic reduction may be the above-mentioned solvent, and other conventional solvent such as diethyl ether, dioxane, tetrahydrofuran, etc., or a mixture thereof.

The reaction temperature of this reduction is not critical and the reaction is usually carried out under cooling to warming.

Process 7

The object compound (Ij) or its salt can be prepared by reacting a compound (Ii) or its reactive derivative at the carboxy group or a salt thereof with an amine.

Suitable salts of the compounds (Ii) and (Ij) and its reactive derivative at the carboxy group may be the same as those exemplified for the compound (I).

Suitable amine may be ammonia, arenesulfonamide, amine substituted with a heterocyclic group.

The arenesulfonamide may be benzenesulfonamide, methylbenzenesulfonamide, ethylbenzenesulfonamide, naphthalenesulfonamide and the like, in which preferable one is methylbenzenesulfonamide.

The amine substituted with a heterocyclic group may be one substituted with a heterocyclic group as mentioned above such as aminothiazole, aminothiadiazole, aminotriazole, aminotetrazole or the like, in which preferable one is aminotetrazole.

Suitable reaction derivative at the carboxy group of the compound (Ii) may include an ester, an acid halide, an acid anhydride and the like. The suitable examples of the reactive derivatives may be an acid halide [e.g. acid chloride, acid bromide, etc.]; a symmetrical acid anhydride; a mixed acid anhydride with 1,1'-carbonyl diimidazole or an acid such as aliphatic carboxylic acid [e.g. acetic acid, pivalic acid, etc.], substituted phosphoric acid [e.g. dialkylphosphoric acid, diphenylphosphoric acid, etc.]; an ester such as lower alkyl ester [e.g. methyl ester, ethyl ester, propyl ester, hexyl ester, etc.], substituted or unsubstituted ar(lower)alkyl ester [e.g. benzyl ester, benzhydryl ester, p-chlorobenzyl ester, etc.], substituted or unsubstituted aryl ester [e.g. phenyl ester, tolyl ester, 4-nitrophenyl ester, 2,4-dinitrophenyl ester, pentachlorophenyl ester, naphthyl ester, etc.], or an ester with N,N-dimethylhydroxylamine, N-hydroxysuccinimide, N-hydroxyphthalimide or 1-hydroxy-6-chloro-1H-benzotriazole, or the like.

The reaction is usually carried out in a conventional solvent such as water, acetone, dioxane, chloroform, methylene chloride, ethylene chloride, tetrahydrofuran, ethyl acetate, N,N-dimethylformamide, pyridine or any other organic solvent which does not adversely influence the reaction. Among these solvents, hydrophilic solvents may be used in a mixture with water.

When the compound (Ii) is used in a free acid form in the reaction, the reaction is preferably carried out in the presence of a conventional condensing agent such as N,N'-dicyclohexylcarbodiimide, N-cyclohexyl-N'-morpholinoethylcarbodiimide, N-ethyl-N'-(3-dimethylaminopropyl)carbodiimide, thionyl chloride, oxalyl chloride, lower alkoxycarbonyl halide [e.g. ethyl chloroformate, isobutyl chloroformate, etc.], 1-(p-chlorobenzenesulfonyloxy)-6-chloro-1H-benzotirazole, or the like. The reaction is also preferably carried out in the presence of a conventional base such as triethylamine, pyridine, sodium hydroxide or the like.

The reaction temperature is not critical, and the reaction can be carried out under cooling to heating.

Process 8

The object compound (Il) or its salt can be prepared by reacting a compound (Ik) or its salt with acyl(lower)alkylthiol.

Suitable salts of the compounds (Ik) and (Il) may be the same as those exemplified for the compound (I).

Suitable acyl(lower)alkylthiol may be mercapto(lower)alkanoic acid [e.g. mercaptoacetic acid, mercaptopropionic acid, mercaptobutyric acid, mercaptopentanoic acid, etc.]; mercapto(lower)alkanoic acid ester [e.g. methyl mercaptoacetate, ethyl mercaptoacetate, methyl mercaptopropionate, methyl mercaptobutyrate, etc.]; mercapto(lower)alkanamide optionally substituted with lower alkyl, arylsulfonyl or a heterocyclic group [e.g. mercaptoacetamide, mercaptopropionamide, N,N-dimethyl-mercaptopropionamide, etc.]; a mixture thereof; and the like, which preferable one is methyl mercaptobutyrate, N,N-dimethyl-mercaptopropionamide or a mixture thereof.

This reaction is carried out in the presence of boron trihalide [e.g. boron trifluoride, boron trichloride, etc.] or its diethyl ether complex.

The reaction is usually carried out in a conventional solvent such as acetonitrile, dioxane, chloroform, methylene chloride, tetrahydrofuran or any other solvent which does not adversely influence the reaction.

The reaction temperature is not critical, and the reaction is usually carried out under cooling.

In this reaction, in case that a mixture of two kind of acyl(lower)alkylthiol is used, the compound (Il) having different acyl(lower)alkylthio in lower alkyl substituted with bis-acyl(lower)alkylthio for $R_k^4$ may be obtained according to reaction conditions. This case is included within the scope of the present reaction.

Process 9

The object compound (In) or its salt can be prepared by reacting a compound (Im) or its salt with a reducing agent.

Suitable salts of the compounds (Im) and (In) may be the same as those exemplified for the compound (I).

Suitable reducing agent may be aluminum hydride compound [e.g. lithium aluminum hydride, lithium tri-t-butoxyaluminum hydride, etc.], borohydride compound [e.g. sodium borohydride, etc.], aluminum alkoxide [e.g. aluminum isopropoxide, etc.] and the like.

The reaction is usually carried out in a conventional solvent, such as water, an alcohol [e.g. methanol, ethanol, propanol, isopropanol, etc.], chloroform, diethyl ether, dioxane, or any other organic solvent which does not adversely influence the reaction, or a mixture thereof.

The reaction temperature is not critical, and the reaction is usually carried out under cooling to heating.

Process 10

The object compound (Io) or its salt can be prepared by reacting a compound (In) or its salt with a halogenating agent or a sulfonylating agent.

Suitable salts of the compounds (In) and (Io) may be the same as those exemplified for the compound (I).

Suitable halogenating agent may be phosphorus trihalide [e.g. phosphorus trichloride, phosphorus tribromide, etc.], phosphorus pentahalide [e.g. phosphorus pentachloride, etc.], thionyl halide [e.g. thionyl chloride, etc.] and the like.

Suitable sulfonylating agent may be lower alkanesulfonyl halide [e.g. methanesulfonyl chloride, ethanesulfonyl chloride, methanesulfonyl bromide, etc.], arenesulfonyl halide [e.g. benzenesulfonyl chloride, toluenesulfonyl chloride, etc.] and the like.

The reaction is usually carried out in a conventional solvent such as carbontetrachloride, chloroform, methylene chloride, diethyl ether, tetrahydrofuran, dioxane or any other solvent which does not adversely influence the reaction.

The reaction temperature is not critical, and the reaction is usually carried out under cooling to heating.

Process 11

The object compound (Ip) or its salt can be prepared by reacting a compound (Io) or its salt with a mixture of lower alkyl substituted with esterified carboxy and a base.

Suitable salts of the compounds (Io) and (Ip) may be the same as those exemplified for the compound (I).

Suitable base may be alkali metal [e.g. lithium, sodium, potassium, etc.], alkaline earth metal [e.g. calcium magnesium, etc.], alkali metal hydride [e.g. sodium hydride, etc.], alkaline earth metal hydride [e.g. calcium hydride, etc.], lower alkyl alkali metal [e.g. n-butyl lithium, etc.], alkali metal lower alkylamide [e.g. lithium diisopropylamide, etc.] and the like.

When a base is alkali metal lower alkylamide, it is preferable to add hexamethylphosphoric triamide into a mixture of lower alkyl substituted with esterified carboxy and a base.

The reaction is usually carried out in a conventional solvent such as diethyl ether, tetrahydrofuran, n-hexane, a mixture thereof, or any other solvent which does not adversely influence the reaction.

The reaction temperature is not critical, and the reaction is usually carried out under cooling to warming.

Process 12

The object compound (Iq) or its salt can be prepared by reacting a compound (IV) or its salt with a compound (Va) or its salt.

Suitable salt of the compound (Iq) may be the same as those exemplified for the compound (I).

Suitable salt of the compound (IV) may be a metal salt as exemplified for the compound (I).

Suitable salt of the compound (Va) may be an acid addition salt as exemplified for the compound (I).

The reaction is usually carried out in a conventional solvent such as an alcohol [e.g. methanol, ethanol, propanol, isopropanol, etc.], aromatic hydrocarbon [e.g.

benzene, toluene, xylene, etc.], acetonitrile, dioxane, chloroform, methylene chloride, N,N-dimethylformamide or any other organic solvent which does not adversely influence the reaction.

The reaction temperature is not critical, and the reaction is usually carried out under cooling to heating.

Process 13

The object compound (Ir) or its salt can be prepared by reacting a compound (IV) or its salt with a compound (Vb) or its salt.

Suitable salt of the compound (Ir) may be the same as those exemplified for the compound (I).

Suitable salt of the compound (Vb) may be an acid addition salt as exemplified for the compound (I).

This reaction can be carried out in substantially the same manner as Process 12, and therefore the reaction mode and reaction condition (e.g. solvent, reaction temperature, etc.) of this reaction are to be referred to those as explained in Process 12.

Process 14

The object compound (Is) or its salt can be prepared by reacting a compound (VIa) or its salt with a compound (VIIa) or its salt.

Suitable salt of the compound (Is) may be the same as those exemplified for the compound (I).

Suitable salt of the compound (VIa) may be a metal salt as exemplified for the compound (I).

Suitable salt of the compound (VIIa) may be an acid addition salt as exemplified for the compound (I).

This reaction can be carried out in substantially the same manner as Process 12, and therefore the reaction mode and reaction condition (e.g. solvent, reaction temperature, etc.) of this reaction are to be referred to those as explained in Process 12.

Process 15

The object compound (It) or its salt can be prepared by reacting a compound (VIb) or its salt with a compound (VIIb).

Suitable salts of the compounds (It) and (VIb) may be the same as those exemplified for the compound (I).

This reaction can be carried out in substantially the same manner as Process 12, and therefore the reaction mode and reaction condition (e.g. solvent, reaction temperature, etc.) of this reaction are to be referred to those as explained in Process 12.

Process 16

The object compound (Iu) or its salt can be prepared by reacting a compound (VIIIa) or its salt with a compound (VIIa) or its salt.

Suitable salt of the compound (Iu) may be the same as those exemplified for the compound (I).

Suitable salt of the compound (VIIIa) may be a metal salt as exemplified for the compound (I).

This reaction can be carried out in substantially the same manner as Process 12, and therefore the reaction mode and reaction condition (e.g. solvent, reaction temperature, etc.) of this reaction are to be referred to those as explained in Process 12.

Process 17

The object compound (Iv) or its salt can be prepared by reacting a compound (VIIIb) or its salt with a compound (VIIb).

Suitable salts of the compounds (Iv) and (VIIIb) may be the same as those exemplified for the compound (I).

This reaction can be carried out in substantially the same manner as Process 12. and therefore the reaction mode and reaction condition (e.g. solvent, reaction temperature, etc.) of this reaction are to be referred to those as explained in Process 12.

Process 18

The object compound (Ix) or its salt can be prepared by reacting a compound (Iw) or its salt with a compound (IX) or its salt.

Suitable salts of the compounds (Iw) and (Ix) may be an acid addition salt as exemplified for the compound (I).

Suitable salt of the compound (IX) may be a metal salt as exemplified for the compound (I).

This reaction can be carried out in substantially the same manner as Process 3, and therefore the reaction mode and reaction condition (e.g. solvent, reaction temperature, etc.) of this reaction are to be referred to those as explained in Process 3.

Process 19

The object compound (Iz) or its salt can be prepared by reacting a compound (Iy) or its salt with a compound (X).

Suitable salts of the compounds (Iy) and (Iz) may be an acid addition salt as exemplified for the compound (I).

This reaction is preferably carried out in the presence of an inorganic or organic base such as an alkali metal [e.g. sodium, potassium, etc.], an alkaline earth metal [e.g. magnesium, calcium, etc.], the hydroxide or carbonate thereof, alkali metal hydride [e.g. sodium hydride, etc.], alkali metal amide [e.g. sodium amide, etc.], alkaline earth metal hydride [e.g. calcium hydride, etc.], alkali metal alkoxide [e.g. sodium methoxide, sodium ethoxide, potassium tert-butoxide, etc.], alkaline earth metal alkoxide [e.g. magnesium methoxide, magnesium ethoxide, etc.], lower alkyl alkali metal [e.g. n-butyl lithium, etc.], trialkylamine [e.g. trimethylamine, triethylamine, etc.], pyridine, piperidine, picoline, 1,5-diazabicyclo[4.3.0]non-5-ene, 1,4-diazabicyclo[2.2.0]octane, 1,8-diazabicyclo[5.4.0]undec-7-ene, or the like.

The reaction is usually carried out in a solvent such as water, an alcohol [e.g. methanol, ethanol, etc.], acetonitrile, chloroform, methylene chloride, nitromethane, benzene, tetrahydrofuran, diethyl ether, N,N-dimethylformamide, dimethylsulfoxide or any other organic solvent which does not adversely influence the reaction.

The reaction temperature is not critical, and the reaction can be carried out under cooling to hating.

Process 20

The object compound (I-1) or its salt can be prepared by subjecting compound (Iz) or its salt to catalytic reduction.

Suitable salt of the compound (I-1) may be an acid addition salt as exemplified for the compound (I).

This catalytic reduction can be carried out in substantially the same manner as one in Process 6, and therefore the reaction mode and reaction condition (e.g. solvent, reaction temperature, etc.) of this reaction are to be referred to those as explained in Process 6.

Process 21

The object compound (Iq) or its salt can be prepared by subjecting a compound (XI) or its salt to cyclization reaction in the presence of a sulfurizing agent.

Suitable salts of the compounds (Iq) and (XI) may be the same as those exemplified for the compound (I).

Suitable sulfurizing agent may be phosphorus pentasulfide, 2,4-bis[4-methoxyphenyl]-1,3-dithia-2,4-diphosphetane-2,4-disulfide and the like.

The reaction is usually carried out in a conventional solvent such as pyridine, dimethoxyethane, toluene or any other organic solvent which does not adversely influence the reaction.

The reaction temperature is not critical, and the reaction is usually carried out under warming or heating.

Process 22

The object compound (I-3) or its salt can be prepared by reacting a compound (I-2) or its salt with an acylating agent.

Suitable salt of the compound (I-2) may be the same as those exemplified for the compound (I).

Suitable salt of the compound (I-3) may be a metal salt as exemplified for the compound (I).

The acylating agent may include an organic acid represented by the formula: $R^5$—OH, in which $R^5$ is acyl as illustrated above, or its reactive derivative.

The suitable reactive derivative of organic acid may be a conventional one such as an acid halide [e.g. acid chloride, acid bromide, etc.], an acid azide, an acid anhydride, an activated amide, an activated ester or the like.

When free acid is used as an acylating agent, the acylation reaction may preferably be conducted in the presence of a conventional condensing agent such as N,N'-dicyclohexylcarbodiimide or the like.

The reaction is usually carried out in a conventional solvent such as water, acetone, dioxane, chloroform, methylene chloride, acetonitrile, ethylene chloride, tetrahydrofuran, ethyl acetate, N,N-dimethylformamide, pyridine or any other organic solvent which does not adversely influence the reaction, or a mixture thereof.

The reaction is also preferably carried out in the presence of a conventional base such as triethylamine, pyridine, sodium hydroxide or the like.

The reaction temperature is not critical, and the reaction can be carried out under cooling to heating.

Process 23

The object compound (I-5) or its salt can be prepared by reacting a compound (I-4) or its salt with an acylating agent.

Suitable salt of the compound (I-4) may be the same as those exemplified for the compound (I).

Suitable salt of the compound (I-5) may be a metal salt as exemplified for the compound (I).

This reaction can be carried out in substantially the same manner as Process 22, and therefore the reaction mode and reaction condition (e.g. solvent, reaction temperature, etc.) of this reaction are to be referred to those as explained in Process 22.

Process 24

The object compound (I-2) or its salt can be prepared by subjecting a compound (I-3) or its salt to deacylation reaction.

The reaction can be carried out in substantially the same manner as hydrolysis in Process 6, and therefore the reaction mode and reaction condition (e.g. solvent, reaction temperature, etc.) of this reaction are to be referred to those as explained in Process 6.

Process 25

The object compound (I-6) or its salt can be prepared by the following method.

Namely, 1) the compound (Iy) or its salt is firstly reacted with hydroxylamine, and then 2) reacting the resultant product with a dehydrating agent.

Suitable salts of the compounds (Iy) and (I-6) may be an acid addition salt as exemplified for the compound (I).

In the first step, the reaction is preferably carried out in the presence of alkali metal salt of acetic acid [e.g. sodium acetate, etc.].

The reaction is usually carried out in a solvent which does not adversely influence the reaction such as tetrahydrofuran, dioxane, acetic acid or the like.

The reaction temperature is not critical and the reaction can be carried out under cooling to heating.

In this reaction, a compound of the formula:

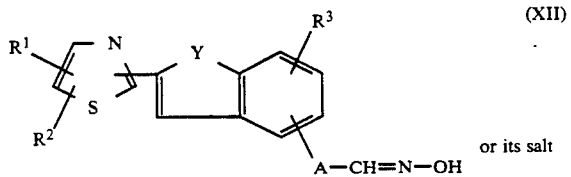

or its salt wherein $R^1$, $R^2$, $R^3$, A and Y are each as defined above, may be obtained.

The compound (XII) or its salt is further reacted with a dehydrating agent to give the object compound (I-6) or its salt.

Suitable dehydrating agent may be phosphorus compound [e.g. phosphorus pentoxide, phosphorus pentachloride, phosphorus oxychloride, etc.], thionyl chloride, acid anhydride [e.g. acetic anhydride, etc.], phosgene, arylsulphonyl chloride [e.g. benzenesulfonyl chloride, p-toluenesulfonyl chloride, etc.], methanesulfonyl chloride, sulfamic acid, ammonium sulfamate, N,N'-dicyclohexylcarbodiimide, lower alkoxycarbonyl halide [e.g. ethyl chloroformate, etc.] and the like.

The reaction is usually carried out in a conventional solvent such as acetonitrile, methylene chloride, ethylene chloride, benzene, N,N-dimethylformamide, pyridine or any other organic solvent which does not adversely influence the reaction.

Additionally in case that the above-mentioned dehydrating agents are in liquid, they can also be used as a solvent.

The reaction temperature is not critical and the reaction is preferably carried out under warming or heating.

Process 26

The object compound (I-8) or its salt can be prepared by reacting a compound (I-7) or its salt with an oxidizing agent.

Suitable salts of the compounds (I-7) and (I-8) may be an acid addition salt as exemplified for the compound (I).

Suitable oxidizing agent may be dimethyl sulfoxide and the like.

This reaction is preferably carried out in the presence of alkali metal iodide [e.g. sodium iodide, etc.] and alkali metal carbonate [e.g. sodium carbonate].

The reaction is usually carried out in a solvent which does not adversely influence the reaction such as dimethoxyethane or the like. Additionally in case that the above-mentioned oxidizing agent is in liquid, it can also be used as a solvent.

The reaction temperature is not critical and the reaction is preferably carried out under warming or heating.

Process 27

The object compound (I-9) or its salt can be prepared by reacting a compound (I-8) or its salt with (lower alkylsulfinyl)(lower alkylthio)methyl.

Suitable salt of the compound (I-9) may be an acid addition salt as exemplified for the compound (I).

The reaction is preferably carried in the presence of a phase transfer catalyst [e.g. Triton B, etc.] and the like.

The reaction is usually carried out in a solvent such as tetrahydrofuran, an alcohol [e.g. methanol, ethanol, etc.] or any other solvent which does not adversely influence the reaction.

The reaction temperature is not critical and the reaction is preferably carried out under warming or heating.

Process 28

The object compound (I-10) or its salt can be prepared by reacting a compound (I-9) or its salt with an acid.

Suitable salt of the compound (I-10) may be an acid addition salt as exemplified for the compound (I).

Suitable acid may be an inorganic acid [e.g. hydrochloric acid, hydrobromic acid, etc.] and an organic acid [e.g. trifluoroacetic acid, methanesulfonic acid, toluenesulfonic acid, etc.].

The reaction is usually carried out in a conventional solvent such as water, an alcohol [e.g. methanol, ethanol, etc.], tetrahydrofuran, dioxane or any other organic solvent which does not adversely influence the reaction, or a mixture thereof.

The reaction temperature is not critical, and the reaction can be carried out cooling to heating.

Process 29

The object compound (I-11) or its salt can be prepared by subjecting a compound (Id) or its salt to hydrolysis.

Suitable salt of the compound (I-11) may be the same as those exemplified for the compound (I).

This hydrolysis can be carried out in substantially the same manner as one in Process 6, and therefore the reaction mode and reaction condition (e.g. solvent, reaction temperature, etc.) of this reaction are to be referred to those as explained in Process 6.

Process 30

The object compound (I-13) or its salt can be prepared by reacting a compound (I-12) or its salt with lower alkylamine.

Suitable salt of the compound (I-12) may be a metal salt as exemplified for the compound (I).

Suitable salt of the compound (I-13) may be the same as those exemplified for the compound (I).

Suitable lower alkylamine may be mono or di(lower alkyl)amine such as methylamine, ethylamine, propylamine, isopropylamine, butylamine, tert-butylamine, isobutylamine, pentylamine, hexylamine, dimethylamine, diethylamine, dipropylamine, dibutylamine, diisopropylamine, dipentylamine, dihexylamine, N-methylethylamine or the like.

This reaction is preferably carried out in the presence of alkali metal iodide (e.g. sodium iodide, etc.) and the like.

The reaction is usually carried out in a solvent such as water, tetrahydrofuran, dioxane, N,N-dimethylformamide or any other solvent which does not adversely influence the reaction.

The reaction temperature is not critical, and the reaction is usually carried out at ambient temperature or under warming to heating.

The starting compounds (II), (IV) and (XI) or salts thereof can be prepared by the following processes.

Process A

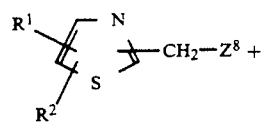

(XIII)
or its salt

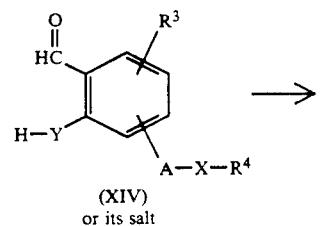

(XIV)
or its salt

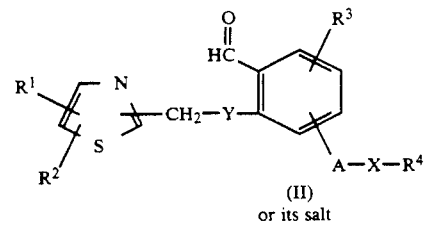

(II)
or its salt

Process B

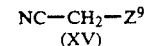

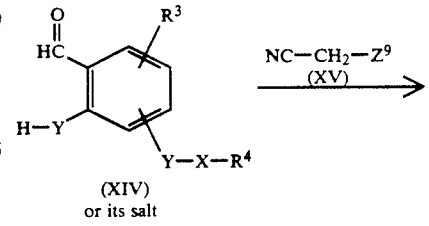

(XIV)
or its salt

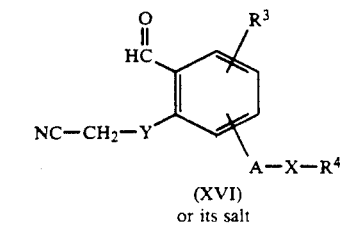

(XVI)
or its salt

Process C

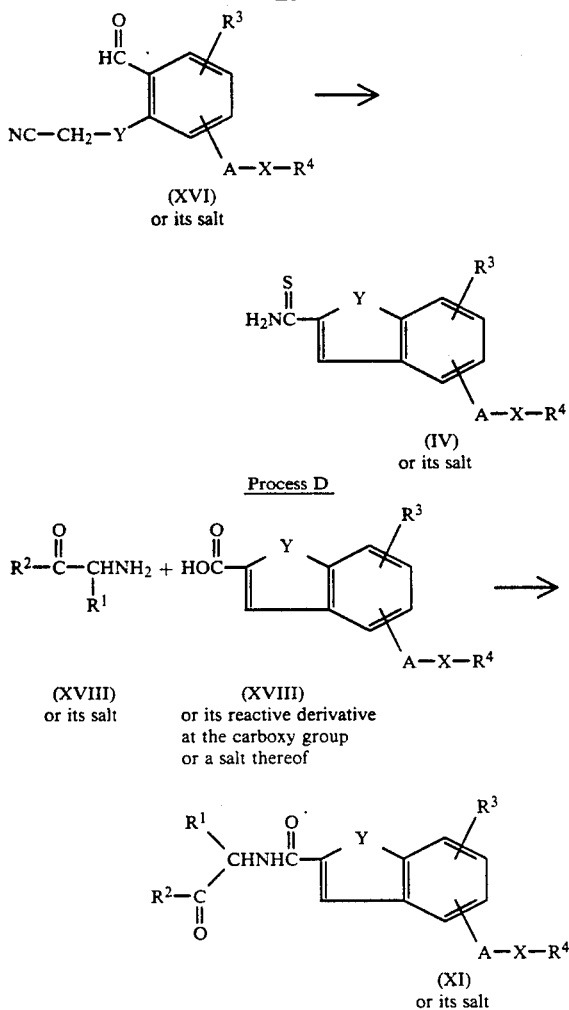

wherein
R¹, R², R³, R⁴, A, X and Y are each as defined above,
Z⁸ is acid residue, and
Z⁹ is acid residue.

The above-mentioned process for preparing the starting compounds (II), (IV) and (XI) are explained in detail in the following.

Process A

The compound (II) or its salt can be prepared by reacting a compound (XIII) or its salt with a compound (XIV) or its salt.

Suitable salt of the compound (II) may be the same as those exemplified for the compound (I).

Suitable salt of the compound (XIII) may be an acid addition salt as exemplified for the compound (I).

Suitable salt of the compound (XIV) may be a metal salt as exemplified for the compound (I).

This reaction can be carried out in substantially the same manner as Process 3, and therefore the reaction mode and reaction condition [e.g. solvent, reaction temperature, etc.] of this reaction are to be referred to those explained in Process 3.

Process B

The compound (XVI) or its salt can be prepared by reacting a compound (XIV) or its salt with a compound (XV).

Suitable salts of the compounds (XIV) and (XVI) may be a metal salt as exemplified for the compound (I).

This reaction can be carried out in substantially the same manner as Process 3, and therefore the reaction mode and reaction condition [e.g. solvent, reaction temperature, etc.] of this reaction are to be referred to those explain in Process 3.

Process C

The compound (IV) or its salt can be prepared by reacting a compound (XVI) or its salt with hydrogen sulfide or its salt.

Suitable salts of the compounds (IV) and (XVI) may be a metal salt as exemplified for the compound (I).

Suitable salt of hydrogen sulfide is its alkali metal salt [e.g. sodium hydrogen sulfide, etc.] and the like.

The reaction is usually carried out in a conventional solvent such as an alcohol [e.g. methanol, ethanol, etc.], acetone, pyridine, aromatic hydrocarbon [e.g. benzene, toluene, xylene, etc.], N,N-dimethylformamide or any other organic solvent which does not adversely influence the reaction.

The reaction temperature is not critical, and the reaction is usually carried out under cooling to heating.

Process D

The compound (XI) or its salt can be prepared by reacting a compound (XVII) or its salt with a compound (XVIII) or its reactive derivative at the carboxy group or a salt thereof.

Suitable salt of the compound (XI) may be the same as those exemplified for the compound (I).

Suitable salt of the compound (XVII) may be an acid addition salt as exemplified for the compound (I).

Suitable salts of the compound (XVIII) and its reactive derivative at the carboxy group may be a metal salt as exemplified for the compound (I).

This reaction can be carried out in substantially the same manner as Process 7, therefore the reaction mode and condition [e.g. solvent, reaction temperature, etc.] of this reaction are to be referred to those explained in Process 7.

The object compounds can be purified and isolated from the reaction mixture and converted to the desired salt in conventional manners, if necessary.

It is to be noted that the compound (I) and the other compounds may include one or more stereoisomers due to asymmetric carbon atoms, and all of such isomers and mixture thereof are included within the scope of this invention.

The object compound (I) or its pharmaceutically acceptable salts thereof possess strong activities as leukotriene and SRS-A antagonists or inhibitors, and are useful for the treatment and/or prevention of allergy or inflammation in human beings or animals, and more particularly to methods for prevention and/or treatment of asthma, psoriasis, hepatitis, bronchitis, gastritis, esophagitis, pancreatitis, arthritis, nephritis, inflammatory bowel disease, shock [e.g. septic shock, anaphylactic shock, etc.], arteriosclerosis, myocardial infarction, cerebral vasospasm, rhinitis, conjunctivitis, eczema, ishemic cerebral disease, chronic obstructive lung disease, cerebral edema, adult respiratory distress syndrome, neonatal pulmonary hypertension, Chrohn's disease, dermatitis, rheumatism, gastric ulcer, peptic ulcer, gout and the like.

In order to illustrate the usefulness of the object compound (I), the pharmacological test data of some representative compounds of the compound (I) are shown in the following.

$^3$H-Leukotriene $D_4$ receptor binding (i) Test Method (a) Crude lung membrane preparation Male Hartly strain guinea pigs were sacrificed by decapitation. The trachea and lung were removed and homogenized buffer (0.25M sucrose, 10 mM Tris-HCl pH 7.5, 0.1 mM EDTA) by using Polytoron (Kinematica). The homogenate was centrifuged ($1000 \times g$, 10 min) to remove tissue clumps and the supernatant was centrifuges ($14000 \times g$, 20 min) to yield pellets. The pellets were resuspended in buffer (5 mM Tris-HCl pH 7.5), homogenized with a teflon homogenizer and centrifuged ($14000 \times g$, 20 min) to yield pellets which were referred to as crude membrane fractions. The obtained pellets were stored at $-70°$ C. until use.

(b) $^3$H-Leukotriene $D_4$ binding to preparation membrane

Frozen crude membrane fractions were thawed and resuspended in Medium 1 (10 mM Tris-HCl pH 7.5, 10 mM $CaCl_2$, 10 mM $MgCl_2$, 5 mM cysteine, 5 mM glycine). In binding assays, $^3$H-Leukotriene $D_4$ (0.3 nM) and drug were incubated with 100 μl of the membrane preparation in Medium 1 at 25° C. for 30 minutes in a final volume of 500 μl. Separation of receptor-bound from free $^3$H-Leukotriene $D_4$ is achieved by immediate filtration through Whatman GF/B filters under vacuum and washed three times with 5 ml of ice-cold buffer (10 mM Tris-HCl pH 7.5). Non-specific binding was defined as binding in the presence of 1 μM Leukotriene $D_4$. The radioactivity retained on rinsed filters was determined by a liquid-scintillation counter (Packerd TRI-CARB 4530).

(ii) Test Results

| Test Compound (Example No.) | $IC_{50}$ (M) |
|---|---|
| 12 | $3.82 \times 10^{-8}$ |
| 13-2) | $1.78 \times 10^{-8}$ |
| 18 | $4.88 \times 10^{-8}$ |
| 19-2) | $6.77 \times 10^{-8}$ |
| 51 | $1.38 \times 10^{-8}$ |

For therapeutic purpose, the compound (I) and a pharmaceutically acceptable salt thereof of the present invention can be used in a form of pharmaceutical preparation containing one of said compounds, as an active ingredient, in admixture with a pharmaceutically acceptable carrier such as an organic or inorganic solid, semi-solid or liquid excipient suitable for oral, parenteral or external [topical] administration. The pharmaceutical preparations may be capsules, tablets, dragees, granules, suppositories, solution, lotion, inhalant, ophthalmic preparations, collunarium, suspension, emulsion, ointment, gel, or the like. If desired, there may be included in these preparations, auxiliary substances, stabilizing agents, wetting or emulsifying agents, buffers and other commonly used additives.

While the dosage of the compound (I) will vary depending upon the age and condition of the patient, an average single dose of about 0.1 mg, 1 mg, 10 mg, 50 mg, 100 mg, 250 mg, 500 mg and 1000 mg of the compound (I) may be effective for treating the above-mentioned diseases. In general, amounts between 0.1 mg/body and about 1,000 mg/body may be administered per day.

The following Preparations and Examples are given for the purpose of illustrating this invention.

PREPARATION 1

A mixture of 2-bromomethyl-4-tert-butylthiazole (3.4 g), 2-hydroxy-5-methoxybenzaldehyde (2.21 g) and potassium carbonate (2.0 g) in acetone (25 ml) was stirred under reflux for 7 hours. After being filtered, the filtrate was concentrated under reduced pressure to give a crude residue. The residue was subjected to column chromatography on silica gel and eluted with a mixture of toluene and ethyl acetate. The fractions containing object compound were combined and concentrated under reduced pressure to give a syrup. The syrup was crystallized from n-hexane and filtered to give 4-tert-butyl-2-(2-formyl-4-methoxyphenoxymethyl)thiazole (3.23 g).

mp: 79°–80° C.

IR (Nujol): 3100, 1665, 1610, 1590, 1515, 1500 $cm^{-1}$

NMR ($CDCl_3$, δ): 1.35 (9H, s), 3.81 (3H, s), 5.42 (2H, s), 6.94 (1H, s), 7.05 (1H, d, J=9.0 Hz), 7.14 (1H, dd, J=3.0 Hz and 9.0 Hz), 7.36 (1H, d, J=3.0 Hz), 10.54 (1H, s)

MASS (m/z): 305 (M+), 154

PREPARATION 2

The following compound was obtained according to a similar manner to that of Preparation 1.

2-(2-Formyl-4-methoxyphenoxymethyl)-4-phenylthiazole mp: 104°–105° C.

IR (Nujol): 1680, 1610 $cm^{-1}$

NMR ($CDCl_3$, δ): 3.80 (3H, s), 5.48 (2H, s), 7.1–7.16 (2H, m), 7.3–7.47 (4H, m), 7.51 (1H, s), 7.87–7.91 (2H, m)

MASS (m/z): 325 (M+), 295, 252, 190, 174 (base)

PREPARATION 3

A mixture of 2-bromomethyl-4-tert-butylthiazole (1.05 g), 5-formyl-2-hydroxybenzaldehyde (0.74 g), potassium carbonate (0.89 g) and potassium iodide (small mass) in N,N-dimethylformamide was stirred at 50° C. for 5 hours. After being cooled, the resulting solution was poured into ice-water and extracted with ethyl acetate. The organic layer was washed with brine, dried over magnesium sulfate and concentrated under reduced pressure to give a syrup. The syrup was subjected to column chromatography on silica gel and eluted with a mixture of toluene and ethyl acetate. The fractions containing object compound were combined and concentrated under reduced pressure to give 4-tert-butyl-2-(2,4-diformylphenoxymethyl)thiazole (1.0 g).

mp: 77.5°–78.5° C.

IR (Nujol): 1695, 1605, 1580 $cm^{-1}$

NMR ($CDCl_3$, δ): 1.36 (9H, s), 5.58 (2H, s), 6.99 (1H, s), 7.32 (1H, d, J=8.7 Hz), 8.13 (1H, dd, J=8.7 Hz and 2.2 Hz), 8.37 (1H, d, J=2.2 Hz), 9.97 (1H, s), 10.58 (1H, s)

MASS (m/z): 303 (M+), 154 (base)

PREPARATION 4

To a cooled mixture of 2-hydroxy-5-methoxybenzaldehyde (500.0 g), potassium carbonate (908.4 g) and potassium iodide (272.8 g) in N,N-dimethylformamide (2.5 l) chloroacetonitrile (297.7 g) was added dropwise over 8 minutes below 10° C. under nitrogen. After being stirred at ambient temperature for 110 minutes, the mixture was poured slowly into ice-water (20 l) and stirred for 2 hours. The precipitates were cooled by centrifugal filtration, washed with water (1 l) 7 times and air-dried at ambient temperature to give 2-cyanomethoxy-5-methoxybenzaldehyde (571.4 g).

mp: 71°-72° C.

IR (Nujol): 2070, 1680, 1610, 1205, 1040 cm$^{-1}$

NMR (CDCl$_3$, δ): 3.83 (3H, s), 4.88 (2H, s), 7.05 (1H, d, J=9.0 Hz), 7.18 (1H, dd, J=3.2 Hz and 9.0 Hz), 7.38 (1H, d, J=3.2 Hz), 10.39 (1H, s)

PREPARATION 5

To a solution of 2-cyanomethoxy-5-methoxybenzaldehyde (420.0 g) in N,N-dimethylformamide (2.1 l), sodium hydrogen sulfide (281.5 g) was added over 16 minutes and stirred for 3 hours and 20 minutes below 8° C. After being stirred for 1 hour at 40° to 47° C., the mixture was poured into ice-water (10.5 l) with stirring. The resulting mixture was neutralized with 6N-aqueous hydrochloric acid and further stirred for 30 minutes. The resulting precipitates were collected by filtration, washed with water (1 1×5 times) and dried at 50° C. under reduced pressure to give 5-methoxy-2-benzofurancarbothioamide (408.2 g).

mp: 163°-164° C.

IR (Nujol): 3420, 3140, 1617, 1561, 1209 cm$^{-1}$

NMR (CDCl$_3$, δ): 3.85 (3H, s), 7.01-7.10 (2H, m), 7.34-8.02 (4H, m)

PREPARATION 6

The following compound was obtained according to a similar manner to that of Preparation 5.

5-Hydroxy-2-benzofurancarbothioamide

IR (Nujol): 3400, 3300, 3150, 1620, 1570 cm$^{-1}$

NMR (DMSO-d$_6$, δ): 6.93 (1H, dd, J=8.9 Hz and 2.4 Hz), 7.03 (1H, dd, J=2.4 Hz and 0.9 Hz), 7.41 (1H, d, J=8.9 Hz), 7.56 (1H, d, J=0.9 Hz), 9.43 (1H, s), 9.56 (1H, s), 9.88 (1H, s)

MASS (m/z): 193 (M+)

PREPARATION 7

To a being cooled solution of DL-α-amino-ε-caprolactam (0.83 g) and triethylamine (1.1 ml) in dichloromethane (12 ml), a solution of (5-methoxybenzofuran-2-yl)carbonyl chloride (1.37 g) in dichloromethane (5 ml) was added dropwise below 10° C. After being stirred for 3 hours at ambient temperature, the appeared precipitates was collected by filtration to give DL-α-(5-methoxybenzofuran-2-yl)carbonylamino-ε-caprolactam (1.20 g).

IR (Nujol): 3600, 3400, 3200, 1660, 1590 cm$^{-1}$

NMR (DMSO-d$_6$, δ): 1.61-2.0 (7H, m), 3.0-3.27 (2H, m), 3.81 (3H, s), 4.61 (1H, dd, J=6.5 Hz and 10 Hz), 7.07 (1H, dd, J=2.6 Hz and 9 Hz), 7.26 (1H, d, J=2.6 Hz), 7.52 (1H, s), 7.62 (11H, d, J=9.0 Hz), 8.0-8.1 (1H, m), 8.27 (1H, d, J=6.5 Hz)

MASS (m/z): 302 (M+), 273, 191, 175 (base)

PREPARATION 8

The following compound was obtained according to a similar manner to that of Example 1.

2-Acetyl-5-methoxybenzofuran

IR (Nujol): 1680, 1620, 1560 cm$^{-1}$

NMR (CDCl$_3$, δ): 2.59 (3H, s), 3.85 (3H, s), 7.06-7.12 (2H, m), 7.43-7.54 (2H, m)

MASS (m/z): 190 (M+), 175

PREPARATION 9

A mixture of 2-acetyl-5-methoxybenzofuran (1.23 g) and cupric bromide (2.74 g) in methanol (10 ml) was stirred under reflux for 4 hours. The resulting mixture was filtered and the filtrate was evaporated. To the resultant, water was added and the mixture was extracted with toluene. The organic layer was washed with brine, dried over magnesium sulfate and concentrated under reduced pressure to give 2-bromoacetyl-5-methoxybenzofuran (1.66 g).

NMR (CDCl$_3$, δ): 3.86 (3H, s), 4.54 (2H, s), 7.08-7.23 (2H, m), 7.48 (1H, d, J=8.8 Hz), 7.58 (1H, d, J=0.9 Hz)

PREPARATION 10

The following compound was obtained according to a similar manner to that of Example 4.

5-Hydroxy-2-benzofurancarbothioamide

IR (Nujol): 3400, 3300, 3150, 1620, 1570 cm$^{-1}$

NMR (DMSO-d$_6$, δ): 6.93 (1H, dd, J=8.9 Hz and 2.4 Hz), 7.03 (1H, dd, J=2.4 Hz and 0.9 Hz), 7.41 (1H, d, J=8.9 Hz), 7.56 (1H, d, J=0.9 Hz), 9.43 (1H, s), 9.56 (1H, s), 9.88 (1H, s)

MASS (m/z): 193 (M+)

PREPARATION 11

A solution of ethyl 2-bromomethylbenzoate (1.00 g) in tetrahydrofuran (10.0 ml) and triphenylphosphine (1.21 g) was heated under reflux for 8 hours. After being cooled, the resulting precipitates were collected by filtration and washed with tetrahydrofuran to give 2-ethoxycarbonylbenzyltriphenylphosphonium bromide (1.17 g).

mp: 195°-205° C.

IR (Nujol): 1697, 1265, 1110 cm$^{-1}$

NMR (DMSO-d$_6$, δ): 1.08 (3H, t, J=7.1 Hz), 3.88 (2H, q, J=7.1 Hz), 5.53 (2H, d, J=15.5 Hz), 7.25-7.34 (1H, m), 7.51-7.60 (8H, m), 7.68-7.78 (6H, m), 7.88-7.95 (4H, m)

MASS (m/z): 425

EXAMPLE 1

A mixture of 4-tert-butyl-2-(2-formyl-4-methoxyphenoxymethyl)thiazole (3.23 g) and acetic anhydride (3.2 ml) in xylene (30 ml) was stirred at 140° C. for 14 hours. After being cooled, the resulting mixture was concentrated to give a syrup. The syrup was subjected to column chromatography on silica gel and eluted with toluene. The fractions containing object compound were combined and concentrated under reduced pressure to give 4-tert-butyl-2-(5-methoxybenzofuran-2-yl)thiazole (2.40 g).

mp: 80°-81° C.

IR (Nujol): 3150, 1625, 1590, 1500 cm$^{-1}$

NMR (CDCl$_3$, δ): 1.41 (9H, s), 3.85 (3H, s), 6.94 (1H, dd, J=2.6 Hz and 8.9 Hz), 6.96 (1H, s), 7.05 (1H, d, J=2.6 Hz), 7.28 (1H, d, J=0.8 Hz), 7.43 (1H, d, J=8.9 Hz)

MASS (m/z): 287 (M+), 272, 152

EXAMPLE 2

The following compound was obtained according to a similar manner to that of Example 1.

5-Methoxybenzofuran-2-yl)-4-phenylthiazole mp: 109°-110° C.

IR (Nujol): 1610, 1585 cm$^{-1}$

NMR (CDCl$_3$, δ): 3.86 (3H, s), 6.97 (1H, dd, J=2.6 Hz and 9.0 Hz), 7.09 (1H, d, J=2.6 Hz), 7.32-7.50 (5H, m), 7.52 (1H, s), 7.95-8.01 (2H, m)

MASS (m/z): 307 (M+, base), 264, 236

EXAMPLE 3

A mixture of 4-tert-butyl-2-(2,4-diformylphenoxymethyl)thiazole (0.95 g) and acetic anhydride (12.9 ml) in dried xylene (100 ml) was stirred at 130° C. for 27 hours. After being cooled, the resulting mixture was concentrated in reduced pressure to give a residue. The residue was crystallized with diisopropyl ether. The resulting crystals were collected by filtration and washed with diisopropyl ether to give 4-tert-butyl-2-(5-formylbenzofuran-2-yl)thiazole (11.01 g).

mp: 83°-84° C.

IR (Nujol): 3100, 1700, 1590, 1500 cm$^{-1}$

NMR (CDCl$_3$, δ): 1.41 (9H, s), 7.04 (1H, s), 7.43 (1H, s), 7.66 (1H, d, J=8.7 Hz), 7.91 (1H, dd, J=2.2 Hz and 8.7 Hz), 8.16 (1H, d, J=2.2 Hz), 10.07 (1H, s)

MASS (m/z): 285 (M+), 270 (base), 243

EXAMPLE 4

To a cooled solution of 4-tert-butyl-2-(5-methoxybenzofuran-2-yl)thiazole (1.0 g) in dichloromethane (10 ml), 1M solution of boron tribromide in dichloromethane (7 ml) was added dropwise at 5° C. After being stirred for 3 hours, the resulting solution was poured into a mixture of ice and aqueous sodium hydrogen carbonate. The resulting precipitates were collected by filtration and dissolved in a mixture of tetrahydrofuran and water. The solution was concentrated to give crystals of 4-tert-butyl-2-(5-hydroxybenzofuran-2-yl)thiazole (0.91 g).

mp: 179°-180° C.

IR (Nujol): 2600, 1610, 1585, 1510 cm$^{-1}$

NMR (CDCl$_3$, δ): 1.41 (9H, s), 6.86 (1H, dd, J=2.5 Hz and 8.8 Hz), 6.97 (1H, s), 7.01 (1H, d, J=2.5 Hz), 7.26 (1H, d, J=1.4 Hz), 7.37 (1H, d, J=8.8 Hz)

MASS (m/z): 273 (M+), 258

EXAMPLE 5

The following compounds were obtained according to a similar manner to that of Example 4.

1) 2-(5-Hydroxybenzofuran-2-yl)-4-phenylthiazole mp: 190°-210° C.

IR (Nujol): 3550, 1575 cm$^{-1}$

NMR (DMSO-d$_6$, δ): 6.89 (1H, dd, J=2.5 Hz and 9.0 Hz), 7.05 (1H, d, J=2.5 Hz), 7.36-7.54 (5H, m), 8.04-8.07 (2H, m), 8.28 (1H, s), 9.42 (1H, s)

MASS (m/z) 293 (M+), 134 (base)

2) 2-(5-Hydroxybenzofuran 2-yl)-4-methylthiazole mp: 247°-248° C.

IR (Nujol): 3125, 1579, 1215, 789 cm$^{-1}$

NMR (DMSO-d$_6$, δ): 2.44 (3H, s), 6.84 (1H, dd, J=2.5 Hz and 8.8 Hz), 7.00 (1H, d, J=2.5 Hz), 7.37 (1H, s), 7.44 (1H, s), 7.46 (1H, d, J=8.8 Hz), 9.38 (1H, s)

MASS (m/z): 231 (M+, base), 159, 72

3)
2-(5-Hydroxybenzofuran-2-yl)-4-trifluoromethylthiazole mp: 235°-236° C.

IR (Nujol): 3230, 1620, 1580, 1540, 1485 cm$^{-1}$

NMR (DMSO-d$_6$, δ): 6.91 (1H, dd, J=2.4 Hz and 8.9 Hz), 7.03 (1H, d, J=2.4 Hz), 7.52 (1H, d, J=8.9 Hz), 7.60 (1H, s), 8.62 (1H, s), 9.67 (1H, s)

MASS (m/z): 285 (M+, base), 228, 159

4)
2-(5-Hydroxybenzo[b]thiophen-2-yl)-4-tert-butylthiazol mp: 140°-142° C.

IR (Nujol): 3100 (br), 1595, 1520, 1500, 1400, 1330, 1225, 1210 cm$^{-1}$

NMR (CDCl$_3$, δ): 1.39 (9H, s), 5.6-5.8 (1H, br), 6.89 (1H, s), 6.94 (1H, dd, J=2.5 Hz and 8.7 Hz), 7.19 (1H, d, J=2.5 Hz), 7.60 (1H, s), 7.64 (1H, d, J=8.7 Hz)

MASS (m/z): 289 (M+), 274 (base), 247

5)
4-(Adamantan-1-yl)-2-(5-hydroxybenzofuran-2-yl)thiazole

IR (Nujol): 3150, 1590, 1560 cm$^{-1}$

NMR (DMSO-d$_6$, δ): 1.7-1.8 (6H, m), 1.97-2.05 (9H, m), 6.86 (1H, dd, J=2.5 Hz and 8.8 Hz), 7.02 (1H, d, J=2.5 Hz), 7.36 (1H, s), 7.38 (1H, s), 7.48 (1H, d, J=8.8 Hz), 7.05 (1H, br)

MASS (m/z): 351 (M+, base), 294, 282

6)
2-(5-Hydroxybenzofuran-2yl)-4,5,6,7-tetrahydrobenzothiazole mp: >290° C.

IR (Nujol): 3150, 2700, 1610, 1580, 1545 cm$^{-1}$

NMR (DMSO-d$_6$, δ): 1.65-2.0 (4H, m), 2.7-3.0 (4H, m), 6.82 (1H, d, J=9 Hz), 6.98 (1H, br s), 7.30 (1H, br s), 7.42 (1H, d, J=9 Hz), 9.4 (1H, br s)

MASS (m/z): 271 (M+, base), 243, 238

7) 4-Cyclobutyl-2-(5-hydroxybenzofuran-2-yl)thiazole

IR (Nujol): 3250, 1615, 1580, 1515 cm$^{-1}$

NMR (DMSO-d$_6$, δ): 1.87-2.36 (6H, m), 3.70 (1H, sext, J=8.3 Hz), 6.85 (1H, dd, J=2.5 Hz and 8.9 Hz), 7.01 (1H, d, J=2.5 Hz), 7.39 (1H, d, J=0.7 Hz), 7.47 (1H, d, J=8.9 Hz), 7.49 (1H, s), 9.38 (1H, s)

MASS (m/z): 271 (M+), 243 (base), 159

8) 2-(5-Hydroxybenzofuran-2-yl)-4-(2-thienyl)thiazole

IR (Nujol): 3300, 1590, 1570 cm$^{-1}$

NMR (DMSO-d$_6$, δ): 6.89 (1H, dd, J=2.6 Hz and 9.0 Hz), 7.10 (1H, d, J=2.6 Hz), 7.15-7.7 (6H, m), 8.19 (1H, br)

MASS (m/z): 299 (M+, base), 218, 140

9) 2-(5-Hydroxybenzofuran-2-yl)-4-(2-pyridyl)thiazole mp: 210°-212° C.

IR (Nujol): 3400, 1615, 1590, 1570 cm$^{-1}$

NMR (DMSO-d$_6$, δ): 6.88 (1H, dd, J=2.5 Hz and 9 Hz), 7.05 (1H, d, J=2.5 Hz), 7.35-7.45 (1H, m), 7.52 (1H, d, J=9 Hz), 7.54 (1H, s), 7.97 (1H, dt, J=1.6 Hz and 7.8 Hz), 8.18 (1H, d, J=7.8 Hz), 8.42 (1H, s), 8.67 (1H, d, J=7.8 Hz), 9.48 (1H, s)

MASS (m/z): 294 (M+), 135 (base)

10)
8-Acetyl-2-(5-hydroxybenzofuran-2-yl)-4,5,6,7-tetrahydro-8H-thiazolo[5,4-b]azepine mp: 222°-223° C.

IR (Neat): 2900, 1660, 1580, 1550 cm$^{-1}$

NMR (CDCl$_3$, δ): 1.72-2.05 (4H, m), 2.18 (s) and 2.34 (s)(3H), 3.0-3.05 (2H, m), 3.6-4.0 (2H, m), 6.86 (dd) and 6.91 (dd)(1H, J=2.6 Hz and 9.0 Hz), 7.02 (d) and 7.04

(d)(1H, J=2.6 Hz), 7.11 (s) and 7.22 (s)(1H), 7.35 (d) and 7.38 (d)(1H, J=9.0 Hz)

MASS (m/z): 328 (M+), 286, 177

11) 4-(5-Hydroxybenzofuran-2-yl)-2-tert-butylthiazole hydrobromide

IR (Nujol): 3300, 1620, 1600 cm$^{-1}$
NMR (CDCl$_3$, δ): 1.50 (9H, s), 6.79 (1H, dd, J=8.7 Hz and 2.6 Hz), 7.00 (1H, d, J=2.6 Hz), 7.12 (1H, s), 7.33 (1H, d, J=8.7 Hz), 7.52 (1H, s)
MASS (m/z): 273 (M+), 258

12) 2-(5-Hydroxybenzofuran-2-yl)-5-isopropylthiazole

NMR (DMSO-d$_6$, δ): 1.34 (6H, d, J=6.7 Hz), 3.30 (1H, sep, J=6.7 Hz), 6.84 (1H, dd, J=8.8 Hz and 2.5 Hz), 7.01 (1H, d, J=2.5 Hz), 7.37 (1H, s), 7.45 (1H, d, J=8.8 Hz), 7.74 (1H, s)

EXAMPLE 6

To a cooled solution of 4-tert-butyl-2-(5-hydroxybenzofuran-2-yl)thiazole (0.8 g) in tetrahydrofuran (16 ml), sodium hydride ((60% in mineral oil) 0.152 g) was added below 10° C. After being stirred for 30 minutes, α,α'-dichloroxylene (2.05 g) was added to the mixture. After subsequently being stirred at ambient temperature for 30 minutes, the mixture was refluxed for 9.5 hours. After the solvent was removed under reduced pressure, the residue was subjected to column chromatography on silica gel (25 g) and eluted with a mixture of n-hexane and toluene (1:1). The fractions containing object compound were combined and concentrated under reduced pressure to give an oil of 4-tert-butyl-2-[5-(2-chloromethylphenylmethoxy)benzofuran-2-yl]thiazole (0.9 g).

IR (Neat): 1610, 1590, 1500 cm$^{-1}$
NMR (CDCl$_3$, δ): 1.41 (9H, s), 4.75 (2H, s), 5.23 (2H, s), 6.96 (1H, s), 7.02 (1H, dd, J=2.6 Hz and 8.9 Hz), 7.15–7.18 (1H, m), 7.28 (1H, s), 7.33–7.48 (5H, m)
MASS (m/z) 411 (M+), 377, 287, 272, 139 (base)

EXAMPLE 7

The following compounds were obtained according to a similar manner to that of Example 6.

1)
2-[5-(2-Chloromethylphenylmethoxy)benzofuran-2-yl]-4-phenylthiazole mp: 132°–134° C.
IR (Nujol): 1610, 1590 cm$^{-1}$
NMR (CDCl$_3$, δ): 4.76 (2H, s), 5.25 (2H, s), 7.06 (1H, dd, J=2.6 Hz and 9.0 Hz), 7.21 (1H, d, J=2.6 Hz), 7.33–7.53 (9H, m), 7.59 (1H, s), 7.96–8.01 (2H, m)
MASS (m/z): 431 (M+), 397, 293, 264, 139, 105

2)
2-[5-(2-Chloromethylphenylmethoxy)benzofuran-2-yl]-4-isopropylthiazole mp: 88°–90° C.
IR (Nujol): 1585, 1203, 834 cm$^{-1}$
NMR (CDCl$_3$, δ): 1.37 (6H, d, J=6.9 Hz), 3.21 (1H, sep, J=6.9 Hz), 4.75 (2H, s), 5.24 (2H, s), 6.95 (1H, d, J=0.9 Hz), 7.03 (1H, dd, J=2.6 Hz and 9.0 Hz), 7.18 (1H, d, J=2.6 Hz), 7.28 (1H, d, J=0.8 Hz), 7.34–7.51 (5H, m)
MASS (m/z): 397, 364, 259, 105 (base)

3)
2-[5-(2-Chloromethylphenylmethoxy)benzofuran-2-yl]-4-methylthiazole mp: 127° C.
IR (Nujol): 1589, 1204, 838 cm$^{-1}$
NMR (CDCl$_3$, δ): 2.54 (3H, s), 4.75 (2H, s), 5.24 (2H, s), 6.95 (1H, d, J=0.9 Hz), 7.04 (1H, dd, J=2.6 Hz and 9.0 Hz), 7.19 (1H, d, J=2.5 Hz), 7.27 (1H, d, J=0.7 Hz), 7.35–7.54 (5H, m)
MASS (m/z): 369, 335, 231, 174, 139

4)
2-[5-(2-Chloromethylphenylmethoxy)benzofuran-2-yl]-4-4-(4-methoxy)phenylthiazole mp: 143°–145° C.
IR (Nujol): 1610, 1584, 1246, 1195, 1021, 774 cm$^{-1}$
NMR (CDCl$_3$, δ): 3.86 (3H, s), 4.76 (2H, s), 5.25 (2H, s), 6.98 (1H, d, J=8.8 Hz), 7.05 (1H, dd, J=2.6 Hz and 9.0 Hz), 7.20 (1H, d, J=2.6 Hz), 7.35–7.54 (8H, m), 7.92 (2H, d, J=8.8 Hz)
MASS (m/z): 461 (M+), 427, 337, 105 (base)

5)
2-[5-(2-Chloromethylphenylmethoxy)benzofuran-2-yl]-4-trifluoromethylthiazole

IR (Nujol): 3130, 1590, 1525 cm$^{-1}$
NMR (CDCl$_3$, δ): 4.75 (2H, s), 5.24 (2H, s), 7.09 (1H, dd, J=2.6 Hz and 8.9 Hz), 7.21 (1H, d, J=2.6 Hz), 7.25–7.5 (6H, m), 7.79 (1H, s)
MASS (m/z): 423, 387, 370, 358, 234, 139 (base)

6)
2-[5-(2-Chloromethylphenylmethoxy)benzo[b]thiophen-2-yl]-4-tert-butylthiazole IR (Neat): 1600, 1490, 1440, 1410, 1200 cm$^{-1}$
NMR (CDCl$_3$, δ): 1.39 (9H, s), 4.75 (2H, s), 5.26 (2H, s), 6.88 (1H, s), 7.09 (1H, dd, J=2.5 Hz and 8.7 Hz), 7.3–7.7 (5H, m), 7.67 (1H, s), 7.70 (1H, d, J=8.7 Hz)
MASS (m/z): 427 (M+), 391, 374, 288, 250, 139 (base)

7)
4-(Adamantan-1-yl)-2-[5-(2-chloromethylphenylmethoxy)benzofuran-2-yl]thiazole IR (Nujol): 1615, 1590, 1490 cm$^{-1}$
NMR (CDCl$_3$, δ); 1.75–1.80 (6H, m), 2.0–2.2 (9H, m), 4.76 (2H, s), 5.24 (2H, s), 6.92 (1H, s), 7.03 (1H, dd, J=2.6 Hz and 9.0 Hz), 7.30 (1H, s), 7.34–7.53 (6H, m)
MASS (m/z): 489 (M+), 453, 351, 294, 105 (base)

8)
2-[5-(2-Chloromethylphenylmethoxy)benzofuran-2-yl]-4,5,6,7-tetrahydrobenzothiazole mp: 131°–132° C.
NMR (CDCl$_3$, δ): 1.8–2.0 (4H, m), 2.8–3.0 (4H, m), 4.75 (2H, s), 5.24 (2H, s), 7.02 (1H, dd, J=2.6 Hz and 9.0 Hz), 7.17 (1H, d, J=2.6 Hz), 7.22 (1H, s), 7.35–7.54 (5H, m)
MASS (m/z): 409 (M+), 374, 270, 214, 139, 105 (base)

9)
4-Cyclobutyl-2-[5-(2-chloromethylphenylmethoxy)benzofuran-2-yl]thiazole mp: 82°–83° C.
IR (Nujol): 3150, 1615, 1585 cm$^{-1}$
NMR (CDCl$_3$, δ): 1.91–2.44 (6H, m), 3.76 (1H, sext, J=8.3 Hz), 4.75 (2H, s), 5.23 (2H, s), 6.98 (1H, s), 7.01 (1H, dd, J=2.6 Hz and 9.0 Hz), 7.18 (1H, d, J=2.6 Hz), 7.28 (1H, s), 7.31–7.51 (5H, m)

MASS (m/z): 409 (M+), 381, 373, 345, 243, 139 (base)

10)

2-[5-(2-Chloromethylphenylmethoxy)benzofuran-2-yl]-4-(2-thienyl)thiazole mp: 88°–89° C.
IR (Nujol): 1585, 1550 cm$^{-1}$
NMR (CDCl$_3$, δ): 4.76 (2H, s), 5.24 (2H, s), 7.07–7.11 (2H, m), 7.20 (1H, d, J=2.5 Hz), 7.40 (1H, m), 7.31–7.54 (7H, m)
MASS (m/z): 437(M+), 401, 313 (base), 140

11)

2-[5-(2-Chloromethylphenylmethoxy)benzofuran-2-yl]-4-(2-pyridyl)thiazole

IR (Nujol): 1590 cm$^{-1}$
NMR (DMSO-d$_6$, δ): 4.94 (2H, s), 5.33 (2H, s), 7.16 (1H, dd, J=2.6 Hz and 9.0 Hz), 7.35–7.60 (6H, m), 7.63 (1H, s), 7.68 (1H, d, J=9.0 Hz), 7.96 (1H, dt, J=1.8 Hz and 7.6 Hz), 8.18 (1H, d, J=7.6 Hz), 8.44 (1H, s), 8.66–8.68 (1H, m)
MASS (m/z): 432 (M+), 396, 294

12)

2-[5-(2-Chloromethylphenylmethoxy)benzofuran-2-yl]-4-neopentylthiazole

IR (Neat): 1610, 1584, 1190, 1018, 800, 728 cm$^{-1}$
NMR (CDCl$_3$, δ): 1.00 (9H, s), 2.76 (2H, s), 4.76 (2H, s), 5.24 (2H, s), 6.95 (1H, s), 7.03 (1H, dd, J=2.6 Hz and 3.9 Hz), 7.18 (1H, d, J=2.6 Hz), 7.23–7.54 (6H, m)
MASS (m/z): 425, 389, 287, 231, 159, 105 (base)

13)

2-[5-(2-Chloromethylphenylmethoxy)benzofuran-2-yl]-4-cyclopropylthiazole

IR (Neat): 3100, 1610, 1590, 1520 cm$^{-1}$
NMR (CDCl$_3$, δ): 0.93–1.06 (4H, m), 2.08–2.21 (1H, m), 4.76 (2H, s), 5.24 (2H, s), 6.88 (1H, s), 7.03 (1H, dd, J=8.9 Hz and 2.6 Hz), 7.14–7.57 (5H, m), 7.18 (1H, dd, J=2.6 Hz and 0.7 Hz), 7.28 (1H, d, J=0.7 Hz)
MASS (m/z): 395 (M+), 257, 256

14)

8-Acetyl-2-[5-(2-chloromethylphenylmethoxy)benzofuran-2-yl]-4,5,6,7-tetrahydro-8H-thiazolo[5,4-b]azepine mp: 98°–99° C.
IR (Nujol): 1650, 1610, 1515 cm$^{-1}$
NMR (CDCl$_3$, δ): 1.72–2.17 (4H, m), 2.17 (s) and 2.33 (s)(3H), 2.99–3.09 (2H, m), 3.72–3.85 (2H, m), 4.75 (2H, s), 5.42 (2H, s), 7.03–7.54 (8H, m)
MASS (m/z): 466 (M+, base), 430, 424, 388, 327

15)

4-[5-(2-Chloromethylphenylmethoxy)benzofuran-2-yl]-2-tert-butylthiazole

IR (Neat): 3140, 1610, 1600 cm$^{-1}$
NMR (CDCl$_3$, δ): 1.50 (9H, s), 4.76 (2H, s), 5.23 (2H, s), 6.97 (1H, dd, J=8.9 Hz and 2.6 Hz), 7.13–7.54 (7H, m), 7.52 (1H, s)
MASS (m/z): 411 (M+), 375, 272

16)

4-(N-Acetyl-tert-butylaminomethyl)-2-[5-(2-chloromethylphenylmethoxy)benzofuran-2-yl]thiazole IR (Neat): 3100, 1650, 1590 cm$^{-1}$
NMR (CDCl$_3$, δ): 1.50 (9H, s), 2.18 (3H, s), 4.76 (4H, s), 5.25 (2H, s), 7.03–7.50 (9H, m)
MASS (m/z): 482 (M+)

17)

2-[5-(2-Chloromethylphenylmethoxy)benzofuran-2-yl]-4-hexylthiazole

IR (Nujol): 1610, 1590, 1510 cm$^{-1}$
NMR (CDCl$_3$, δ): 0.90 (3H, t, J=6.5 Hz), 1.35 (6H, m), 1.77 (2H, m), 2.85 (2H, t, J=7.7 Hz), 4.76 (2H, s), 5.24 (2H, s), 6.95 (1H, s), 7.04 (1H, dd, J=8.9 Hz and 2.6 Hz), 7.18 (1H, dd, J=2.6 Hz and 0.8 Hz), 7.29 (1H, d, J=0.8 Hz), 7.33–7.52 (5H, m)
MASS (m/s): 439 (M+)

18)

2-[5-(2-Chloromethylphenylmethoxy)benzofuran-2-yl]-4-pentylthiazole

IR (Nujol): 1610 1580 1510 cm$^{-1}$
NMR (CDCl$_3$, δ): 0.92 (3H, t, J=7.0 Hz), 1.35–1.43 (4H, m), 1.77 (2H, m), 2.85 (2H, t, J=7.7 Hz), 4.76 (2H, s), 5.24 (2H, s), 6.94 (1H, s), 7.04 (1H, dd, J=8.9 Hz and 2.6 Hz), 7.18 (1H, dd, J=2.6 Hz and 0.8 Hz), 7.28 (1H, d, J=0.8 Hz), 7.34–7.52 (5H, m)
MASS (m/z): 425 (M+)

19)

2-[5-(2-Chloromethylphenylmethoxy)benzofuran-2-yl]-5-isopropylthiazole mp: 87°–90° C.
IR (Nujol): 1583, 1204, 835, 797 cm$^{-1}$
NMR (CDCl$_3$, δ): 1.40 (6H, d, J=6.8 Hz), 3.27 (1H, sep, J=6.8 Hz), 4.75 (2H, s), 5.24 (2H, s), 7.03 (1H, dd, J=2.6 Hz and 9.0 Hz), 7.19 (1H, d, J=2.6 Hz), 7.23 (1H, d, J=0.9 Hz), 7.34–7.54 (5H, m), 7.59 (1H, d, J=0.9 Hz)
MASS (m/z): 396 (M+), 363, 105 (base)

EXAMPLE 8

To a cooled solution of 4-tert-butyl 2-(5-hydroxybenzofuran-2-yl)thiazole (0.33 g) in N,N-dimethylformamide (5 ml), sodium hydride ((60% in mineral oil) 55 mg) was added below 10° C. After being stirred for 10 minutes, 3-bromomethylbenzonitrile (0.26 g) was added to the mixture. After being stirred at ambient temperature for 2 hours, the resulting mixture was poured into ice-water and extracted with ethyl acetate. The organic layer was washed with brine, dried over magnesium sulfate, and concentrated under reduced pressure to give a syrup. The syrup was crystallized with diisopropyl ether and filtered to give crystals of 4-tert-butyl-2-[5-(3-cyanophenylmethoxy)benzofuran-2-yl]thiazole (0.38 g).

mp: 104°–106° C.
IR (Nujol): 2250, 1590 cm$^{-1}$
NMR (CDCl$_3$, δ): 1.41 (9H, s), 5.13 (2H, s), 6.98 (1H, s), 7.02 (1H, dd, J=2.6 Hz and 9.0 Hz), 7.11 (1H, d, J=2.6 Hz), 7.34 (1H, s), 7.46 (1H, d, J=9.0 Hz), 7.53 (1H, d, J=7.4 Hz), 7.61–7.72 (2H, m), 7.79 (1H, s)
MASS (m/z): 388 (M+, base), 272

EXAMPLE 9

The following compounds were obtained according to a similar manner to that of Example 8.

1)

4-tert-Butyl-2-[5-(2-methoxycarbonylphenylmethoxy)-benzofuran-2-yl]thiazole mp: 90°–90.5° C.
IR (Nujol): 1720, 1610, 1590 cm$^{-1}$
NMR (CDCl$_3$, δ): 1.41 (9H, s), 3.91 (3H, s), 5.54 (2H, s), 6.96 (1H, s), 7.05 (1H, dd, J=2.6 Hz and 9.0 Hz), 7.14 (1H, d, J=2.6 Hz), 7.25 (1H, s), 7.36 (1H, t, J=7.7 Hz), 7.45 (1H, d, J=9.0 Hz), 7.57 (1H, dt, J=1.3 Hz and 7.7 Hz), 7.80 (1H, d, J=7.7 Hz), 8.03 (1H, dd, J=1.3 Hz and 7.7 Hz)

MASS (m/z): 421 (M+), 149 (base)

2)
4-tert-Butyl-2-[5-(3-methoxycarbonylphenylmethoxy)-benzofuran-2-yl]thiazole mp: 86.5°–87.0° C.
IR (Nujol): 1725, 1620, 1590 cm$^{-1}$
NMR (CDCl$_3$, δ): 1.41 (9H, s), 3.93 (3H, s), 5.15 (2H, s), 6.97 (1H, s), 7.03 (1H, dd, J=2.6 Hz and 9.0 Hz), 7.13 (1H, d, J=2.6 Hz), 7.31 (1H, s), (1H, d like, J=7.8 Hz), 8.01 (1H, d, J=7.8 Hz), 8.14 (1H, s)
MASS (m/z): 421 (M+), 272, 149

EXAMPLE 10

A mixture of 4-tert-butyl-2-[5-(2-chloromethyl-phenylmethoxy)benzofuran-2-yl]thiazole (0.8 g), potassium cyanide (0.25 g) and Adogen 464 ((Aldrich phase transfer) one drop) in a mixture of toluene (8 ml) and water (8 ml) was stirred under reflux for 4 hours. After being cooled, the organic layer was separated, washed with brine, dried over magnesium sulfate and concentrated in reduced pressure. The resulting residue was subjected to column chromatography on silica gel and eluted with toluene. The fractions containing object compound were combined and concentrated under reduced pressure to give an oil of 4-tert-butyl-2-[5-(2-cyanomethylphenylmethoxy)benzofuran-2-yl]thiazole (0.67 g).

IR (Neat): 2250, 1610, 1590, 1500 cm$^{-1}$
NMR (CDCl$_3$, δ): 1.41 (9H, s), 3.89 (2H, s), 5.10 (2H, s), 6.97 (1H, s), 7.01 (1H, dd, J=2.6 Hz and 9.0 Hz), 7.15 (1H, d, J=2.6 Hz), 7.28 (1H, d, J=1.0 Hz), 7.35–7.54 (5H, m)
MASS (m/z): 402 (M+), 273, 258 (base)

EXAMPLE 11

The following compounds were obtained according to a similar manner to that of Example 10.

1)
2-[5-(2-Cyanomethylphenylmethoxy)benzofuran-2-yl]-4-phenylthiazole mp: 146°–148° C.
IR (Nujol): 3150, 2260, 1610, 1590 cm$^{-1}$
NMR (CDCl$_3$, δ): 3.90 (2H, s), 5.12 (2H, s), 7.04 (1H, dd, J=2.6 Hz and 9.0 Hz), 7.19 (1H, d, J=2.6 Hz), 7.04 (1H, s), 7.54 (1H, s), 7.33–7.50 (8H, m), 7.9–8.01 (2H, m)
MASS (m/z): 422 (M+), 395, 293, 264

2)
2-[5-(2-Cyanomethylphenylmethoxy)benzofuran-2-yl]-4-isopropylthiazole mp: 89°–90° C.
IR (Nujol): 2250, 1586, 1193, 740 cm$^{-1}$
NMR (CDCl$_3$, δ): 1.37 (6H, d, J=6.9 Hz), 3.21 (1H, sep, J=6.9 Hz), 3.90 (2H, s), 5.11 (2H, s), 6.96 (1H, d, J=0.8 Hz), 7.01 (1H, dd, J=2.6 Hz and 9.0 Hz), 7.16 (1H, d, J=2.5 Hz), 7.29 (1H, d, J=0.7 Hz), 7.37–7.54 (5H, m)
MASS (m/z): 388, 258, 130 (base)

3)
2-[5-(2-Cyanomethylphenylmethoxy)benzofuran-2-yl]-4-methylthiazole mp: 127°–129° C.
IR (Nujol): 2250, 1585, 1194, 820 cm$^{-1}$
NMR (CDCl$_3$, δ): 2.54 (3H, s), 3.90 (2H, s), 5.11 (2H, s), 6.96 (1H, d, J=0.9 Hz), 7.02 (1H, dd, J=2.6 Hz and 8.9 Hz), 7.17 (1H, d, J=2.5 Hz), 7.27 (1H, d, J=0.8 Hz), 7.34–7.54 (5H, m)
MASS m/z): 360, 310, 282, 254, 231 (base), 130

4)
2-[5-(2-Cyanomethylphenylmethoxy)benzofuran-2-yl]-4-(4-methoxy)phenylthiazole mp: 145°–146° C.
IR (Nujol): 2250, 1610, 1580, 1248, 1190, 1022, 746 cm$^{-1}$
NMR (CDCl$_3$, δ): 3.86 (3H, s), 3.90 (2H, s), 5.12 (2H, s), 6.95–7.06 (3H, m), 7.19 (1H, d, J=2.4 Hz), 7.33–7.55 (7H, m), 7.88–7.94 (2H, m)
MASS (m/z): 452 (M+), 337 (base), 323

5)
4-(Adamantan-1-yl)-2-[5-(2-cyanomethylphenylmethoxy)benzofuran-2-yl]thiazole IR (Neat): 3150, 3050, 2250, 1610, 1590 cm$^{-1}$
NMR (CDCl$_3$, δ): 1.75–1.80 (6H, m), 2.0–2.2 (9H, m), 3.90 (2H, s), 5.11 (2H, s), 6.93 (1H, s), 7.01 (1H, dd, J=2.6 Hz and 9.0 Hz), 7.16 (1H, d, J=2.6 Hz), 7.32 (1H, s), 7.36–7.54 (5H, m)
MASS (m/z): 480 (M+, base), 350, 322, 294, 130

6)
2-[5-(2-Cyanomethylphenylmethoxy)benzofuran-2-yl]-4,5,6,7-tetrahydrobenzothiazole mp: 162°–163° C.

IR (Nujol): 2250, 1615, 1600, 1580, 1535 cm$^{-1}$
NMR (CDCl$_3$, δ): 1.89–2.07 (4H, m), 2.84–2.88 (4H, m), 3.89 (2H, s), 5.10 (2H, s), 6.99 (1H, dd, J=2.6 Hz and 9.0 Hz), 7.15 (1H, d, J=2.6 Hz), 7.20 (1H, d, J=0.7 Hz), 7.33–7.54 (5H, m)
MASS (m/z): 400 (M+, base), 270, 242, 130

7)
4-Cyclobutyl-2-[5-(2-cyanomethylphenylmethoxy)benzofuran-2-yl]thiazole

IR (Neat): 2250, 1610, 1585, 1500 cm$^{-1}$
NMR (CDCl$_3$, δ): 1.92–2.44 (6H, m), 3.76 (1H, sext, J=8.3 Hz), 3.89 (2H, s), 5.11 (2H, s), 7.00 (1H, s), 7.01 (1H, dd, J=2.6 Hz and 9.0 Hz), 7.18 (1H, d, J=2.6 Hz), 7.30 (1H, d, J=0.7 Hz), 7.2–7.5 (5H, m)
MASS (m/z): 400 (M+), 372, 270, 242, 214

8)
2-[5-(2-Cyanomethylphenylmethoxy)benzofuran-2-yl]-4-(2-thienyl)thiazole mp: 113°–115° C.
IR (Nujol): 2250, 1610, 1590, 1550 cm$^{-1}$
NMR (CDCl$_3$, δ): 3.90 (2H, s), 5.22 (2H, s), 7.04 (1H, dd, J=2.6 Hz and 9.0 Hz), 7.06–7.11 (1H, m), 7.18 (1H, d, J=2.6 Hz), 7.33 (1H, dd, J=1.1 Hz and 5.0 Hz), 7.39 (1H, m), 7.38–7.54 (6H, m)
MASS (m/z): 428 (M+), 313, 299, 149, 91

9)
8-Acetyl-2-[5-(2-cyanomethylphenylmethoxy)benzofuran-2-yl]-4,5,6,7-tetrahydro-8H-thiazolo[5,4-b]azepine IR (Neat): 2900, 1670, 1615, 1580 cm$^{-1}$
NMR (CDCl$_3$, δ): 1.72–2.04 (4H, m), 2.17 (s) and 2.33 (s)(3H), 2.97–3.07 (2H, m), 3.7–3.9 (2H, m), 3.90 (2H, s), 5.11 (2H, s), 7.00 (dd) and 7.03 (dd)(1H, J=2.6 Hz and 9.0 Hz), 7.15 (d) and 7.18 (d)(1H, J=2.6 Hz), 7.34 (1H, s), 7.40–7.54 (5H, m)
MASS (m/z): 457 (M+, base), 415, 342, 328, 286, 257

10)
2-[5-(2-Cyanomethylphenylmethoxy)benzofuran-2-yl]-5-isopropylthiazole mp: 113°–116° C.
IR (Nujol): 2250, 1580, 1202, 840, 747 cm$^{-1}$
NMR (CDCl$_3$, δ): 1.40 (6H, d, J=6.8 Hz), 3.28 (1H, sep, J=6.8 Hz), 3.89 (2H, s), 5.11 (2H, s), 7.01 (1H, dd, J=2.6 Hz and 9.0 Hz), 7.17 (1H, d, J=2.5 Hz), 7.23 (1H, d, J=0.9 Hz), 7.34–7.55 (5H, m), 7.60 (1H, d, J=0.9 Hz)
MASS (m/z): 388 (M$^+$), 258, 130 (base)

EXAMPLE 12

A mixture of 4-tert-butyl-2-[5-(2-cyanomethylphenylmethoxy)benzofuran-2-yl]thiazole (0.40 g), sodium azide (0.58 g) and ammonium chloride (0.66 g) in N,N-dimethylformamide (4 ml) was stirred at 110° C. for 8 hours. After being cooled, the mixture was poured into ice-water and extracted with ethyl acetate. The organic layer was washed with brine, dried over magnesium sulfate and concentrated in reduced pressure to give a syrup. The syrup was subjected to column chromatography on silica gel and eluted with chloroform, successively with a mixture of chloroform and methanol (10:1). The fractions containing object compound were combined and concentrated under reduced pressure to give 5-{2-(2-(4-tert-butylthiazol-2-yl)benzofuran-5-yloxymethyl]phenylmethyl}-1H-tetrazole (0.21 g).
mp: 80°–84° C.
IR (Nujol): 2700, 2600, 1610, 1580, 1550, 1500 cm$^{-1}$
NMR (CDCl$_3$, δ): 1.40 (9H, s), 4.49 (2H, s), 5.05 (2H, s), 6.83 (1H, dd, J=2.6 Hz and 8.9 Hz), 6.99 (1H, s), 7.03 (1H, d, J=2.6 Hz), 7.19 (1H, s), 7.26–7.38 (6H, m)
FAB-MASS (m/z): 446 ((M+1)$^+$)

EXAMPLE 13

The following compounds were obtained according to a similar manner to that of Example 12.

1)
5-{2-[2-(4-Phenylthiazol-2-yl)benzofuran-5-yloxymethyl]phenylmethyl}-1H-tetrazole mp: 160°–163° C.
IR (Nujol): 2700, 1610, 1590 cm$^{-1}$
NMR (DMSO-d$_6$, δ): 4.43 (2H, s), 5.25 (2H, s), 7.04 (1H, dd, J=2.6 Hz and 9.0 Hz), 7.2–7.8 (10H, m), 8.0–8.1 (2H, m), 8.31 (1H, s)
FAB-MASS (m/z): 466 ((M+1)$^+$)

2)
5-{3-[2-(4-tert-Butylthiazol-2-yl)benzofuran-5-yloxymethyl]phenyl}-1H-tetrazole mp: 170°–171° C.
IR (Nujol): 2700, 1590 cm$^{-1}$
NMR (DMSO-d$_6$, δ): 1.36 (9H, s), 5.28 (2H, s), 7.14 (1H, dd, J=2.5 Hz and 8.8 Hz), 7.36 (1H, d, J=2.5 Hz), 7.47 (2H, s), 7.62–7.74 (3H, m), 8.02 (1H, d, J=7.1 Hz), 8.20 (1H, br s)
MASS (m/z): 431 (M$^+$), 388, 273 (base)

3)
5-{2-[2-(4-Isopropylthiazol-2-yl)benzofuran-5-yloxymethyl]phenylmethyl}-1H-tetrazole mp: 177°–180° C.
IR (Nujol): 3110, 1585, 1230, 1144, 735 cm$^{-1}$
NMR (DMSO-d$_6$, δ): 1.31 (6H, d, J=6.9 Hz), 3.13 (1H, sep, J=6.9 Hz), 4.43 (2H, s), 5.24 (2H, s), 6.99 (1H, dd, J=2.6 Hz and 9.0 Hz), 7.23–7.63 (9H, m)
MASS (m/z): 431 (M$^+$), 388, 259 (base), 244, 130

4)
5-{2-[2-(4-Methylthiazol-2-yl)benzofuran-5-yloxymethyl]phenylmethyl}-1H-tetrazole mp: 205°–206° C.
IR (Nujol): 3150, 1580, 1190, 823 cm$^{-1}$
NMR (DMSO-d$_6$, δ): 2.46 (3H, s), 4.42 (2H, s), 5.23 (2H, s), 6.99 (1H, dd, J=2.6 Hz and 9.0 Hz), 7.22–7.62 (9H, m)
MASS (m/z): 403, 360, 231, 130 (base)

5)
5-{2-[2-(4-(4-Methoxy]phenylthiazol-2-yl)benzofuran-5-yloxymethyl]phenylmethyl}-1H-tetrazole mp: 177°–178° C.
IR (Nujol): 3200–2500, 1610, 1587, 1244, 1194, 1026, 828 cm$^{-1}$
NMR (DMSO-d$_6$, δ): 3.82 (3H, s), 4.44 (2H, s), 5.25 (2H, s), 6.99–7.08 (3H, s), 7.24–7.41 (4H, m), 7.53–7.67 (3H, m), 7.97–8.01 (2H, m), 8.13 (1H, s)
MASS (m/z): 323 (base), 308

6)
5-{2-[2-(4-Trifluoromethylthizaol-2-yl)benzofuran-5-yloxymethyl]phenylmethyl}-1H-tetrazole mp: 214°–215° C.
IR (Nujol): 3130, 1590 cm$^{-1}$
NMR (DMSO-d$_6$, δ): 4.41 (2H, s), 5.26 (2H, s), 7.06 (1H, dd, J=2.6 Hz and 8.9 Hz), 7.2–7.4 (4H, m), 7.52–7.56 (1H, m), 7.66 (1H, d, J=8.9 Hz), 7.68 (1H, s), 8.65 (1H, s)
FAB-MASS (m/z): 479 ((M+Na)$^+$), 458 ((M+1)$^+$), 432

7)
5-{2-[2-(4-tert-Butylthiazol-2-yl)benzo[b]thiophen-5-yloxymethyl]phenylmethyl}-1H-tetrazole mp: 75°–78° C.
IR (Nujol): 2700 (br), 1590, 1530, 1490, 1200 cm$^{-1}$
NMR (CDCl$_3$, δ): 1.39 (9H, s), 4.36 (2H, s), 5.11 (2H, s), 6.90 (1H, s), 6.88 (1H, dd, J=2.5 Hz and 8.7 Hz), 7.23 (1H, d, J=2.5 Hz), 7.59 (1H, s), 7.63 (1H, d, J=8.7 Hz), 7.25–7.44 (4H, m)
FAB-MASS (m/z): 462 ((M+1)$^+$), 392, 290, 274

8)
5-{2-[2-(4,5,6,7-Tetrahydrobenzothiazol-2-yl)benzofuran-5-yloxymethyl]phenylmethyl}-1H-tetrazole mp: 105°–110° C. (dec.)
IR (Nujol): 3300, 2700, 1615, 1580, 1545 cm$^{-1}$
NMR (DMSO-d$_6$, δ): 1.8–1.9 (4H, m), 2.7–2.9 (4H, m), 4.41 (2H, s), 5.23 (2H, s), 6.97 (1H, dd, J=2.6 Hz and 9.0 Hz), 7.22–7.38 (5H, m), 7.50–7.52 (1H, m), 7.58 (1H, d, J=9.0 Hz)
FAB-MASS (m/z): 443 (M$^+$)

9)
5-{2-[2-(4-Cyclobutylthiazol-2-yl)benzofuran-5-yloxymethyl]phenylmethyl}-1H-tetrazole mp: 120°–125° C. (dec.)
IR (Nujol): 3300, 1610, 1580, 1515 cm$^{-1}$
NMR (DMSO-d$_6$, δ): 1.90–2.35 (6H, m), 3.71 (1H, sext, J=8.5 Hz), 4.13 (2H, s), 5.36 (2H, s), 7.10 (1H, dd, J=2.5 Hz and 9.0 Hz), 7.16–7.20 (3H, m), 7.28 (1H, d, J=2.5 Hz), 7.41–7.42 (1H, m), 7.45 (1H, s), 7.51 (1H, s), 7.60 (1H, d, J=9.0 Hz)
FAB-MASS (m/z): 488 ((M+2Na)$^+$), 466 ((M+Na)$^+$), 441 ((M+1)$^+$)

10)

5-{2-[2-(4-(2-Thienyl)thiazol-2-yl)benzofuran-5-yloxymethyl]phenylmethyl}-1H-tetrazole mp: 202°-203° C.

IR (Nujol): 3150, 1610, 1585, 1550 cm$^{-1}$

NMR (DMSO-d$_6$, δ): 4.43 (2H, s), 5.25 (2H, s), 7.02 (1H, dd, J=2.6 Hz and 9.0 Hz), 7.15-7.19 (1H, m), 7.23-7.37 (4H, m), 7.52-7.70 (5H, m), 8.14 (1H, s)

FAB-MASS (m/z): 472 ((M+1)$^+$), 374, 309

11)

5-{2-[2-(4-Neopentylthiazol-2-yl)benzofuran-5-yloxymethyl]phenylmethyl)-1H-tetrazole mp: 150°-153° C.

IR (Nujol): 3110, 2700-2400, 2000-1800, 1617, 1583, 1203, 1005, 825, 740 cm$^{-1}$ NMR (CDCl$_3$, δ): 0.98 (9H, s), 2.71 (2H, s), 4.42 (2H, s), 4.94 (2H, s), 6.78 (1H, dd J=9.0 Hz and 2.5 Hz), 6.90 (1H, d, J=2.5 Hz), 6.96 (1H, s), 7.18-7.37 (7H, m)

MASS (m/z): 459, 416, 287, 231

12)

5-{2-[2-(4-tert-Butylthiazol-2-yl)benzofuran-5-ylmethylthio]phenylmethyl)-1H-tetrazole IR (Nujol): 2700, 2600, 1590, 1550, 1500 cm$^{-1}$ NMR (CDCl$_3$, δ): 1.40 (9H, s), 4.12 (2H, s), 4.27 (2H, s), 7.00 (1H, s), 7.10-7.42 (8H, m)

MASS (m/z): 461 (M+), 270

13)

5-{2-[2-(4-tert-Butylthiazol-2-yl)benzofuran-5-ylmethoxy]phenylmethyl}-1H-tetrazole mp: 186.5°-187° C.

IR (Nujol): 3140, 2700, 2600, 2500, 1600, 1590, 1550 cm$^{-1}$

NMR (CDCl$_3$, δ): 1.42 (9H, s), 4.28 (2H, s), 5.19 (2H, s), 6.96 (1H, td, J=7.5 Hz and 0.8 Hz), 7.01 (1H, s), 7.04 (1H, d, J=7.5 Hz), 7.25-7.36 (2H, m), 7.34 (1H, dd, J=8.5 Hz and 1.8 Hz), 7.37 (1H, d, J=0.9 Hz), 7.56 (1H, d, J=8.5 Hz), 7.60 (1H, dd, J=1.8 Hz and 0.9 Hz)

MASS (m/z): 445 (M+), 270

14)

5-{2-[2-(4-Cyclopropylthiazol-2-yl)benzofuran-5-yloxymethyl]phenylmethyl)-1H-tetrazole mp: 164°-166° C.

IR (Nujol) 1580, 1550, 1520 cm$^{-1}$

NMR (DMSO-d$_6$, δ): 0.86-0.99 (4H, m), 2.10-2.22 (1H, m), 4.42 (2H, s), 5.22 (2H, s), 6.98 (1H, dd, J=9.0 Hz and 2.5 Hz), 7.22-7.40 (3H, m), 7.29 (1H, dd, J=2.5 Hz and 0.8 Hz), 7.41 (1H, d, J=0.8 Hz), 7.45 (1H, s), 7.54 (1H, dd, J=6.3 Hz and 3.0 Hz), 7.60 (1H, d, J=9.0 Hz)

MASS (m/z): 429 (M+), 257, 256

15)

5-{2-[2-(8-Acetyl-4,5,6,7-tetrahydro-8H-thiazolo[5,4-b]azepin-2-yl)benzofuran-5-yloxymethyl]phenylmethyl}-1H-tetrazole mp: 149°-150° C.

IR (Nujol): 1660, 1615 cm$^{-1}$

NMR (DMSO-d$_6$, δ): 1.64-2.0 (4H, m), 2.09 (s) and 2.29 (s)(3H), 2.95-3.05 (2H, m), 3.5-3.9 (2H, m), 4.17 (2H, s), 5.22 (2H, s), 6.94-7.00 (1H, m), 7.27-7.62 (7H, m)

MASS (m/z): 500 (M+), 457, 443, 415, 328, 286

16)

5-{2-[2-(4-(N-Acetyl-tert-butylaminomethyl]thiazol-2-yl)benzofuran-5-yloxymethyl]phenylmethyl}-1H-tetrazole IR (Nujol): 1610, 1550 cm$^{-1}$ NMR (CDCl$_3$, δ): 1.48 (9H, s), 2.16 (3H, s), 4.46 (2H, s), 4.74 (2H, s), 5.17 (2H, s), 6.94 (1H, dd, J=9.0 Hz and 2.6 Hz), 7.11-7.14 (2H, m), 7.32-7.45 (6H, m)

MASS (m/z): 516 (M+)

17)

5-{2-[2-(4-Hexylthiazol-2-yl)benzofuran-5-yloxymethyl]phenylmethyl}-1H-tetrazole mp: 146.5°-147.5° C.

IR (Nujol): 3100, 2700, 1610, 1580, 1560, 1520 cm$^{-1}$

NMR (DMSO-d$_6$, δ): 0.87 (3H, t, J=6.7 Hz), 1.31 (6H, m), 1.70 (2H, m), 2.75 (2H, t, J=7.5 Hz), 4.42 (2H, s), 5.23 (2H, s), 6.98 (1H, dd, J=9.0 Hz and 2.6 Hz), 7.22-7.40 (4H, m), 7.44 (1H, d, J=0.7 Hz), 7.47 (1H, s), 7.55 (1H, dd, J=9.0 Hz and 3.6 Hz), 7.60 (1H, d, J=9.0 Hz)

MASS (m/z): 473 (M+), 430

18)

5-{2-[2-(4-Pentylthiazol-2-yl)benzofuran-5-yloxymethyl]phenylmethyl}-1H-tetrazole mp: 151.0°-151.5° C.

IR (Nujol): 3100, 2700, 1610, 1580, 1560, 1520 cm$^{-1}$

NMR (DMSO-d$_6$, δ): 0.89 (3H, t, J=6.5 Hz), 1.33 (4H, m), 1.70 (2H, m), 2.78 (2H, t, J=7.6 Hz), 4.42 (2H, s), 5.28 (2H, s), 6.98 (1H, dd, J=9.0 Hz and 2.6 Hz), 7.22-7.40 (4H, m), 7.45 (1H, d, J=0.7 Hz), 7.47 (1H, s), 7.55 (1H, dd, J=9.0 Hz and 3.6 Hz), 7.60 (1H, d, J=9.0 Hz)

MASS (m/z): 459 (M+), 430, 414

19)

5-{2-[2-(5-Isopropylthiazol-2-yl)benzofuran-5yloxymethyl]phenylmethyl}-1H-tetrazole mp: 158°-160° C.

IR (Nujol): 2700-2500, 1584, 1204, 1035, 730 cm$^{-1}$

NMR (DMSO-d$_6$, δ): 1.34 (6H, d, J=6.8 Hz), 3.31 (1H, sep, J=6.8 Hz), 4.42 (2H, s), 5.23 (2H, s), 6.98 (1H, dd, J=9.0 Hz and 2.6 Hz), 7.22-7.61 (8H, m), 7.76 (1H, d, J=0.9 Hz)

MASS (m/z): 431 (M+), 388, 259, 244 (base), 130

20)

5-{2-[2-(2-tert-Butylthiazol-4-yl)benzofuran-5yloxymethyl]phenylmethyl}-1H-tetrazole IR (Nujol): 2650, 1650, 1610, 1600, 1550 cm$^{-1}$ NMR (DMSO-d$_6$, δ): 1.45 (9H, s), 4.41 (2H, s), 5.22 (2H, s), 6.91 (1H, dd, J=8.9 Hz and 2.6 Hz), 7.18 (1H, s), 7.22-7.36 (4H, m), 7.53 (1H, d, J=8.9 Hz), 7.51-7.56 (1H, m), 7.96 (1H, s)

MASS (m/z): 445 (M+), 273

EXAMPLE 14

A mixture of 4-tert-butyl-2-[5-(2-methoxycarbonylphenylmethoxy)benzofuran-2-yl]thiazole (0.28 g) and 4N aqueous sodium hydroxide (1.0 ml) in methanol (5 ml) was stirred under reflux 5.5 hours. After being cooled, the resulting solution was concentrated under reduced pressure to give a residue. The residue was dissolved in water and adjusted to pH 4 with diluted aqueous hydrochloric acid to give crystals. The crystals were filtered and washed with water to give 4-tertbutyl-2-[5-(2-carboxyphenylmethoxy)benzofuran-2-yl]thiazole (0.27 g).

mp: 210°–212° C.

IR (Nujol): 2700, 1695, 1605, 1590 cm$^{-1}$

NMR (DMSO-d$_6$, δ): 1.35 (9H, s), 5.51 (2H, s), 7.08 (1H, dd, J=2.5 Hz and 9.0 Hz), 7.26 (1H, d, J=2.5 Hz), 7.39–7.70 (4H, m), 7.45 (1H, s), 7.46 (1H, s), 7.93 (1H, d, J=6.6 Hz)

MASS (m/z): 407 (M+), 273 (base), 258, 244

EXAMPLE 15

The following compounds were obtained according to a similar manner to that of Example 14.

1)

4-tert-Butyl-2-[5-(3-carboxyphenylmethoxy)benzofuran-2-yl]thiazole mp: 248°–250° C.

IR (Nujol): 2600, 1680, 1610, 1600, 1550 cm$^{-1}$

NMR (DMSO-d$_6$, δ): 1.36 (9H, s), 5.16 (2H, s), 7.09 (1H, dd, J=2.6 Hz and 9.0 Hz), 7.3–7.34 (2H, m), 7.44–7.46 (3H, m), 7.62 (1H, d, J=9.0 Hz), 7.86 (1H, d, J=7.4 Hz), 8.01 (1H, br s)

MASS (m/z): 407 (M+), 272, 229

2)

4-tert-Butyl-2-[5-(2-(2,2-dicarboxyethyl]phenylmethoxy)benzofuran-2-yl]thiazole mp: 160°–161° C. (dec.)

IR (Nujol): 3110, 2700, 2600, 2500, 1710, 1630, 1580, 1510 cm$^{-1}$

NMR (CDCl$_3$, δ): 1.41 (9H, s), 3.34 (2H, d, J=7.5 Hz), 3.76 (1H, t, J=7.5 Hz), 5.19 (2H, s), 6.99 (1H, s), 7.04 (1H, dd, J=9.0 Hz and 2.5 Hz), 7.19 (1H, d, J=2.5 Hz), 7.22–7.37 (4H, m), 7.39–7.48 (1H, m), 7.43 (1H, d, J=9.0 Hz)

MASS (m/z): 435, 273, 258

EXAMPLE 16

To a solution of 4-tert-butyl-2-[5-{(2-(dimethylcarbamoyl)ethylthio](3-methoxycarbonylpropylthio)methyl}benzofuran-2-yl]thiazole (0.45 g) in methanol, 1N aqueous lithium hydroxide was added at ambient temperature under nitrogen atmosphere. After being stirred for 15 hours at ambient temperature, the resulting mixture was concentrated under reduced pressure to give a syrup. The syrup was dissolved in water, washed with diethyl ether, adjusted to pH 4 with diluted aqueous hydrochloric acid, and extracted with ethyl acetate. The organic layer was washed with brine, dried over magnesium sulfate and concentrated under reduced pressure to give a syrup. The syrup was subjected to column chromatography on silica gel and eluted with a mixture of chloroform and methanol. The fractions containing object compound were combined and concentrated in reduced pressure to give a syrup of 4-tert-butyl-2-[5-{(3-carboxypropylthio)[2-(dimethylcarbamoylethylthio]methyl}benzofuran-2-yl]-thiazole (0.39 g).

IR (Neat): 2600, 1725, 1620, 1500 cm$^{-1}$

NMR (CDCl$_3$, δ): 1.41 (9H, s), 1.81–2.09 (2H, m), 2.41–2.56 (4H, m), 2.66–2.74 (2H, m), 2.78–3.05 (2H, m), 2.89 (3H, s), 2.93 (3H, s), 5.14 (1H, s), 6.98 (1H, s), 7.32 (1H, s), 7.43–7.53 (2H, m), 7.71 (1H, br s)

FAB-MASS (m/z): 519 ((M−1)−)

EXAMPLE 17

A mixture of 4-tert-butyl-2-[5-(2-methyl-2-methoxycarbonylpropyl)benzofuran-2-yl]thiazole (0.33 g) and 1N aqueous sodium hydroxide (2 ml) in methanol (5 ml) was stirred under reflux for 5 hours. After being cooled, the resulting mixture was concentrated under reduced pressure and adjusted to pH 6 with diluted aqueous hydrochloric acid. The resulting crystals were collected by filtration and washed with water to give 4-tert-butyl-2-[5-(2-carboxy-2-methylpropyl)benzofuran-2-yl]thiazole (0.28 g).

mp: 155°–157° C.

IR (Nujol): 2600, 1730, 1580, 1500 cm$^{-1}$

NMR (CDCl$_3$, δ): 1.24 (6H, s), 1.40 (9H, s), 2.99 (2H, s), 6.96 (1H, s), 7.14 (1H, dd, J=1.8 Hz and 8.7 Hz), 7.27 (1H, s), 7.41 (1H, d, J=1.8 Hz), 7.43 (1H, d, J=8.7 Hz)

MASS (m/z): 357 (M+), 301, 270 (base)

EXAMPLE 18

A solution of 4-tert-butyl-2-[5-(2-carboxyphenylmethoxy)benzofuran-2-yl]thiazole (0.2 g), 2-methylbenzenesulfonamide (0.11 g), 4-dimethylaminopyridine (0.12 g) and 1-(3-dimethylaminopropyl)-3-ethylcarbodiimide hydrochloride (0.19 g) in N,N-dimethylformamide (10 ml) was stirred at ambient temperature for 1 day. The resulting mixture was poured into ice-water. The resulting precipitates were collected by filtration and washed with water. The crude compound was subjected to column chromatography on silica gel and eluted with a mixture of chloroform and methanol (40:1). The fractions containing object compound were combined and concentrated under reduced pressure to give an oil. The oil was crystallized with ethanol and filtered to give 4-tert-butyl-2-{5-[2-(2-methylbenzenesulfonamidocarbonyl)phenylmethoxy]benzofuran-2-yl}thiazole (0.28 g).

mp: 180°–181° C.

IR (Nujol): 1705, 1610, 1590 cm$^{-1}$

NMR (CDCl$_3$, δ): 1.42 (9H, s), 2.61 (3H, s), 5.17 (2H, s), 6.99 (1H, s), 6.96–7.02 (1H, m), 7.30 (1H, s), 7.54 (1H, s), 7.14–7.56 (8H, m), 7.72 (1H, d, J=7.4 Hz), 8.20 (1H, d, J=7.8 Hz)

EXAMPLE 19

The following compounds were obtained according to a similar manner to that of Example 18.

1)

4-tert-Butyl-2-{5-[3-(2-methylbenzenesulfonamidocarbonyl)phenylmethoxy]benzofuran-2-yl}thiazole mp: 145°–148° C.

IR (Nujol): 1660, 1610, 1590 cm$^{-1}$

NMR (DMSO-d$_6$, δ): 1.36 (9H, s), 2.54 (3H, s), 5.16 (2H, s), 7.08 (1H, dd, J=2.6 Hz and 9.0 Hz), 7.31 (1H, d, J=2.6 Hz), 7.44 (1H, s), 7.46 (1H, s), 7.60 (1H, d, J=9.0 Hz), 7.13–7.62 (5H, m), 7.83–7.91 (2H, m), 8.02 (1H, br s)

MASS (m/z): 560 (M+), 483

2)

4-tert-Butyl-2-[5-{2-methyl-2-(1H-tetrazol-5-yl)carbamoylpropyl}benzofuran-2-yl]thiazole mp: 260°–280° C. (dec.)

IR (Nujol): 3300, 1600, 1560, 1500 cm$^{-1}$

NMR (DMSO-d$_6$, δ): 1.19 (6H, s), 1.35 (9H, s), 3.05 (2H, s), 7.23 (1H, dd, J=2.0 Hz and 8.7 Hz), 7.41 (1H, s), 7.45 (1H, s), 7.51 (1H, d, J=2.0 Hz), 7.53 (1H, d, J=8.7 Hz), 10.28 (1H, s)

FAB-MASS (m/z): 423 ((M−1)−), 380

3)
4-tert-Butyl-2-{5-[2-(2-methylbenzenesulfonamidocarbonyl)phenylthiomethyl]benzofuran-2-yl}thiazole mp: 270°-273° C.
IR (Nujol): 1590, 1560, 1540 cm$^{-1}$
NMR (DMSO-d$_6$, δ): 1.36 (9H, s), 2.56 (3H, s), 4.14 (2H, s), 7.01-7.35 (6H, m), 7.41 (1H, dd, J=8.5 Hz and 1.6 Hz), 7.47 (1H, s), 7.49 (1H, s), 7.62 (1H, d, J=8.5 Hz), 7.72 (1H, d, J=1.6 Hz), 7.85 (1H, dd, J=6.6 Hz and 1.8 Hz), 7.89 (1H, dd, J=7.7 Hz and 1.0 Hz)
FAB-MASS (m/z): 615 ((M+K)+), 576 (M+)

4)
4-tert-Butyl-2-{(5-[2-(2-methylbenzenesulfonamidocarbonylmethyl)phenylmethoxy]benzofuran-2-yl}thiazole mp: 112°-114° C.
IR (Nujol): 1590 cm$^{-1}$
NMR (DMSO-d$_6$, δ): 1.36 (9H, s), 2.45 (3H, s), 3.52 (2H, s), 5.13 (2H, s), 7.03 (1H, br d, J=9.0 Hz), 7.18-7.46 (8H, m), 7.42 (1H, br s), 7.47 (1H, s), 7.59 (1H, d, J=8.9 Hz), 7.84 (1H, d, J=7.5 Hz)
MASS (m/z): 574 (M+)

EXAMPLE 20

To a cooled mixture of 4-tert-butyl-2-(5-formylbenzofuran-2-yl)thiazole (0.713 g), N,N-dimethyl-3-mercaptopropionamide (0.37 g) and methyl 4-mercaptobutyrate (0.37 g) in acetonitrile (15 ml), boron trifluoride etherate (1.38 ml) was added dropwise at 0° C. After being stored in refrigerator for 18 hours, the resulting mixture was poured into ice-water, adjusted to pH 7 with aqueous sodium hydrogen carbonate solution and extracted with diethyl ether. The organic layer was washed with brine, dried over magnesium sulfate and concentrated under reduced pressure to give a mixture containing 3 compounds. The mixture was subjected to column chromatography on silica gel and eluted with toluene, successively a mixture of toluene and ethyl acetate (20:1 to 3:1) and at last a mixture of chloroform and methanol (10:1). The fractions eluted with toluene were concentrated under reduced pressure to give an oil of 4-tert-butyl-2-{5-[bis-(3-methoxycarbonylpropylthio)methyl]benzofuran-2-yl}thiazole (0.3 g).
IR (Neat): 1740, 1590, 1500, 1440 cm$^{-1}$
NMR (CDCl$_3$, δ): 1.41 (9H, s), 1.88 (4H, q, J=7.0 Hz), 2.39 (4H, t, J=7.0 Hz), 2.5-2.7 (4H, m), 3.65 (6H, s), 5.0 (1H, s), 6.99 (1H, s), 7.33 (1H, s), 7.42-7.53 (2H, m), 7.68 (1H, br s)
MASS (m/z): 402, 300, 286, 270

The fractions eluted with a mixture of toluene and ethyl acetate were concentrated under reduced pressure to give an oil of 4-tert-butyl-2-[5-{(2-(dimethylcarbamoyl)ethylthio](3-methoxycarbonylpropylthio)methyl}benzofuran-2-yl]thiazole (0.72 g).
IR (Neat): 1740, 1640, 1500 cm$^{-1}$
NMR (CDCl$_3$, δ): 1.41 (9H, s), 1.89 (2H, q, J=7.0 Hz), 2.43 (2H, t, J=7.0 Hz), 2.5-2.7 (4H, m), 2.89 (3H, s), 2.91 (3H, s), 2.9-3.0 (2H, m), 3.64 (3H, s), 5.07 (1H, s), 6.98 (1H, s), 7.31 (1H, s), 7.43-7.52 (2H, m), 7.70 (1H, br s)
MASS (m/z): 534 (M+), 402, 301, 286, 270

The fractions eluted with a mixture of chloroform and methanol were concentrated under reduced pressure to give an oil of 4-tert-butyl-2-[5-{bis-[2-(dimethylcarbamoylethylthio]methyl}benzofuran-2-yl]thiazole (0.37 g).
IR (Neat): 1640, 1500 cm$^{-1}$
NMR (CDCl$_3$, δ): 1.41 (9H, s), 2.51 (4H, t, J=8.0 Hz), 2.90 (6H, s), 2.91 (6H, s), 2.8-3.0 (4H, m), 5.16 (1H, s), 6.99 (1H, s), 7.32 (1H, s), 7.43-7.52 (2H, m), 7.72 (1H, br s)
MASS (m/z): 533 (M+), 433, 401, 301, 286, 270

EXAMPLE 21

To a cooled mixture of 4-tert-butyl-2-(5-formylbenzofuran-2-yl)thiazole (2.85 g) in methanol (28 ml), sodium borohydride (0.38 g) was added in small portions. After being stirred at the same temperature for 2 hours, the resulting solution was poured into ice-water. The resulting precipitates were collected by filtration and washed with water to give 4-tert-butyl-2-(5-hydroxymethylbenzofuran-2-yl)thiazole (2.87 g).
mp: 143°-144° C.
IR (Nujol): 3450, 1500 cm$^{-1}$
NMR (CDCl$_3$, δ): 1.41 (9H, s), 1.72 (1H, br s), 4.77 (2H, s), 6.98 (1H, s), 7.30 (1H, s), 7.32 (1H, dd, J=2.2 Hz and 8.7 Hz), 7.50 (1H, d, J=8.7 Hz), 7.59 (1H, d, J=2.2 Hz)

EXAMPLE 22

A mixture of 4-tert-butyl-2-(5-hydroxymethylbenzofuran-2-yl)thiazole (2.82 g) and thionyl chloride (1.4 ml) in dichloromethane (30 ml) was stirred under reflux for 1 hour. After being cooled, the resulting mixture was adjusted to pH 7 with aqueous sodium hydrogen carbonate. The organic layer was separated, washed with brine, dried over magnesium sulfate, concentrated under reduced pressure to give crystals of 4-tert-butyl-2-(5-chloromethylbenzofuran-2-yl)thiazole (2.93 g).
mp: 117°-119° C.
IR (Nujol): 1590, 1500 cm$^{-1}$
NMR (CDCl$_3$, δ): 1.41 (9H, s), 4.70 (2H, s), 6.99 (1H, s), 7.31 (1H, d, J=0.7 Hz), 7.37 (1H, dd, J=8.7 Hz and 1.7 Hz), 7.53 (1H, d, J=8.7 Hz), 7.64 (1H, d, J=1.7 Hz)
MASS (m/z): 305 (M+), 290 (base), 270, 254

EXAMPLE 23

To a cooled suspension of lithium diisopropylamide {(1.45 mM tetrahydrofuran and n-hexane solution), 3.7 ml} and methyl 2-methylpropionate (0.6 g), a dried hexamethylphosphoric triamide (0.5 ml) was added at −65 to −57° C. Subsequently, 4-tert-butyl-2-(5-chloromethylbenzofuran-2-yl)thiazole was added to the mixture in small portions. After being stirred for 30 minutes at the same temperature, additive hexamethylphosphoric triamide (1.5 ml) was added to the mixture. The reaction mixture was gradually elevated to −10° C. for 1 hour. The resulting mixture was poured into ice-water and extracted with diethyl ether. The organic layer was washed with brine, dried over magnesium sulfate and concentrated under reduced pressure to give a syrup. The syrup was subjected to column chromatography on silica gel and eluted with a mixture of n-hexane and ethyl acetate (20:1). The fractions containing object compound were combined and concentrated under reduced pressure to give 4-tert-butyl-2-[5-(2-methyl-2-methoxycarbonylpropyl)benzofuran-2-yl]thiazole (0.43 g).
mp: 42°-43° C.
IR (Nujol): 1730, 1590, 1500 cm$^{-1}$
NMR (CDCl$_3$, δ): 1.21 (6H, s), 1.41 (9H, s), 2.95 (2H, s), 3.66 (3H, s), 6.96 (1H, s), 7.07 (1H, dd, J=1.8 Hz and 8.7 Hz), 7.28 (1H, d, J=0.8 Hz), 7.34 (1H, d, J=1.8 Hz), 7.43 (1H, d, J=8.7 Hz)
MASS (m/z): 371 (M+), 312, 270 (base)

EXAMPLE 24

A solution of 5-methoxy-2-benzofurancarbothioamide (350.0 g) and 1-bromopinacolone (260.9 ml) in 2-propanol (3.5 l) was stirred under reflux for 40 minutes. After being cooled to 13° C., the resulting precipitates were collected by filtration, washed with diisopropyl ether (500 ml) and dried to give a salt of hydrogen bromide (381.6 g). The salt was added to a mixture of sodium hydroxide (41.4 g), ice-water (3.7 l) and dichloromethane (3.7 l). After being stirred for 10 minutes, the organic layer was washed with brine (3 L), dried over magnesium sulfate, treated with activated charcol (15 g), and concentrated under reduced pressure to give 4-tert-butyl-2-(5-methoxybenzofuran-2-yl)thiazole (289.3 g).

IR (Nujol): 3150, 1625, 1590, 1500 cm$^{-1}$

NMR (CDCl$_3$, δ): 1.41 (9H, s), 3.85 (3H, s), 6.94 (1H, dd, J=2.6 Hz and 8.9 Hz), 6.96 (1H, s), 7.05 (1H, d, J=2.6 Hz), 7.28 (1H, d, J=0.8 Hz), 7.43 (1H, d, J=8.9 Hz)

EXAMPLE 25

To a solution of 5-}2-[2-(4-tert-butylthiazol-2-yl)benzofuran-5-yloxymethyl]phenylmethyl}-1H-tetrazole (0.1 g) in methanol (1 ml), 1N aqueous sodium hydroxide (0.225 ml) was added at ambient temperature. The resulting solution was concentrated under reduced pressure and dried in vacuo. The resulting residue was crystallized with a mixture of ethyl acetate and diisopropyl ether. The crystals were collected by filtration, washed with a mixture of ethyl acetate and diisopropyl ether (1:1) to give a sodium salt of 5-{2-[2-(4-tert-butylthiazol-2-yl)benzofuran-5-yloxymethyl]phenylmethyl}-1H-tetrazole trihydrate (0.11 g).

mp: 126°–130° C. (dec.)

IR (Nujol): 3650, 3180, 1650, 1630, 1600 cm$^{-1}$

NMR (DMSO-$_6$, δ): 1.36 (9H, s), 4.10 (2H, s), 5.37 (2H, s), 7.11 (1H, dd, J=2.5 and 9.0 Hz), 7.15–7.20 (3H, m), 7.28 (1H, d, J=2.5 Hz), 7.41–7.46 (3H, m), 7.60 (1H, d, J=9.0 Hz)

Elemental Analysis: C$_{24}$H$_{22}$N$_5$NaO$_2$S.3H$_2$O; Calcd.: C 54.88, H 5.45, N 13.33. Found: C 54.82, H 5.33, N 13.29

EXAMPLE 26

The following compound was obtained according to similar manners to those of Examples 4 and 24.

2-(5-Hydroxybenzofuran-2-yl)-4-isopropylthiazole mp: 209°–211° C.

IR (Nujol): 3140, 1580, 1212, 790 cm$^{-1}$

NMR (DMSO-d$_6$, δ): 1.30 (6H, d, J=6.9 Hz), 3.11 (1H, sep, J=6.7 Hz), 6.84 (1H, dd, J=2.5 Hz and 8.8 Hz), 7.00 (1H, d, J=2.4 Hz), 7.38 (1H, d, J=0.7 Hz), 7.43 (1H, d, J=0.7 Hz), 7.47 (1H, d, J=8.9 Hz), 9.37 (1H, s)

MASS (m/z): 259 (M$^+$), 244 (base), 160

EXAMPLE 27

The following compounds were obtained according to a similar manner to that of Example 24.

1) 2-(5-Methoxybenzofuran-2-yl)-4-methylthiazole

IR (Nujol): 1615, 1600, 1580, 1510 cm$^{-1}$

NMR (CDCl$_3$, δ): 2.53 (3H, s), 3.85 (3H, s), 6.94 (1H, s), 6.95 (1H, dd, J=2.5 Hz and 9.1 Hz), 7.05 (1H, d, J=2.4 Hz), 7.26 (1H, s), 7.43 (1H, d, J=8.9 Hz)

MASS (m/z): 245 (M$^+$, base), 230, 202

2) 2-(5-Hydroxybenzofuran-2-yl)-4-[4-methoxy)phenylthiazole mp: 218°–219° C.

IR (Nujol): 3100, 1610, 1580 cm$^{-1}$

NMR (DMSO-d$_6$, δ): 3.82 (3H, s), 6.89 (1H, dd, J=2.5 Hz and 9.0 Hz), 7.04 (1H, d, J=2.5 Hz), 7.08 (1H, s), 7.06 (2H, d, J=9.0 Hz), 7.50 (1H, s), 7.52 (1H, d, J=9.0 Hz), 7.98 (2H, d, J=9.0 Hz), 8.11 (1H, s), 9.41 (1H, s)

MASS (m/z): 323 (M$^+$, base), 308, 280, 149

3) 2-(5-Methoxybenzofuran-2-yl)-4-trifluoromethylthiazole mp: 119°–120° C.

IR (Nujol): 3150, 1590, 1530, 1460 cm$^{-1}$

NMR (DMSO-d$_6$, δ): 3.86 (3H, s), 7.00 (1H, dd, J=2.5 Hz and 8.9 Hz), 7.07 (1H, d, J=2.5 Hz), 7.43 (1H, d, J=8.9 Hz), 7.41 (1H, s), 7.78 (1H, s)

MASS (m/z): 299 [M$^+$, base), 284, 256, 228

4) 2-(5-Methoxybenzo[b]thiophen-2-yl)-4-tert-butylthiazole mp: 130°–131° C.

IR (Nujol): 1600, 1565, 1535, 1500 cm$^{-1}$

NMR (CDCl$_3$, δ): 1.39 (9H, s), 3.87 (3H, s), 6.88 (1H, s), 7.01 (1H, dd, J=2.5 Hz and 8.7 Hz), 7.22 (1H, d, J=2.5 Hz), 7.65 (1H, s), 7.68 (1H, d, J=8.7 Hz)

MASS (m/z): 303 (M$^+$), 288 (base), 261

5) 4-(Adamantan-1-yl)-2-(5-methoxybenzofuran-2-yl)thiazole mp: 172°–173° C.

IR (Nujol): 1620, 1590 cm$^{-1}$

NMR (CDCl$_3$, δ): 1.78–1.81 (6H, m), 2.05–2.10 (9H, m), 3.85 (3H, s), 6.92 (1H, s), 6.94 (1H, dd, J=2.6 Hz and 9.0 Hz), 7.05 (1H, d, J=2.6 Hz), 7.28 (1H, s), 7.43 (1H, d, J=9.0 Hz)

MASS (m/z): 365 (M$^+$, base), 308, 271

6) 2-(5-Methoxybenzofuran-2-yl)-4,5,6,7-tetrahydrobenzothiazole mp: 107°–108° C.

IR (Nujol): 1625, 1590, 1540 cm$^{-1}$

NMR (CDCl$_3$, δ): 1.89–1.92 (4H, m), 2.85–2.88 (4H, m), 3.85 (3H, s), 6.94 (1H, dd, J=2.6 Hz and 9.0 Hz), 7.05 (1H, d, J=2.6 Hz), 7.21 (1H, s), 7.42 (1H, d, J=9.0 Hz)

MASS (m/z): 285 (M$^+$, base), 257, 173

7) 4-Cyclobutyl-2-(5-methoxybenzofuran-2-yl)thiazole mp: 88°–89° C.

IR (Nujol): 1625, 1590, 1500, 1480 cm$^{-1}$

NMR (CDCl$_3$, δ): 1.92–2.44 (6H, m), 3.75 (1H, sext, J=8.3 Hz), 6.94 (1H, dd, J=2.6 Hz and 9.0 Hz), 6.98 (1H, s), 7.05 (1H, d, J=2.6 Hz), 7.28 (1H, d, J=0.8 Hz), 7.43 (1H, d, J=9.0 Hz)

MASS (m/z): 285 (M$^+$), 257 (base)

8) 2-(5-Methoxybenzofuran-2-yl)-4-(2-thienyl)thiazole

IR (Nujol): 1610, 1580 cm$^{-1}$

NMR (DMSO-d$_6$, δ): 3.82 (3H, s), 7.04 (1H, dd, J=2.6 Hz and 9.0 Hz), 7.17 (1H, dd, J=3.6 Hz and 5.4

Hz), 7.29 (1H, d, J=2.6 Hz), 7.56 (1H, d, J=0.8 Hz), 7.59-7.7 (3H, m), 8.14 (1H, s)

MASS (m/z): 313 (M+), 298, 270

9) 2-(5-Methoxybenzofuran-2-yl)-4-(2-pyridyl)thiazole mp: 125°-130° C.

NMR (DMSO-d₆, δ): 3.83 (3H, s), 7.04 (1H, dd, J=2.6 Hz and 9.0 Hz), 7.27 (1H, d, J=2.6 Hz), 7.42 (1H, dd, J=4.8 Hz and 7.8 Hz), 7.60 (1H, s), 7.64 (1H, d, J=9.0 Hz), 7.97 (1H, dt, J=1.6 Hz and 7.8 Hz), 8.18 (1H, d, J=7.8 Hz), 8.44 (1H, s), 8.67 (1H, dd, J=1.6 Hz and 4.8 Hz)

MASS (m/z): 308 (M+), 207, 135

10) 2-(5-Hydroxybenzofuran-2-yl)-4-neopentylthiazole mp: 194°-196° C.

NMR (DMSO-d₆, δ): 0.95 (9H, s), 2.69 (2H, s), 6.84 (1H, dd, J=8.8 Hz and 2.5 Hz), 7.00 (1H, d, J=2.5 Hz), 7.35-7.49 (3H, m), 9.36 (1H, s)

MASS (m/z): 287, 231, 160

11)
4-Cyclopropyl-2-(5-hydroxybenzofuran-2-yl)thiazole

IR (Nujol): 3140, 1600, 1580, 1520 cm⁻¹

NMR (CDCl₃, δ): 0.94-1.01 (4H, m), 2.10-2.19 (1H, m), 6.87 (1H, dd, J=8.8 Hz and 2.6 Hz), 6.88 (1H, s), 7.02 (1H, d, J=2.6 Hz), 7.03 (1H, s), 7.38 (1H, d, J=8.8 Hz)

MASS (m/z): 257 (M+)

12) 2-tert-Butyl-4-(5-methoxybenzofuran-2-yl)thiazole

IR (Nujol): 3140, 1630, 1590 cm⁻¹

NMR (CDCl₃, δ): 1.49 (9H, s), 3.85 (3H, s), 6.88 (1H, dd, J=8.9 Hz and 2.6 Hz), 7.05 (1H, dd, J=2.6 Hz and 0.6 Hz), 7.12 (1H, d, J=0.6 Hz), 7.38 (1H, d, J=8.9 Hz), 7.51 (1H, s)

MASS (m/z): 287 (M+), 272

13)
4-(Chloromethyl)-2-(5-hydroxybenzofuran-2-yl)thiazole mp: 188°-190° C.

IR (Nujol): 3080, 1580, 1208, 808, 710 cm⁻¹

NMR (DMSO-d₆, δ): 4.91 (2H, s), 6.85-6.90 (1H, m), 7.02-7.03 (1H, m), 7.46-7.51 (2H, m), 7.91 (1H, s), 9.42 (1H, s)

14) 4-Hexyl-2-(5-hydroxybenzofuran-2-yl)thiazole

IR (Nujol): 3150, 2700, 1610, 1580, 1510 cm⁻¹

NMR (CDCl₃, δ): 0.89 (3H, t, J=6.4 Hz), 1.20-1.60 (6H, m), 1.76 (2H, m), 2.85 (2H, t, J=7.7 Hz), 6.87 (1H, dd, J=8.8 Hz and 2.6 Hz), 6.95 (1H, s), 7.03 (1H, d, J=2.6 Hz), 7.27 (1H, s), 7.40 (1H, d, J=8.8 Hz)

MASS (m/z): 301 (M+), 286, 272, 258, 244

15) 2-(5-Hydroxybenzofuran-2-yl)-4-pentylthiazole

IR (Nujol): 3100, 2700, 1610, 1580, 1510 cm⁻¹

NMR (CDCl₃, δ): 0.91 (3H, t, J=7.0 Hz), 1.30-1.42 (4H, m), 1.68-1.81 (2H, m), 2.87 (2H, t, J=7.7 Hz), 6.88 (1H, dd, J=8.8 Hz and 2.5 Hz), 6.96 (1H, s), 7.03 (1H, d, J=2.5 Hz), 7.34 (1H, s), 7.40 (1H, d, J=8.8 Hz)

MASS (m/z): 287 (M+), 272, 258, 244, 231, 160

16) 5-Isopropyl-2-(5-methoxybenzofuran-2-yl)thiazole

IR (Neat): 1610, 1580, 1510 cm⁻¹

NMR (CDCl₃, δ): 1.40 (6H, d, J=6.8 Hz), 3.27 (1H, sep, J=6.8 Hz), 3.85 (3H, s), 6.95 (1H, dd, J=8.9 Hz and 2.6 Hz), 7.06 (1H, dd, J=2.6 Hz and 0.9 Hz), 7.23 (1H, d, J=0.9 Hz), 7.42 (1H, d, J=8.9 Hz), 7.59 (1H, s)

MASS (m/z): 272 (M+), 258

EXAMPLE 28

The following compounds were obtained by reacting the compounds, which were prepared according to a similar manner to that of Example 12, with hydrogen chloride.

1)
5-{2-[2-[4-(Adamantan-1-yl)thiazol-2-yl]benzofuran-5-yloxymethyl]phenylmethyl}-1H-tetrazole hydrochloride mp: 115°-122° C. (dec.)

IR (Nujol): 3400, 2700, 1740, 1590 cm⁻¹

NMR (DMSO-d₆, δ): 1.75-1.80 (6H, m), 1.98-2.2 (6H, m), 2.07 (3H, s), 4.42 (2H, s), 5.24 (2H, s), 6.98 (1H, dd, J=2.6 Hz and 9.0 Hz), 7.23-7.36 (5H, m), 7.41 (1H, s), 7.44 (1H, s), 7.52-7.56 (1H, m), 7.62 (1H, d, J=9.0 Hz)

2)
5-{2-[2-[4-(2-Pyridyl)thiazol-2-yl]benzofuran-5-yloxymethyl]phenylmethyl}-1H-tetrazol hydrochloride mp: 135°-136° C. (dec.)

IR (Nujol): 3400, 2700, 2600, 1720, 1620, 1600, 1580, 1535, 1490 cm⁻¹

NMR (DMSO-d₆, δ): 4.44 (2H, s), 5.27 (2H, s), 6.06 (1H), 7.05 (1H, dd, J=2.6 Hz and 9.0 Hz), 7.25-7.40 (4H, m), 7.53-7.57 (1H, m), 7.65-7.71 (3H, m), 8.29 (1H, dt, J=1.8 Hz and 7.8 Hz), 8.41 (1H, d, J=7.8 Hz), 8.76 (1H, d, J=5.1 Hz), 8.80 (1H, s)

FAB-MASS (m/z): 467 ((M+1)+)

EXAMPLE 29

The following compound was obtained according to a similar manner to that of Preparation 1.

2-[5-(2-Formylphenoxymethyl)benzofuran-2-yl]-4-tert-butylthiazole

IR (Neat): 1690, 1600, 1500 cm⁻¹

NMR (CDCl₃, δ): 1.42 (9H, s), 5.28 (2H, s), 6.99 (1H, s), 7.01-7.23 (2H, m), 7.35 (1H, d, J=0.8 Hz), 7.42 (1H, dd, J=8.5 Hz and 1.7 Hz), 7.55 (1H, ddd, J=8.5 Hz, 7.3 Hz and 1.8 Hz), 7.58 (1H, d, J=8.5 Hz), 7.69 (1H, dd, J=1.7 Hz and 0.8 Hz), 7.87 (1H, dd, J=7.7 Hz and 1.8 Hz), 10.56 (1H, s)

MASS (m/z): 391 (M+), 270

EXAMPLE 30

The following compound was obtained according to a similar manner to that of Example 21.

4-tert-Butyl-2-[5-(2-hydroxymethyl)phenoxymethyl-benzofuran-2-yl]thiazole

IR (Nujol): 3300, 1610, 1590, 1490 cm⁻¹

NMR (CDCl₃, δ): 1.42 (9H, s), 4.77 (2H, s), 5.20 (2H, s), 6.96 (1H, t, J=6.6 Hz), 6.99 (1H, s), 6.99 (1H, d, J=7.8 Hz), 7.23-7.35 (2H, m), 7.35 (1H, d, J=0.7 Hz), 7.40 (1H, dd, J=8.5 Hz and 1.7 Hz), 7.57 (1H, d, J=8.5 Hz), 7.67 (1H, dd, J=1.7 Hz and 0.7 Hz)

MASS (m/z): 393 (M+), 270

EXAMPLE 31

A mixture of 4-hexyl-2-[5-(2-chloromethylphenylmethoxy)benzofuran-2-yl]thiazole (0.80 g), sodium cyanide (0.16 g) and potassium iodide (0.13 g) in methanol (10 ml) was refluxed for 2 hours. After being cooled, the mixture was poured into brine, extracted with ethyl acetate, dried over magnesium sulfate and concentrated in reduced pressure. The resulting residue was subjected to column chromatography on silica gel and eluted with a mixture of ethyl acetate and chloroform (1:33). The fractions containing object compound were combined and concentrated under reduced pressure to give an oil of 4-hexyl-2-[5-(2-cyanomethylphenylmethoxy)benzofuran-2-yl]thiazole (0.66 g).

IR (Neat): 3110, 2250, 1610, 1580 cm$^{-1}$

NMR (CDCl$_3$, δ): 0.90 (3H, t, J=6.5 Hz), 1.35 (6H, m), 1.77 (2H, m), 2.85 (2H, t, J=7.7 Hz), 3.90 (2H, s), 5.12 (2H, s), 6.96 (1H, s), 7.01 (1H, dd, J=8.9 Hz and 2.6 Hz), 7.17 (1H, dd, J=2.6 Hz and 0.8 Hz), 7.29 (1H, d, J=0.8 Hz), 7.31–7.54 (5H, m)

Mass (m/z): 156, 129

EXAMPLE 32

The following compounds were obtained according to a similar manner to that of Example 31.

1)

4-Trifluoromethyl-2-[5-(2-cyanomethylphenylmethoxy)benzofuran-2-yl]thiazole mp: 113°–115° C.

IR (Nujol): 3150, 2250, 1610, 1590 cm$^{-1}$

NMR (CDCl$_3$, δ): 3.90 (2H, s), 5.13 (2H, s), 7.08 (1H, dd, J=2.6 Hz and 8.9 Hz), 7.20 (1H, d, J=2.6 Hz), 7.3–7.5 (6H, m), 7.80 (1H, s)

MASS (m/z): 414 (M+), 285, 228, 130 (base)

2)

4-tert-Butyl-2-[5-(2-cyanomethylphenylmethoxy)benzo[b]thiophen-2-yl]thiazole

IR (Nujol): 3050, 2240, 1590, 1520 cm$^{-1}$

NMR (CDCl$_3$, δ): 1.40 (9H, s), 3.89 (2H, s), 5.14 (2H, s), 6.90 (1H, s), 7.07 (1H, dd, J=2.4 Hz and 8.7 Hz), 7.33 (1H, d, J=2.4 Hz), 7.68 (1H, s), 7.70 (1H, d, J=8.7 Hz), 7.15–7.55 (4H, m)

MASS (m/z): 418 (M+, base), 391, 288, 260, 245, 130, 105

3)

4-(2-Pyridyl)-2-[5-(2-cyanomethylphenylmethoxy)benzofuran-2-yl]thiazole mp: 125°–130° C.

IR (Nujol): 3130, 2250, 1615, 1590, 1570 cm$^{-1}$

NMR (CDCl$_3$, δ): 3.91 (2H, s), 5.13 (2H, s), 7.05 (1H, dd, J=2.6 Hz and 9.0 Hz), 7.20 (1H, d, J=2.6 Hz), 7.24–7.30 (1H, m), 7.40 (1H, s), 7.39–7.55 (5H, m), 7.82 (1H, dt, J=1.8 Hz and 7.6 Hz), 8.18 (1H, s), 8.26 (1H, d, J=8.0 Hz), 8.64–8.66 (1H, m)

MASS (m/z): 423 (M+), 308, 282, 254, 223

4)

4-Neopentyl-2-[5-(2-cyanomethylphenylmethoxy)benzofuran-2-yl]thiazole mp: 83°–85° C.

IR (Neat): 2250, 1617, 1590, 1195, 1015, 795, 745 cm$^{-1}$

NMR (CDCl$_3$, δ): 1.00 (9H, s), 2.76 (2H, s), 3.90 (2H, s), 5.11 (2H, s), 6.95 (1H, s), 7.01 (1H, dd, J=8.9 Hz and 2.5 Hz), 7.16 (1H, d, J=2.5 Hz), 7.22–7.55 (6H, m)

MASS (m/z): 416, 389, 360, 286, 230, 130 (base)

5)

4-tert-Butyl-2-[5-(2-cyanomethylphenylthiomethyl)benzofuran-2-yl]thiazole

IR (Neat): 2260, 1590, 1500 cm$^{-1}$

NMR (CDCl$_3$, δ): 1.41 (9H, s), 3.69 (2H, s), 4.15 (2H, s), 6.98 (1H, s), 7.15–7.47 (8H, m)

MASS (m/z): 418 (M+), 270

6)

4-tert-Butyl-2-[5-(2-cyanomethylphenoxymethyl)benzofuran-2-yl]thiazole

IR (Neat): 3140, 2250, 1600, 1500 cm$^{-1}$

NMR (CDCl$_3$, δ): 1.41 (9H, s), 3.74 (2H, s), 5.20 (2H, s), 6.93–7.04 (2H, m), 6.99 (1H, s), 7.25–7.43 (2H, m), 7.35 (1H, d, J=0.7 Hz), 7.42 (1H, dd, J=8.5 Hz and 1.7 Hz), 7.57 (1H, d, J=8.5 Hz), 7.70 (1H, dd, J=1.7 Hz and 0.7 Hz)

MASS (m/z): 402 (M+), 270

7)

4-Cyclopropyl-2-[5-(2-cyanomethylphenylmethoxy)benzofuran-2-yl]thiazole

IR (Neat): 3100, 2260, 1610, 1590, 1510 cm$^{-1}$

NMR (CDCl$_3$, δ): 0.93–1.06 (4H, m), 2.08–2.22 (1H, m), 3.90 (2H, s), 5.11 (2H, s), 6.89 (1H, s), 7.01 (1H, dd, J=8.9 Hz and 2.6 Hz), 7.11–7.59 (5H, m), 7.16 (1H, dd, J=2.6 Hz and 0.8 Hz), 7.29 (1H, d, J=0.8 Hz)

MASS (m/z): 386 (M+), 257, 256

8)

4-tert-Butyl-2-(5-cyanomethylbenzofuran-2-yl)thiazole

IR (Nujol): 3140, 2250, 1590, 1500 cm$^{-1}$

NMR (CDCl$_3$, δ): 1.41 (9H, s), 3.85 (2H, s), 7.00 (1H, s), 7.27 (1H, dd, J=8.5 Hz and 1.9 Hz), 7.32 (1H, d, J=0.9 Hz), 7.54 (1H, d, J=8.5 Hz), 7.60 (1H, dd, J=1.9 Hz and 0.9 Hz)

MASS (m/z): 296 (M+)

9)

4-tert-Butyl-2-[5-(2-cyanomethylphenylmethoxy)benzofuran-2-yl]thiazole

IR (Neat): 3140, 2250, 1610, 1600 cm$^{-1}$

NMR (CDCl$_3$, δ): 1.50 (9H, s), 3.91 (2H, s), 5.11 (2H, s), 6.94 (1H, dd, J=8.9 Hz and 2.6 Hz), 7.12–7.15 (2H, m), 7.24–7.60 (5H, m), 7.52 (1H, s)

MASS (m/z): 402 (M+), 375, 272

10)

4-(N-Acetyl-tert-butylaminomethyl)-2-[5-(2-cyanomethylphenylmethoxy)benzofuran-2-yl]thiazole IR (Neat): 3100, 2250, 1650, 1590 cm$^{-1}$ NMR (CDCl$_3$, δ): 1.50 (9H, s), 2.18 (3H, s), 3.90 (2H, s), 4.77 (2H, s), 5.13 (2H, s), 7.05 (1H, dd, J=9.0 Hz and 2.6 Hz), 7.15–7.57 (8H, m)

MASS (m/z): 473 (M+)

11)

4-Pentyl-2-[5-(2-cyanomethylphenylmethoxy)benzofuran-2-yl]thiazole

IR (Neat): 3110, 2250, 1610, 1580, 1500 cm$^{-1}$

NMR (CDCl$_3$, δ): 0.92 (3H, t, J=7.0 Hz), 1.33–1.46 (4H, m), 1.78 (2H, m), 2.85 (2H, t, J=7.7 Hz), 3.90 (2H, s), 5.12 (2H, s), 6.96 (1H, s), 7.01 (1H, dd, J=8.9 Hz and 2.6 Hz), 7.17 (1H, dd, J=2.6 Hz and 0.8 Hz), 7.29 (1H, d, J=0.8 Hz), 7.33–7.51 (5H, m)

MASS (m/z): 416 (M+), 401, 387, 373

EXAMPLE 33

To a mixture of 4-tert-butyl-2-[5-(2-carboxyphenylthiomethyl)benzofuran-2-yl]thiazole (0.65 g) in tetrahydrofuran (10 ml), lithium aluminum hydride (0.12 g) was added under cooling with ice bath. After being stirred at ambient temperature for 5 hours, the resulting mixture was poured into a mixture of ice and diluted aqueous hydrochloric acid and extracted with toluene. The organic layer was washed with brine, dried over magnesium sulfate, and concentrated under reduced pressure. The residue was subjected to column chromatography on silica gel and eluted with a mixture of ethyl acetate and toluene (1:9). The fractions containing object compound were combined and concentrated under reduced pressure to give 4-tert-butyl-2-[5-(2-hydroxymethylphenylthiomethyl)benzofuran-2-yl]thiazole (0.45 g).

IR (Nujol): 3400, 1590, 1500 cm$^{-1}$

NMR CDCl$_3$, $\delta$): 1.40 (9H, s), 2.00 (1H, br s), 4.17 (2H, s), 4.64 (2H, s), 6.97 (1H, s), 7.18–7.28 (3H, m), 7.24 (1H, s), 7.34–7.38 (3H, m), 7.49 (1H, d, J=8.5 Hz)

MASS (m/z): 409, 270

EXAMPLE 34

To a solution of 4-tert-butyl-2-(5-chloromethylbenzofuran-2-yl)thiazole (0.68 g) and thiosalicylic acid (0.72 g) in N,N-dimethylformamide (5 ml), potassium carbonate (0.78 g) was added dropwise at 100° C. After being stirred for one hour, the reaction mixture was cooled, poured into a mixture of ice and diluted aqueous hydrochloric acid and extracted with ethyl acetate. The organic layer was washed with aqueous sodium hydrogen carbonate solution to remove thiosalicylic acid, dried over magnesium sulfate and concentrated under reduced pressure. The residue was crystallized with ethyl acetate and filtered to give 4-tert-butyl-2-[5-(2-carboxyphenylthiomethyl)benzofuran-2-yl]thiazole (0.49 g).

mp: 205°–207° C.

IR (Nujol): 1680, 1590 cm$^{-1}$

NMR (DMSO-d$_6$, $\delta$): 1.36 (9H, s), 4.33 (2H, s), 7.21 (1H, ddd, J=7.4 Hz, 5.4 Hz and 2.9 Hz), 7.45–7.55 (2H, m), 7.48 (1H, s), 7.48 (1H, dd, J=8.5 Hz and 1.5 Hz), 7.52 (1H, s), 7.67 (1H, d, J=8.5 Hz), 7.79 (1H, d, J=1.5 Hz), 7.89 (1H, d, J=7.4 Hz), 12.8–13.2 (1H, m)

MASS (m/z): 423 (M+)

EXAMPLE 35

A mixture of 4-tert-butyl-2-[5-(2-hydroxymethylphenylthiomethyl)benzofuran-2-yl]thiazole (0.42 g), thionyl chloride (0.1 g) and N,N-dimethylformamide (3 drops) in chloroform (5 ml) was stirred for 3 hours at ambient temperature. The resulting mixture was poured into aqueous sodium hydrogen carbonate solution and extracted with chloroform. The extract was washed with brine, dried over magnesium sulfate and concentrated under reduced pressure to give 4-tert-butyl-2-[5-(2-chloromethylphenylthiomethyl)benzofuran-2-yl]thiazole (0.49 g).

IR (Neat): 1590, 1500 cm$^{-1}$

NMR (CDCl$_3$, $\delta$): 1.40 (9H, s), 4.20 (2H, s), 4.68 (2H, s), 6.97 (1H, s), 7.20–7.28 (3H, m), 7.25 (1H, s), 7.32–7.41 (3H, m), 7.44 (1H, d, J=8.5 Hz)

MASS (m/z): 427 (M+), 270

4-tert-Butyl-2-[5-(2-chloromethylphenoxymethyl)benzofuran-2-yl]thiazole

IR (Neat): 3140, 1600, 1590, 1490 cm$^{-1}$

NMR (CDCl$_3$, $\delta$): 1.42 (9H, s), 4.72 (2H, s), 5.23 (2H, s), 6.96 (1H, td, J=7.7 Hz and 1.0 Hz), 6.98 (1H, dd, J=7.7 Hz and 1.0 Hz), 7.00 (1H, s), 7.30 (1H, td, J=7.7 Hz and 1.7 Hz), 7.39 (1H, dd, J=7.7 Hz and 1.7 Hz), 7.43 (1H, d, J=0.7 Hz), 7.45 (1H, dd, J=8.5 Hz and 1.7 Hz), 7.57 (1H, d, J=8.5 Hz), 7.73 (1H, dd, J=1.7 Hz and 0.7 Hz)

MASS (m/z): 411 (M+), 270

EXAMPLE 37

To a solution of 2-ethoxycarbonylbenzyltriphenylphosphonium bromide (605 mg) and 4-tert-butyl-2-(5-formylbenzofuran-2-yl)thiazole (285 mg) in acetonitrile (5.00 ml), 1,8-diazabicyclo[5.4.0]undec-7-ene (0.317 ml) was added. The resulting solution was heated under reflux for 10 hours. After concentration under reduced pressure, diisopropyl ether was added to the residue. The resulting insoluble material was removed by filtration. After concentration of filtrate under reduced pressure, n-heptane was added to the residue. The resulting insoluble material removed again by filtration. After concentration of filtrate, the residue was subjected to column chromatography on silica gel and eluted with a mixture of n-hexane and ethyl acetate. The fractions containing object compound were combined and concentrated under reduced pressure to give 4-tert-butyl-2-[5-{2-(2-ethoxycarbonylphenyl)ethenyl}benzofuran-2-yl]thiazole (280 mg) as a mixture of E and Z isomer as a viscous oil, which was used in the next step without further purification.

IR (Nujol): 1712, 1498, 1255, 1233, 1070 cm$^{-1}$

NMR (DMSO-d$_6$, $\delta$): 1.35–1.54 (12H, m), 4.31–4.47 (2H, m), 6.71–6.77 (1H), 7.04–7.36 (6H, m), 7.93–8.04 (1H, m)

MASS (m/z): 431 (M+), 358

EXAMPLE 38

To a solution of 4-tert-butyl-2-[5-{2-(2-ethoxycarbonylphenyl)ethenyl}benzofuran-2-yl]thiazole (250 mg) in methanol (20.0 ml), 10% palladium on carbon (140 mg) was added. The mixture was hydrogenated for 3 hours (3.0–2.3 atm). The catalyst was removed by filtration and washed with methanol. The filtrate was evaporated under reduced pressure to give 4-tert-butyl-2-[5-{2-(2-ethoxycarbonylphenyl)ethyl}benzofuran-2-yl]thiazole (270 mg).

mp: 75°–77° C.

IR (Nujol): 1680, 1270 cm$^{-1}$

NMR (DMSO-d$_6$, $\delta$): 1.36–1.74 (12H, m), 2.96–3.04 (2H, m), 3.27–3.35 (2H, m), 4.37 (2H, q, J=7.1 Hz), 6.97 (1H, s)

MASS (m/z): 433 (M+), 388

EXAMPLE 39

To a solution of 4-tert-butyl-2-[5-{2-(2-ethoxycarbonylphenyl)ethyl}benzofuran-2-yl]thiazole (170 mg) in methanol (5 ml), 1N aqueous sodium hydroxide (1.58 ml) was added. The resulting mixture was heated under reflux for 9 hours. After being cooled, 1N hydrochloric acid was added. The resulting precipitates were collected by filtration, and washed by water to give 4-tert-butyl-2-[5-{2-(2-carboxyphenyl)ethyl}benzofuran-2-yl]thiazole (86.3 mg).

mp: 147°–148° C.

IR (Nujol): 1685, 1295, 1267 cm$^{-1}$

NMR (DMSO-d$_6$, $\delta$): 1.36 (9H, s), 2.93 (2H, m), 3.26 (2H, m), 7.27–7.35 (3H, m), 7.42–7.63 (5H, m) 7.83 (1H, d, J=7.8 Hz)

MASS (m/z): 405 (M+), 270

EXAMPLE 40

A mixture of DL-α-(5-methoxybenzofuran-2-yl)carbonylamino-ε-caprolactam (0.2 g) and phosphorus pentasulfide (0.2 g) in pyridin (2 ml) was stirred under reflux for 6.5 hours. After being cooled, the resulting mixture was poured into ice-water, and extracted with ethyl acetate. The organic layer was washed with brine, dried over magnesium sulfate and concentrated under reduced pressure to give crude crystal, which was collected by filtration and washed with ethanol to give 2-(5-methoxybenzofuran-2-yl)-4,5,6,7-tetrahydro-8H-thiazolo[5,4-b]azepine (0.09 g).

mp: 121°–125° C.

IR (Nujol): 3250, 1620, 1590, 1520, 1480 cm$^{-1}$

NMR (CDCl$_3$, δ): 1.69–1.74 (2H, m), 1.79–1.84 (2H, m), 2.95–3.00 (2H, m), 3.11–3.16 (2H, m), 3.9–4.1 (1H, br), 3.84 (3H, s), 6.89 (1H, dd, J=2.6 Hz and 9.0 Hz), 7.01 (1H, d, J=2.6 Hz), 7.05 (1H, s), 7.38 (1H, d, J=9.0 Hz)

MASS (m/z): 300 (M+), 225, 160, 128

EXAMPLE 41

To a cooled solution of 2-(5-methoxybenzofuran-2-yl)-4,5,6,7-tetrahydro-8H-thiazolo[5,4-b]azepine (1.3 g) and pyridine (0.65 ml) in N,N-dimethylformamide (20 ml), a solution of acetyl chloride (0.41 g) in dichloromethane (2 ml) was added dropwise below 10° C. After being stirred for 2 hours, the resulting mixture was poured into brine and extracted with ethyl acetate. The organic layer was washed with brine, dried over magnesium sulfate and concentrated under reduced pressure to give a syrup, which was crystallized from ethanol and collected by filtration to give 8-acetyl-2-(5-methoxybenzofuran-2-yl) 4,5,6,7-tetrahydro-8H-thiazolo[5,4-b]azepine (1.07 g).

mp: 147°–149° C.

IR (Nujol): 1660, 1620, 1590, 1540 cm$^{-1}$

NMR (DMSO-d$_6$, δ): 1.64–2.0 (4H, m), 2.08 (s) and 2.29 (s)(3H), 2.89–2.97 (2H, m), 3.6–3.7 (m) and 3.85–3.88 (m)(2H), 3.81 (3H, s), 6.97 (dd) and 7.01 (dd)(1H, J=2.6 Hz and 9.0 Hz), 7.19 (d) and 7.23 (d)(1H, J=2.6 Hz), 7.36 (s) and 7.46 (s)(1H), 7.55 (d) and 7.59 (d)(1H, J=2.6 Hz)

MASS (m/z): 342, 300, 191

EXAMPLE 42

A mixture of 5-{2-[2-(8-acetyl-4,5,6,7-tetrahydro-8H-thiazolo[5,4-b]azepin-2-yl)benzofuran-5-yloxymethyl]-phenylmethyl}-1H-tetrazole (65 mg) and 2N aqueous sodium hydroxide (0.65 ml) in ethanol (6 ml) was stirred under reflux for 4 hours. After being cooled, the resulting mixture was concentrated under reduced pressure to give residue. Water was added to the residue and adjusted to pH 3 with diluted aqueous hydrochloric acid. The appeared precipitates were collected by filtration and washed with water to give 5-{2-[2-(4,5,6,7-tetrahydro-8H-thiazolo[5,4-b]azepin-2-yl)benzofuran-5-yloxymethyl]phenylmethyl}-1H-tetrazole (35 mg).

mp: 110°–118° C.

IR (Nujol): 3300, 1610, 1545 cm$^{-1}$

NMR (DMSO-d$_6$, δ): 1.61–1.71 (4H, m), 2.8–2.9 (2H, m), 3.0–3.1 (2H, m), 4.40 (2H, s), 5.22 (2H, s), 6.50 (1H, s), 6.89 (1H, dd, J=2.6 Hz and 9.0 Hz), 7.10 (1H, s), 7.22–7.52 (6H, m)

FAB-MASS (m/z): 459 (M+), 309, 286

EXAMPLE 43

A solution of methylmagnesium bromide in tetrahydrofuran (1N, 15 ml) was added to diethyl malonate (7.33 g) at 0° C. for 10 minutes. The mixture was stirred for 2 hours at ambient temperature. To the mixture, 4-tert-butyl-2-(5-chloromethylbenzofuran-2-yl)thiazole (3.50 g) was added and stirred for 23 hours at 45° C. The resulting mixture was concentrated under reduced pressure and added to the solution of 4N hydrogen chloride in ethyl acetate. The resulting precipitates were collected by filtration and washed with n-hexane and diisopropyl ether to give the salt. The salt was added to the aqueous sodium hydrogen carbonate solution and extracted with ethyl acetate. The extract was washed with brine, dried over magnesium sulfate and concentrated under reduced pressure to give 4-tert-butyl-2-[5-(2,2-diethoxycarbonylethyl)benzofuran-2-yl]thiazole (5.80 g).

IR (Neat): 3140, 1740, 1590, 1500 cm$^{-1}$

NMR (CDCl$_3$, δ): 1.20 (6H, t, J=7.1 Hz), 1.41 (9H, s), 3.31 (2H, d, J=7.8 Hz), 3.68 (1H, t, J=7.8 Hz), 4.16 (4H, q, J=7.1 Hz), 6.97 (1H, s), 7.18 (1H, dd, J=8.6 Hz and 1.7 Hz), 7.27 (1H, s), 7.44 (1H, d, J=1.7 Hz), 7.45 (1H, d, J=8.6 Hz)

MASS (m/z): 429 (M+)

EXAMPLE 44

The following compound was obtained according to a similar manner to that of Example 43.

4-tert-Butyl-2-[5-{2-(2,2-diethoxycarbonylethyl)-phenylmethoxy}benzofuran-2-yl]thiazole IR (Neat): 3140, 3100, 1730, 1610, 1590, 1500 cm$^{-1}$ NMR (CDCl$_3$, δ): 1.17 (6H, t, J=7.1 Hz), 1.41 (9H, s), 3.35 (2H, d, J=7.6 Hz), 3.83 (1H, t, J=7.6 Hz), 4.13 (4H, q, J=7.1 Hz), 5.14 (2H, s), 6.97 (1H, s), 7.02 (1H, dd, J=8.9 Hz and 2.6 Hz), 7.18 (1H, d, J=2.6 Hz), 7.23–7.28 (4H, m), 7.42–7.46 (1H, m), 7.44 (1H, d, J=8.9 Hz)

MASS (m/z): 535 (M+), 273, 263, 258

EXAMPLE 45

A mixture of 4-tert-butyl-2-[5-{2-(2,2-dicarboxyethyl)phenylmethoxy}benzofuran-2-yl]thiazole (1.30 g) in xylene (20 ml) was refluxed with stirring for 7 hours. After being cooled, the mixture was subjected to column chromatography on silica gel (45 g) and eluted with a mixture of methanol and chloroform. The fractions containing object compound were combined and concentrated under reduced pressure. The residue was recrystallized from a mixture of diethyl ether and petroleum ether to give 4-tert-butyl-2-[5-{2-(2-carboxyethyl)phenylmethoxy}benzofuran-2-yl]thiazole (0.86 g).

mp: 134°–137° C.

IR (Nujol): 2650, 1700, 1660, 1620, 1590 cm$^{-1}$

NMR (CDCl$_3$, δ): 1.40 (9H, s), 2.75 (2H, t, J=7.6 Hz), 3.06 (1H, t, J=7.6 Hz), 5.10 (2H, s), 6.96 (1H, s), 7.00 (1H, dd, J=9.0 Hz and 2.5 Hz), 7.15 (1H, d, J=2.5 Hz), 7.20–7.36 (4H, m), 7.40–7.46 (1H, m), 7.43 (1H, d, J=9.0 Hz)

MASS (m/z): 435 (M+), 273, 258

EXAMPLE 46

A mixture of 4-tert-butyl-2-(5-formylbenzofuran-2-yl)thiazole (4.46 g), hydroxylamine hydrochloride (3.96 g) and sodium acetate anhydrous (5.0 g) in acetic acid (40 ml) was stirred at ambient temperature for 3 hours. Subsequently, acetic anhydride (13 ml) was added to the mixture. After being stirred for 30 minutes at the same temperature, the reaction mixture was stirred at 120° C. for 2 hours. After being cooled, the mixture was poured into water, followed by collecting by filtration. The precipitates were washed with water and air-dried at ambient temperature. The crude products were washed with petroleum ether to give 4-tert-butyl-2-(5-cyanobenzofuran-2-yl)thiazole (4.44 g).

IR (Nujol): 3140, 3100, 2240, 1610, 1590, 1500 cm$^{-1}$

NMR (CDCl$_3$, δ): 1.42 (9H, s), 7.06 (1H, s), 7.39 (1H, s), 7.62 (1H, d, J=1.2 Hz), 7.62 (1H, d, J=2.2 Hz), 7.97 (1H, dd, J=2.2 Hz and 1.2 Hz)

MASS (m/z): 282 (M+), 267

EXAMPLE 47

A mixture of 4-tert-butyl-2-[5-(2,2-diethoxycarbonylethyl)benzofuran-2-yl]thiazole (3.99 g) and conc. hydrochloric acid (20 ml) was stirred under reflux for 6 hours. After being cooled, the resulting mixture was extracted with ethyl acetate. The extract was allowed to stand until there were no further precipitates separated out. The precipitates were collected by filtration and washed with ethyl acetate to give 4-tert-butyl-2-[5-(2,2-dicarboxyethyl)benzofuran-2-yl]thiazole (0.96 g).

mp: >320° C.

IR (Nujol): 3450, 3140, 2700, 1690, 1580, 1500 cm$^{-1}$

NMR (DMSO-d$_6$, δ): 1.35 (9H, s), 3.01 (1H, t, J=4.9 Hz), 3.25 (2H, d, J=4.9 Hz), 7.21 (1H, dd, J=8.5 Hz and 1.8 Hz), 7.45 (1H, s), 7.44–7.48 (2H, m), 7.51 (1H, d, J=8.5 Hz)

MASS (m/z): 372 (M+−1), 369, 354, 329, 314, 254

The filtrate was concentrated under reduced pressure, dissolved partly in diethyl ether and filtrated. To the filtrate, petroleum ether was added and the resulting precipitates were collected by filtration and washed with petroleum ether to give 4-tert-butyl-2-[5-(2-carboxyethyl)benzofuran-2-yl]thiazole (1.11 g).

mp: 157°–160° C.

IR (Nujol): 2700, 1710, 1590, 1500 cm$^{-1}$

NMR (CDCl$_3$, δ): 1.41 (9H, s), 2.74 (2H, t, J=7.6 Hz), 3.00 (2H, t, J=7.6 Hz), 6.97 (1H, s), 7.18 (1H, dd, J=8.5 Hz and 1.8 Hz), 7.28 (1H, s), 7.44 (1H, d, J=1.8 Hz), 7.46 (1H, d, J=8.5 Hz)

MASS (m/z): 329 (M+), 314, 254

EXAMPLE 48

A mixture of 4-tert-butyl-2-[5-(2-chloromethylphenylmethoxy)benzofuran-2-yl]thiazole (1.56 g), sodium iodide (0.50 g) and sodium carbonate (0.83 g) in dimethylsulfoxide (15 ml) was stirred at 100° C. for 10 hours. After being cooled, the resulting mixture was poured into ice-water and extracted with ethyl acetate. The organic layer was washed with brine, dried over magnesium sulfate and concentrated under reduced pressure. The residue was subjected to column chromatography on silica gel and eluted with a mixture of ethyl acetate and toluene (1:20). The fractions containing object compound were combined and concentrates under reduced pressure to give 4-tert-butyl-2-[5-(2-formylphenylmethoxy)benzofuran-2-yl]thiazole (0.75 g).

IR (Nujol): 1700, 1620, 1600, 1590, 1500 cm$^{-1}$

NMR (CDCl$_3$, δ): 1.41 (9H, s), 5.56 (2H, s), 6.97 (1H, s), 7.06 (1H, dd, J=8.9 Hz and 2.6 Hz), 7.17 (1H, br d, J=2.6 Hz), 7.27 (1H, br s), 7.46 (1H, d, J=8.9 Hz), 7.54 (1H, t, J=7.5 Hz), 7.66 (1H, td, J=7.5 Hz and 1.5 Hz), 7.84 (1H, d, J=7.5 Hz), 7.91 (1H, dd, J=7.5 Hz and 1.5 Hz), 10.23 (1H, s)

MASS (m/z): 391 (M+), 273, 258

EXAMPLE 49

A mixture of 4-tert-butyl-2-[5-(2-formylphenylmethoxy)benzofuran-2-yl]thiazole (0.61 g), methyl methylsulfinylmethyl sulfide (0.46 g) and triton B (phase transfer) (0.7 g) in tetrahydrofuran (3 ml) was stirred under reflux for 5 hours. After being cooled, the resulting mixture was poured into ice-water and extracted with ethyl acetate. The organic layer was washed with diluted aqueous hydrochloric acid and brine, dried over magnesium sulfate and concentrated under reduced pressure to give a syrup. The syrup was subjected to column chromatography on silica gel and eluted with a mixture of ethyl acetate and chloroform (1:5). The fractions containing object compound were combined and concentrated in reduced pressure to give a syrup of 4-tert-butyl-2-[5-{2-[2-methylsulfinyl-2-methylthioethenyl)phenylmethoxy}benzofuran-2-yl]thiazole (0.25 g).

IR (Neat): 3100, 1610, 1590, 1500 cm$^{-1}$

NMR (CDCl$_3$, δ): 1.41 (9H, s), 2.39 (3H, s), 2.73 (3H, s), 5.11 (1H, d, J=16.6 Hz), 5.16 (1H, d, J=16.6 Hz), 6.97 (1H, s), 6.99 (1H, dd, J=8.9 Hz and 2.6 Hz), 7.13 (1H, br d, J=2.5 Hz), 7.25–7.45 (4H, m), 7.58 (1H, m), 7.77 (1H, dd, J=5.5 Hz and 3.6 Hz), 7.92 (1H, s)

MASS (m/z): 497 (M+), 434, 273, 258

EXAMPLE 50

A mixture of 4-tert-butyl-2-[5-{2-[2-methylsulfinyl-2-methylthioethenyl)phenylmethoxy}benzofuran-2-yl]thiazole (0.25 g) and 35% aqueous hydrochloric acid (1 ml) in 1,2-dimethoxyethane (3 ml) was stirred at 90° C. for 3 hours. After being cooled, the resulting mixture was concentrated under reduced pressure, poured into water and extracted with ethyl acetate. The organic layer was washed with brine, dried over magnesium sulfate and concentrated under reduced pressure to give a syrup. The syrup was subjected to column chromatography on silica gel and eluted with a mixture of methanol and chloroform. The fractions containing object compound were combined and concentrated in reduced pressure to give 4-tert-butyl-2-[5-(2-carboxymethylphenylmethoxy)benzofuran-2-yl]thiazole (0.10 g).

The obtained compound was reacted with hydrogen chloride to give the corresponding salt. The spectrum date of this compound coincided with those of the compound obtained in Example 51.

EXAMPLE 51

A mixture of 4-tert-butyl-2-[5-(2-cyanomethylphenylmethoxy)benzofuran-2-yl]thiazole (0.5 g) and 40% aqueous potassium hydroxide (10 ml) in diethylene glycol monomethyl ether (10 ml) was heated at 110–120° C. for 1.5 hours. After being cooled, the resulting solution was poured into ice-water, acidified with diluted aqueous hydrochloric acid and extracted with ethyl acetate. The organic layer was washed with brine, dried over magnesium sulfate and concentrated under reduced pressure to give crude residue. The residue was subjected to column chromatography on silica gel and eluted with a mixture of n-hexane and ethyl acetate (4:1). The fractions containing object compound were combined and concentrated to give an oil. The oil was dissolved in aqueous sodium hydrogen carbonate and washed with ethyl acetate. The ethyl acetate layer was concentrated under reduced pressure to give an oil, which was dissolved in aqueous sodium hydroxide and adjusted to pH 1 with diluted aqueous hydrochloric acid. The resulting precipitates were collected by filtration and washed with water to give 4-tert-butyl-2-[5-(2-carboxymethylphenylmethoxy)benzofuran-2-yl]thiazole hydrochloride (5.00 g).

IR (Nujol): 3400–3200, 3100, 2600, 1720, 1590 cm$^{-1}$

NMR (DMSO-d$_6$, δ): 1.36 (9H, s), 3.2–3.4 (2H, m), 3.73 (2H, s), 5.16 (2H, s), 7.06 (1H, dd, J=2.6 Hz and 9.0 Hz), 7.32 (1H, s), 7.43 (1H, s), 7.60 (1H, d, J=9.0 Hz), 7.3–7.6 (5H, m)

MASS (m/z): 421 (M$^+$—HCl), 273, 258 (base), 231

EXAMPLE 52

A mixture of 4-chloromethyl-2-(5-hydroxybenzofuran-2-yl)thiazole (1.38 g), potassium iodide 0.58 g) and tert-butylamine (6 ml) in N,N-dimethylformamide (6 ml) was stirred overnight at ambient temperature, poured into brine and extracted with ethyl acetate. The extract was washed with water and brine. The solution was dried over magnesium sulfate and concentrated under reduced pressure. The resulting precipitate were washed with ethyl acetate to give 4-(tert-butylaminomethyl)-2-(5-hydroxybenzofuran-2-yl)thiazole (1.18 g).

IR (Nujol): 3140, 1640, 1570, 1520 cm$^{-1}$

NMR (CDCl$_3$, δ): 1.33 (9H, s), 3.95 (2H, s), 6.70 (1H, dd, J=8.8 Hz and 2.5 Hz), 6.78 (1H, dd, J=2.5 Hz and 0.8 Hz), 6.91 (1H, d, J=0.8 Hz), 7.14 (1H, s), 7.21 (1H, d, J=8.8 Hz)

MASS (m/z): 302 (M$^+$)

EXAMPLE 53

A mixture of 4-(tert-butylaminomethyl)-2-(5-hydroxybenzofuran-2-yl)thiazole (0.82 g) and acetic anhydride (0.75 g) in ethyl acetate (10 ml) was stirred under reflux for 4 hours. After being cooled, the resulting mixture was concentrated under reduced pressure. A solution of the resulting mixture in methanol (3 ml) and conc. ammonia water (1 ml) was stirred for 2 hours at ambient temperature, poured into brine, extracted with ethyl acetate, dried over magnesium sulfate and concentrated under reduced pressure to give 4-(N-acetyl-tert-butylaminomethyl)-2-(5-hydroxybenzofuran-2-yl)thiazole (0.93 g).

IR (Nujol): 3250, 1590, 1510 cm$^{-1}$

NMR (DMSO-d$_6$, δ): 1.40 (9H, s), 2.11 (3H, s), 4.71 (2H, s), 6.85 (1H, dd, J=8.9 Hz and 2.5 Hz), 7.02 (1H, dd, J=2.5 Hz and 0.7 Hz), 7.39 (1H, d, J=0.7 Hz), 7.48 (1H, d, J=8.9 Hz), 7.61 (1H, s), 9.39 (1H, s)

What we claim is:

1. A compound of the formula:

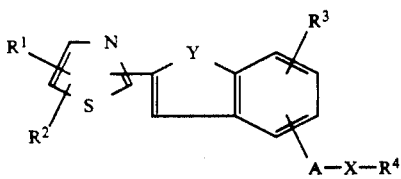

wherein
R$^1$ is lower alkyl optionally substituted with halogen, lower alkylamino or lower alkyl(acyl)amino; cyclo(lower)alkyl; tricycloalkyl; aryl optionally substituted with lower alkoxy; thienyl; or pyridyl;
R$^2$ is hydrogen or halogen, or
R$^1$ and R$^2$ are taken together with the adjacent atoms to form cycloalken ring or tetrahydroazepine optionally substituted with acyl,
R$^3$ is hydrogen, halogen, hydroxy, lower alkyl or lower alkoxy,
R$^4$ is hydrogen; acyl; cyano; aryl optionally substituted with hydroxy(lower)alkyl, halo(lower)alkyl, cyano(lower)alkyl, tetrazolyl(lower)alkyl or acyl; or lower alkyl which may be substituted with substituent(s) selected from the group consisting of halogen, cyano, hydroxy, lower alkylsulfonyloxy, arylsulfonyloxy, acyl, acyl(lower)alkylthio and aryl optionally substituted with halo(lower)alkyl, cyano(lower)alkyl, tetrazolyl(lower)alkyl, cyano, acyl, acyl(lower)alkyl, tetrazolyl or (lower alkylsulfinyl)(lower alkylthio)lower alkenyl;
wherein in R$^1$ and R$^2$ taken together R$^1$ and R$^4$ acyl is selected from the group consisting of carboxy, esterified carboxy, carbamoyl optionally substituted with lower alkyl arylsulfonyl, lower alkylsulfonyl, lower alkanoyl, aroyl and heterocycliccarbonyl,
A is lower alkylene, lower alkenylene or a single bond,
X is a single bond, O or S, and
Y is O or S,
provided that A or X is not a single bond when R$^1$ is lower alkyl or aryl and R$^2$ is hydrogen, or pharmaceutically acceptable salts thereof.

2. A compound according to claim 1, wherein
R$^1$ is lower alkyl or aryl,
R$^2$ is hydrogen,
R$^4$ is hydrogen; lower alkanoyl; carboxy; esterified carboxy; tetrazolylcarbamoyl; or lower alkyl which may be substituted with substituent(s) selected from the group consisting of halogen, hydroxy, lower alkylsulfonyloxy, arylsulfonyloxy, carboxy, esterified carboxy, tetrazolylcarbamoyl, carboxy(lower) alkylthio, esterified carboxy(lower)alkylthio, lower alkylcarbamoyl(lower)alkylthio and aryl optionally substituted with halo(lower)alkyl, cyano(lower)alkyl, tetrazolyl(lower)alkyl, cyano, carboxy, esterified carboxy, lower alkanoyl, arylsulfonylcarbamoyl, carboxy(lower)alkyl, esterified carboxy(lower)alkyl, arylsulfonylcarbamoyl(lower)alkyl or tetrazolyl;
A is a single bond,
X is a single bond or O, and
Y is O.

3. A compound according to claim 2, wherein R$^4$ is hydrogen; lower alkanoyl; carboxy; esterified carboxy; tetrazolylcarbamoyl; or lower alkyl which may be substituted with substituent(s) selected from the group consisting of halogen, hydroxy, lower alkylsulfonyloxy, arylsulfonyloxy, carboxy, esterified carboxy, tetrazolylcarbamoyl, carboxy(lower)alkylthio, esterified carboxy(lower)alkylthio, lower alkylcarbamoyl(lower)alkylthio and aryl optionally substituted with halo(lower)alkyl, cyano(lower)alkyl, tetrazolyl(lower)alkyl, cyano, carboxy, esterified carboxy, lower alkanoyl, arylsulfonylcarbamoyl or tetrazolyl.

4. A compound according to claim 2, wherein
R$^1$ is lower alkyl,
R$^3$ is hydrogen,
R$^4$ is lower alkyl which is substituted with phenyl substituted with tetrazolyl(lower)alkyl, carboxy(lower)alkyl, esterified carboxy(lower)alkyl, arylsulfonylcarbamoyl(lower)alkyl or tetrazolyl, and
X is O.

5. A compound of claim 4, which is 5-{2-[2-(4-tert-butylthiazol-2-yl)benzofuran-5-yloxymethyl]phenylmethyl}-1H-tetrazol, its trihydrate or sodium salt thereof.

6. A pharmaceutical composition comprising an effective amount of a compound of claim 1, as an active ingredient, in association with a pharmaceutically acceptable carrier or excipient.

7. A method for the therapeutic treatment prevention of allergy or inflammation which comprises administering an effective amount of a compound of claim 1 to a human being or animal.

8. A compound of claim 4, which is 4-tert-butyl-2-[5-(2-carboxymethylphenylmethoxy)benzofuran-2-yl]thiazole or its hydrochloride.

* * * * *